US010238490B2

(12) United States Patent
Gifford, III

(10) Patent No.: US 10,238,490 B2
(45) Date of Patent: Mar. 26, 2019

(54) IMPLANT HEART VALVE DEVICES, MITRAL VALVE REPAIR DEVICES AND ASSOCIATED SYSTEMS AND METHODS

(71) Applicant: Twelve, Inc., Redwood City, CA (US)

(72) Inventor: Hanson Gifford, III, Woodside, CA (US)

(73) Assignee: Twelve, Inc., Redwood City, CA (US)

(*) Notice: Subject to any disclaimer, the term of this patent is extended or adjusted under 35 U.S.C. 154(b) by 209 days.

(21) Appl. No.: 15/241,155

(22) Filed: Aug. 19, 2016

(65) Prior Publication Data
US 2017/0049571 A1 Feb. 23, 2017

Related U.S. Application Data

(60) Provisional application No. 62/208,458, filed on Aug. 21, 2015.

(51) Int. Cl.
A61F 2/24 (2006.01)

(52) U.S. Cl.
CPC ............ *A61F 2/2454* (2013.01); *A61F 2/246* (2013.01); *A61F 2/2445* (2013.01); *A61F 2/2463* (2013.01); *A61F 2/2466* (2013.01); *A61F 2/2412* (2013.01); *A61F 2/2487* (2013.01); *A61F 2210/0014* (2013.01); *A61F 2210/0061* (2013.01); *A61F 2210/0085* (2013.01); *A61F 2230/0004* (2013.01);
(Continued)

(58) Field of Classification Search
CPC ...... A61F 2/246–2/2466; A61F 2/2487; A61F 2/2454–2/2457
See application file for complete search history.

(56) References Cited

U.S. PATENT DOCUMENTS 3,526,219 A 9/1970 Balamuth
3,565,062 A 2/1971 Kuris
(Continued)

FOREIGN PATENT DOCUMENTS

CN 1440261 9/2003
CN 101076290 11/2007
(Continued)

OTHER PUBLICATIONS

US 9,265,606, 02/2016, Buchbinder et al. (withdrawn)
(Continued)

*Primary Examiner* — Yashita Sharma
*Assistant Examiner* — Rebecca S Preston

(57) ABSTRACT

Systems, devices and methods for repairing a native heart valve. In one embodiment, a repair device for repairing a native mitral valve having an anterior leaflet and a posterior leaflet between a left atrium and a left ventricle comprises a support having a contracted configuration and an extended configuration, and an appendage, such as a flap or apron extending from the support. In the contracted configuration, the support is sized to be inserted under the posterior leaflet between a wall of the left ventricle and chordae tendineae. In the extended configuration, the support is configured to project anteriorly with respect to a posterior wall of the left ventricle by a distance sufficient to position at least a portion of the posterior leaflet toward the anterior leaflet, and the appendage is configured to extend beyond an edge of the posterior leaflet toward the anterior leaflet.

19 Claims, 22 Drawing Sheets

(52) U.S. Cl.
CPC .............. *A61F 2250/0003* (2013.01); *A61F 2250/0063* (2013.01); *A61F 2250/0069* (2013.01)

(56) References Cited

U.S. PATENT DOCUMENTS

| | | | |
|---|---|---|---|
| 3,589,363 A | 6/1971 | Banko | |
| 3,667,474 A | 6/1972 | Lapkin et al. | |
| 3,823,717 A | 7/1974 | Pohlman et al. | |
| 3,861,391 A | 1/1975 | Antonevich et al. | |
| 3,896,811 A | 7/1975 | Storz | |
| 4,042,979 A | 8/1977 | Angell | |
| 4,188,952 A | 2/1980 | Loschilov et al. | |
| 4,431,006 A | 2/1984 | Trimmer et al. | |
| 4,445,509 A | 5/1984 | Auth | |
| 4,484,579 A | 11/1984 | Meno et al. | |
| 4,490,859 A | 1/1985 | Black et al. | |
| 4,587,958 A | 5/1986 | Noguchi et al. | |
| 4,589,419 A | 5/1986 | Laughlin et al. | |
| 4,602,911 A | 7/1986 | Ahmadi et al. | |
| 4,646,736 A | 3/1987 | Auth | |
| 4,692,139 A | 9/1987 | Stiles | |
| 4,747,821 A | 5/1988 | Kensey et al. | |
| 4,750,902 A | 6/1988 | Wuchinich et al. | |
| 4,777,951 A | 10/1988 | Cribier et al. | |
| 4,787,388 A | 11/1988 | Hofmann | |
| 4,796,629 A | 1/1989 | Grayzel | |
| 4,808,153 A | 2/1989 | Parisi | |
| 4,819,751 A | 4/1989 | Shimada et al. | |
| 4,841,977 A | 6/1989 | Griffith et al. | |
| 4,870,953 A | 10/1989 | DonMicheal et al. | |
| 4,878,495 A | 11/1989 | Grayzel | |
| 4,898,575 A | 2/1990 | Fischell et al. | |
| 4,909,252 A | 3/1990 | Goldberger | |
| 4,919,133 A | 4/1990 | Chiang | |
| 4,920,954 A | 5/1990 | Alliger et al. | |
| 4,936,281 A | 6/1990 | Stasz | |
| 4,960,411 A | 10/1990 | Buchbinder | |
| 4,986,830 A | 1/1991 | Owens et al. | |
| 4,990,134 A | 2/1991 | Auth | |
| 5,058,570 A | 10/1991 | Idemoto et al. | |
| 5,069,664 A | 12/1991 | Guess et al. | |
| 5,076,276 A | 12/1991 | Sakurai et al. | |
| 5,106,302 A | 4/1992 | Farzin-nia et al. | |
| 5,248,296 A | 9/1993 | Alliger | |
| 5,267,954 A | 12/1993 | Nita | |
| 5,269,291 A | 12/1993 | Carter | |
| 5,295,958 A | 3/1994 | Shturman | |
| 5,304,115 A | 4/1994 | Pflueger et al. | |
| 5,314,407 A | 5/1994 | Auth et al. | |
| 5,318,014 A | 6/1994 | Carter | |
| 5,332,402 A | 7/1994 | Teitelbaum | |
| 5,344,426 A | 9/1994 | Lau et al. | |
| 5,352,199 A | 10/1994 | Tower | |
| 5,356,418 A | 10/1994 | Shturman | |
| 5,397,293 A | 3/1995 | Alliger et al. | |
| 5,411,552 A | 5/1995 | Andersen et al. | |
| 5,443,446 A | 8/1995 | Shturman | |
| 5,449,373 A | 9/1995 | Pinchasik et al. | |
| 5,489,297 A | 2/1996 | Duran | |
| 5,584,879 A | 12/1996 | Reimold et al. | |
| 5,609,151 A | 3/1997 | Mulier et al. | |
| 5,626,603 A | 5/1997 | Venturelli et al. | |
| 5,656,036 A | 8/1997 | Palmaz | |
| 5,662,671 A | 9/1997 | Barbut et al. | |
| 5,681,336 A | 10/1997 | Clement et al. | |
| 5,695,507 A | 12/1997 | Auth et al. | |
| 5,725,494 A | 3/1998 | Brisken | |
| 5,782,931 A | 7/1998 | Yang et al. | |
| 5,817,101 A | 10/1998 | Fiedler | |
| 5,827,229 A | 10/1998 | Auth et al. | |
| 5,827,321 A | 10/1998 | Roubin et al. | |
| 5,840,081 A | 11/1998 | Andersen et al. | |
| 5,853,422 A | 12/1998 | Huebsch et al. | |
| 5,855,601 A | 1/1999 | Bessler et al. | |
| 5,868,781 A | 2/1999 | Killion | |
| 5,873,811 A | 2/1999 | Wang et al. | |
| 5,904,679 A | 5/1999 | Clayman | |
| 5,957,882 A | 9/1999 | Nita et al. | |
| 5,972,004 A | 10/1999 | Williamson, IV et al. | |
| 5,989,208 A | 11/1999 | Nita | |
| 5,989,280 A | 11/1999 | Euteneuer et al. | |
| 6,047,700 A | 4/2000 | Eggers et al. | |
| 6,056,759 A | 5/2000 | Fiedler | |
| 6,085,754 A | 7/2000 | Alferness et al. | |
| 6,113,608 A | 9/2000 | Monroe et al. | |
| RE36,939 E | 10/2000 | Tachibarta et al. | |
| 6,129,734 A | 10/2000 | Shturman et al. | |
| 6,132,444 A | 10/2000 | Shturman et al. | |
| 6,168,579 B1 | 1/2001 | Tsugita | |
| 6,217,595 B1 | 4/2001 | Shturman et al. | |
| 6,254,635 B1 | 7/2001 | Schroeder et al. | |
| 6,295,712 B1 | 10/2001 | Shturman et al. | |
| 6,306,414 B1 | 10/2001 | Koike | |
| 6,321,109 B2 | 11/2001 | Ben-haim et al. | |
| 6,402,679 B1 | 6/2002 | Mortier et al. | |
| 6,423,032 B2 | 7/2002 | Parodi | |
| 6,425,916 B1 | 7/2002 | Garrison et al. | |
| 6,440,164 B1 | 8/2002 | DiMatteo et al. | |
| 6,454,737 B1 | 9/2002 | Nita et al. | |
| 6,454,757 B1 | 9/2002 | Nita et al. | |
| 6,454,799 B1 | 9/2002 | Schreck | |
| 6,458,153 B1 | 10/2002 | Bailey et al. | |
| 6,461,382 B1 | 10/2002 | Cao | |
| 6,494,691 B2 | 12/2002 | Cornish et al. | |
| 6,505,080 B1 | 1/2003 | Sutton | |
| 6,530,952 B2 | 3/2003 | Vesely | |
| 6,540,782 B1 | 4/2003 | Snyders | |
| 6,562,067 B2 | 5/2003 | Mathis | |
| 6,565,588 B1 | 5/2003 | Clement et al. | |
| 6,569,196 B1 | 5/2003 | Vesely | |
| 6,579,308 B1 | 6/2003 | Jansen et al. | |
| 6,582,462 B1 | 6/2003 | Andersen et al. | |
| 6,595,912 B2 | 7/2003 | Lau et al. | |
| 6,605,109 B2 | 8/2003 | Fiedler | |
| 6,616,689 B1 | 9/2003 | Ainsworth et al. | |
| 6,623,452 B2 | 9/2003 | Chien et al. | |
| 6,638,288 B1 | 10/2003 | Shturman et al. | |
| 6,648,854 B1 | 11/2003 | Patterson et al. | |
| 6,689,086 B1 | 2/2004 | Nita et al. | |
| 6,702,748 B1 | 3/2004 | Nita et al. | |
| 6,730,121 B2 | 5/2004 | Ortiz et al. | |
| 6,746,463 B1 | 6/2004 | Schwartz | |
| 6,811,801 B2 | 11/2004 | Nguyen et al. | |
| 6,818,001 B2 | 11/2004 | Wulfman et al. | |
| 6,843,797 B2 | 1/2005 | Nash et al. | |
| 6,852,118 B2 | 2/2005 | Shturman et al. | |
| 6,855,123 B2 | 2/2005 | Nita | |
| 6,869,439 B2 | 3/2005 | White et al. | |
| 6,951,571 B1 | 10/2005 | Srivastava | |
| 6,986,775 B2 | 1/2006 | Morales et al. | |
| 7,018,404 B2 | 3/2006 | Holmberg et al. | |
| 7,052,487 B2 | 5/2006 | Cohn et al. | |
| 7,077,861 B2 | 7/2006 | Spence | |
| 7,125,420 B2 | 10/2006 | Rourke et al. | |
| 7,186,264 B2 | 3/2007 | Liddicoat et al. | |
| 7,261,732 B2 | 8/2007 | Justino | |
| 7,296,577 B2 | 11/2007 | Lashinski et al. | |
| 7,381,218 B2 | 6/2008 | Schreck | |
| 7,404,824 B1 | 7/2008 | Webler et al. | |
| 7,442,204 B2 | 10/2008 | Schwarnmenthal et al. | |
| 7,473,275 B2 | 1/2009 | Marquez | |
| 7,510,575 B2 | 3/2009 | Spenser et al. | |
| 7,585,321 B2 | 9/2009 | Cribier | |
| 7,588,582 B2 | 9/2009 | Starksen et al. | |
| 7,621,948 B2 | 11/2009 | Herrmann et al. | |
| 7,708,775 B2 | 5/2010 | Rowe et al. | |
| 7,748,389 B2 | 7/2010 | Salahieh et al. | |
| 7,753,922 B2 | 7/2010 | Starksen | |
| 7,753,949 B2 | 7/2010 | Lamphere et al. | |
| 7,803,168 B2 | 9/2010 | Gifford et al. | |
| 7,857,845 B2 | 12/2010 | Stacchino et al. | |
| 7,896,915 B2 | 3/2011 | Guyenot et al. | |
| 7,942,928 B2 | 5/2011 | Webler et al. | |

(56) References Cited

U.S. PATENT DOCUMENTS

| | | |
|---|---|---|
| 8,002,826 B2 | 8/2011 | Seguin |
| 8,052,750 B2 | 11/2011 | Tuval et al. |
| 8,062,355 B2 | 11/2011 | Figulla et al. |
| 8,109,996 B2 | 2/2012 | Stacchino et al. |
| 8,114,154 B2 | 2/2012 | Righini et al. |
| 8,252,051 B2 | 8/2012 | Chau et al. |
| 8,398,704 B2 | 3/2013 | Straubinger et al. |
| 8,403,981 B2 | 3/2013 | Forster et al. |
| 8,403,983 B2 | 3/2013 | Quadri et al. |
| 8,414,643 B2 | 4/2013 | Tuval et al. |
| 8,449,599 B2 | 5/2013 | Chau et al. |
| 8,496,671 B1 | 7/2013 | Hausen |
| 8,512,252 B2 | 8/2013 | Ludomirsky et al. |
| 8,518,107 B2 | 8/2013 | Tsukashima et al. |
| 8,523,883 B2 | 9/2013 | Saadat |
| 8,532,352 B2 | 9/2013 | Ionasec et al. |
| 8,540,767 B2 | 9/2013 | Zhang |
| 8,545,551 B2 | 10/2013 | Loulmet |
| 8,551,161 B2 | 10/2013 | Dolan |
| 8,579,788 B2 | 11/2013 | Orejola |
| 8,579,964 B2 | 11/2013 | Lane et al. |
| 8,585,755 B2 | 11/2013 | Chau et al. |
| 8,597,347 B2 | 12/2013 | Maurer et al. |
| 8,597,348 B2 | 12/2013 | Rowe et al. |
| 8,608,796 B2 | 12/2013 | Matheny |
| 8,608,797 B2 | 12/2013 | Gross et al. |
| 8,623,077 B2 | 1/2014 | Cohn |
| 8,628,566 B2 | 1/2014 | Eberhardt et al. |
| 8,632,585 B2 | 1/2014 | Seguin et al. |
| 8,632,586 B2 | 1/2014 | Spenser et al. |
| 8,634,935 B2 | 1/2014 | Gaudiani |
| 8,647,254 B2 | 2/2014 | Callas et al. |
| 8,652,203 B2 | 2/2014 | Quadri et al. |
| 8,652,204 B2 | 2/2014 | Quill et al. |
| 8,657,872 B2 | 2/2014 | Seguin |
| 8,672,998 B2 | 3/2014 | Lichtenstein et al. |
| 8,673,001 B2 | 3/2014 | Cartledge et al. |
| 8,679,176 B2 | 3/2014 | Matheny |
| 8,685,086 B2 | 4/2014 | Navia et al. |
| 8,688,234 B2 | 4/2014 | Zhu et al. |
| 8,690,858 B2 | 4/2014 | Machold et al. |
| 8,709,074 B2 | 4/2014 | Solem et al. |
| 8,712,133 B2 | 4/2014 | Guhring et al. |
| 8,715,160 B2 | 5/2014 | Raman et al. |
| 8,721,665 B2 | 5/2014 | Oz et al. |
| 8,721,718 B2 | 5/2014 | Kassab |
| 8,740,918 B2 | 6/2014 | Seguin |
| 8,747,460 B2 | 6/2014 | Tuval et al. |
| 8,758,431 B2 | 6/2014 | Orlov et al. |
| 8,758,432 B2 | 6/2014 | Solem |
| 8,771,292 B2 | 7/2014 | Allen et al. |
| 8,771,345 B2 | 7/2014 | Tuval et al. |
| 8,771,346 B2 | 7/2014 | Tuval et al. |
| 8,777,991 B2 | 7/2014 | Zarbatany et al. |
| 8,778,016 B2 | 7/2014 | Janovsky et al. |
| 8,781,580 B2 | 7/2014 | Hedberg et al. |
| 8,784,482 B2 | 7/2014 | Rahdert et al. |
| 8,792,699 B2 | 7/2014 | Guetter et al. |
| 8,795,356 B2 | 8/2014 | Quadri et al. |
| 8,801,779 B2 | 8/2014 | Seguin et al. |
| 8,808,356 B2 | 8/2014 | Braido et al. |
| 8,808,366 B2 | 8/2014 | Braido et al. |
| 8,812,431 B2 | 8/2014 | Voigt et al. |
| 8,828,043 B2 | 9/2014 | Chambers |
| 8,845,717 B2 | 9/2014 | Khairkhahan et al. |
| 8,845,723 B2 | 9/2014 | Spence et al. |
| 8,852,213 B2 | 10/2014 | Gammie et al. |
| 8,852,272 B2 | 10/2014 | Gross et al. |
| 8,858,622 B2 | 10/2014 | Machold et al. |
| 8,859,724 B2 | 10/2014 | Meier et al. |
| 8,864,822 B2 | 10/2014 | Spence et al. |
| 8,870,936 B2 | 10/2014 | Rowe |
| 8,870,948 B1 | 10/2014 | Erzberger et al. |
| 8,870,949 B2 | 10/2014 | Rowe |
| 8,894,702 B2 | 11/2014 | Quadri et al. |
| 8,900,295 B2 | 12/2014 | Migliazza et al. |
| 8,926,694 B2 | 1/2015 | Costello |
| 8,932,348 B2 | 1/2015 | Solem et al. |
| 8,951,285 B2 | 2/2015 | Sugimoto et al. |
| 8,961,597 B2 | 2/2015 | Subramanian et al. |
| 8,968,393 B2 | 3/2015 | Rothstein |
| 8,968,395 B2 | 3/2015 | Hauser et al. |
| 8,974,445 B2 | 3/2015 | Warnking et al. |
| 8,979,922 B2 | 3/2015 | Jayasinghe et al. |
| 8,979,923 B2 | 3/2015 | Spence et al. |
| 8,986,370 B2 | 3/2015 | Annest |
| 8,986,376 B2 | 3/2015 | Solem |
| 8,992,604 B2 | 3/2015 | Gross et al. |
| 9,011,522 B2 | 4/2015 | Annest |
| 9,011,523 B2 | 4/2015 | Seguin |
| 9,017,399 B2 | 4/2015 | Gross et al. |
| 9,023,098 B2 | 5/2015 | Kuehn |
| 9,023,100 B2 | 5/2015 | Quadri et al. |
| 9,050,188 B2 | 6/2015 | Schweich, Jr. et al. |
| 9,066,800 B2 | 6/2015 | Clague et al. |
| 9,084,676 B2 | 7/2015 | Chau et al. |
| 9,095,433 B2 | 8/2015 | Lutter et al. |
| 9,119,713 B2 | 9/2015 | Board et al. |
| 9,132,009 B2 | 9/2015 | Hacohen et al. |
| 9,138,312 B2 | 9/2015 | Tuval et al. |
| 9,138,313 B2 | 9/2015 | McGuckinm, Jr. et al. |
| 9,180,005 B1 | 11/2015 | Lashinski et al. |
| 9,192,466 B2 | 11/2015 | Kovasky et al. |
| 9,192,471 B2 | 11/2015 | Bolling |
| 9,232,942 B2 | 1/2016 | Seguin et al. |
| 9,232,999 B2 | 1/2016 | Maurer et al. |
| 9,241,790 B2 | 1/2016 | Lane et al. |
| 9,248,014 B2 | 2/2016 | Lane et al. |
| 9,254,192 B2 | 2/2016 | Lutter et al. |
| 9,271,633 B2 | 3/2016 | Kim et al. |
| 9,289,291 B2 | 3/2016 | Gorman, III et al. |
| 9,289,297 B2 | 3/2016 | Wilson et al. |
| 9,295,547 B2 | 3/2016 | Costello et al. |
| 9,301,836 B2 | 4/2016 | Buchbinder et al. |
| 9,308,087 B2 | 4/2016 | Lane et al. |
| 9,326,850 B2 | 5/2016 | Venkatasubramanian |
| 9,339,378 B2 | 5/2016 | Quadri et al. |
| 9,339,379 B2 | 5/2016 | Quadri et al. |
| 9,339,380 B2 | 5/2016 | Quadri et al. |
| 9,339,382 B2 | 5/2016 | Tabor et al. |
| 9,358,108 B2 | 6/2016 | Bortlein et al. |
| 9,387,075 B2 | 7/2016 | Bortlein et al. |
| 9,387,078 B2 | 7/2016 | Gross et al. |
| 9,393,111 B2 | 7/2016 | Ma et al. |
| 9,629,719 B2 | 4/2017 | Rothstein et al. |
| 9,681,951 B2 | 6/2017 | Ratz et al. |
| 9,687,342 B2 | 6/2017 | Figulla et al. |
| 9,687,343 B2 | 6/2017 | Bortlein et al. |
| 9,693,859 B2 | 7/2017 | Braido et al. |
| 9,693,862 B2 | 7/2017 | Campbell et al. |
| 9,694,121 B2 | 7/2017 | Alexander et al. |
| 9,700,409 B2 | 7/2017 | Braido et al. |
| 9,700,411 B2 | 7/2017 | Klima et al. |
| 9,730,791 B2 | 8/2017 | Ratz et al. |
| 9,730,794 B2 | 8/2017 | Carpentier et al. |
| 9,750,605 B2 | 9/2017 | Ganesan et al. |
| 9,750,606 B2 | 9/2017 | Ganesan et al. |
| 9,750,607 B2 | 9/2017 | Ganesan et al. |
| 9,763,657 B2 | 9/2017 | Hacohen et al. |
| 9,763,658 B2 | 9/2017 | Eigler et al. |
| 9,763,782 B2 | 9/2017 | Solem et al. |
| 9,770,328 B2 | 9/2017 | Macoviak et al. |
| 9,827,092 B2 | 11/2017 | Vidlund et al. |
| 9,827,101 B2 | 11/2017 | Solem et al. |
| 9,833,313 B2 | 12/2017 | Board et al. |
| 9,833,315 B2 | 12/2017 | Vidlund et al. |
| 9,839,511 B2 | 12/2017 | Ma et al. |
| 9,844,435 B2 | 12/2017 | Eidenschink |
| 9,848,880 B2 | 12/2017 | Coleman et al. |
| 9,848,983 B2 | 12/2017 | Lashinski et al. |
| 9,861,477 B2 | 1/2018 | Backus et al. |
| 9,861,480 B2 | 1/2018 | Zakai et al. |
| 2001/0021872 A1 | 9/2001 | Bailey et al. |
| 2001/0049492 A1 | 12/2001 | Frazier et al. |

(56) References Cited

U.S. PATENT DOCUMENTS

| | | |
|---|---|---|
| 2002/0007219 A1 | 1/2002 | Merrill et al. |
| 2002/0013571 A1 | 1/2002 | Goldfarb et al. |
| 2002/0072792 A1 | 6/2002 | Burgermeister et al. |
| 2002/0082637 A1 | 6/2002 | Lumauig |
| 2002/0099439 A1 | 7/2002 | Schwartz et al. |
| 2002/0138138 A1 | 9/2002 | Yang |
| 2002/0151970 A1 | 10/2002 | Garrison et al. |
| 2002/0173841 A1 | 11/2002 | Ortiz et al. |
| 2003/0120340 A1 | 6/2003 | Liska et al. |
| 2003/0139689 A1 | 7/2003 | Shturman et al. |
| 2004/0006358 A1 | 1/2004 | Wulfman et al. |
| 2004/0039412 A1 | 2/2004 | Isshiki et al. |
| 2004/0044350 A1 | 3/2004 | Martin et al. |
| 2004/0057955 A1 | 3/2004 | O'Brien et al. |
| 2004/0082910 A1 | 4/2004 | Constantz et al. |
| 2004/0092858 A1 | 5/2004 | Wilson et al. |
| 2004/0092962 A1 | 5/2004 | Thornton et al. |
| 2004/0092989 A1 | 5/2004 | Wilson et al. |
| 2004/0106989 A1 | 6/2004 | Wilson et al. |
| 2004/0117009 A1 | 6/2004 | Cali et al. |
| 2004/0122510 A1 | 6/2004 | Sarac |
| 2004/0127979 A1 | 7/2004 | Wilson et al. |
| 2004/0127982 A1 | 7/2004 | Machold et al. |
| 2004/0186558 A1 | 9/2004 | Pavcnik et al. |
| 2004/0199191 A1 | 10/2004 | Schwartz |
| 2004/0230117 A1 | 11/2004 | Tosaya et al. |
| 2004/0230212 A1 | 11/2004 | Wulfman |
| 2004/0230213 A1 | 11/2004 | Wulfman |
| 2004/0243162 A1 | 11/2004 | Wulfman |
| 2005/0007219 A1 | 1/2005 | Ma et al. |
| 2005/0075662 A1 | 1/2005 | Ma et al. |
| 2005/0075720 A1 | 4/2005 | Pedersen et al. |
| 2005/0075727 A1 | 4/2005 | Wheatley |
| 2005/0137682 A1 | 4/2005 | Nguyen et al. |
| 2005/0107661 A1 | 5/2005 | Lau et al. |
| 2005/0137690 A1 | 6/2005 | Justino |
| 2005/0137691 A1 | 6/2005 | Salahieh et al. |
| 2005/0137695 A1 | 6/2005 | Salahieh et al. |
| 2005/0137697 A1 | 6/2005 | Salahieh et al. |
| 2005/0137698 A1 | 6/2005 | Salahieh et al. |
| 2005/0137700 A1 | 6/2005 | Spence et al. |
| 2005/0137701 A1 | 6/2005 | Spence et al. |
| 2005/0137702 A1 | 6/2005 | Haug et al. |
| 2005/0267523 A1 | 6/2005 | Salahieh et al. |
| 2006/0058872 A1 | 3/2006 | Salahieh et al. |
| 2006/0106456 A9 | 3/2006 | Salahieh et al. |
| 2006/0149360 A1 | 5/2006 | Machold et al. |
| 2006/0167543 A1 | 7/2006 | Bailey et al. |
| 2006/0195163 A1 | 7/2006 | Schwammenthal et al. |
| 2006/0253191 A1 | 8/2006 | Navia et al. |
| 2006/0287719 A1 | 11/2006 | Salahieh et al. |
| 2007/0056346 A1 | 3/2007 | Spenser et al. |
| 2007/0061010 A1 | 3/2007 | Hauser et al. |
| 2007/0073391 A1 | 3/2007 | Bourang et al. |
| 2007/0088431 A1 | 4/2007 | Bourang et al. |
| 2007/0142906 A1 | 6/2007 | Figulla et al. |
| 2007/0173932 A1 | 7/2007 | Cali et al. |
| 2008/0071369 A1 | 3/2008 | Tuval et al. |
| 2008/0082166 A1 | 4/2008 | Styrc et al. |
| 2008/0103586 A1 | 5/2008 | Styrc et al. |
| 2008/0140189 A1 | 6/2008 | Nguyen et al. |
| 2008/0208332 A1 | 8/2008 | Lamphere et al. |
| 2008/0221672 A1 | 9/2008 | Lamphere et al. |
| 2008/0234728 A1 | 9/2008 | Starksen et al. |
| 2008/0243245 A1 | 10/2008 | Thambar et al. |
| 2008/0243246 A1 | 10/2008 | Ryan et al. |
| 2009/0054969 A1 | 2/2009 | Salahieh et al. |
| 2009/0076586 A1 | 3/2009 | Hauser et al. |
| 2009/0076598 A1 | 3/2009 | Salahieh et al. |
| 2009/0093670 A1 | 4/2009 | Annest et al. |
| 2009/0157174 A1 | 6/2009 | Yoganathan et al. |
| 2009/0164006 A1 | 6/2009 | Seguin et al. |
| 2009/0198315 A1 | 8/2009 | Boudjemline |
| 2009/0216312 A1 | 8/2009 | Straubinger et al. |
| 2009/0240320 A1 | 9/2009 | Tuval et al. |
| 2009/0259292 A1 | 10/2009 | Bonhoeffer |
| 2009/0259306 A1 | 10/2009 | Rowe |
| 2009/0264997 A1 | 10/2009 | Salahieh et al. |
| 2009/0276040 A1 | 11/2009 | Rowe et al. |
| 2009/0281609 A1 | 11/2009 | Benichou et al. |
| 2009/0281618 A1 | 11/2009 | Hill et al. |
| 2009/0292350 A1 | 11/2009 | Eberhardt et al. |
| 2009/0306768 A1 | 12/2009 | Quadri |
| 2009/0319037 A1 | 12/2009 | Rowe et al. |
| 2009/0319038 A1 | 12/2009 | Gurskis et al. |
| 2010/0016958 A1 | 1/2010 | St. Goar et al. |
| 2010/0023117 A1 | 1/2010 | Yoganathan et al. |
| 2010/0030330 A1 | 2/2010 | Bobo et al. |
| 2010/0049313 A1 | 2/2010 | Alon et al. |
| 2010/0076548 A1 | 3/2010 | Konno |
| 2010/0082094 A1 | 4/2010 | Quadri et al. |
| 2010/0094411 A1 | 4/2010 | Tuval et al. |
| 2010/0121436 A1 | 5/2010 | Tuval et al. |
| 2010/0185275 A1 | 7/2010 | Richter et al. |
| 2010/0217382 A1 | 8/2010 | Chau et al. |
| 2010/0249915 A1 | 9/2010 | Zhang |
| 2010/0249923 A1 | 9/2010 | Alkhatib et al. |
| 2010/0298929 A1 | 11/2010 | Thornton et al. |
| 2010/0298931 A1 | 11/2010 | Quadri et al. |
| 2010/0312333 A1 | 12/2010 | Navia et al. |
| 2010/0324554 A1 | 12/2010 | Gifford et al. |
| 2011/0004296 A1 | 1/2011 | Lutter et al. |
| 2011/0015722 A1 | 1/2011 | Hauser et al. |
| 2011/0022166 A1 | 1/2011 | Dahlgren et al. |
| 2011/0029071 A1 | 2/2011 | Zlotnick et al. |
| 2011/0029072 A1 | 2/2011 | Gabbay |
| 2011/0040374 A1 | 2/2011 | Goetz et al. |
| 2011/0040375 A1 | 2/2011 | Letac et al. |
| 2011/0066231 A1 | 3/2011 | Cartledge et al. |
| 2011/0066233 A1 | 3/2011 | Thornton et al. |
| 2011/0112632 A1 | 5/2011 | Chau et al. |
| 2011/0137397 A1 | 6/2011 | Chau et al. |
| 2011/0137409 A1 | 6/2011 | Yang et al. |
| 2011/0137410 A1 | 6/2011 | Hacohen |
| 2011/0153008 A1 | 6/2011 | Marchand et al. |
| 2011/0172784 A1 | 7/2011 | Richter et al. |
| 2011/0184512 A1 | 7/2011 | Webler et al. |
| 2011/0208293 A1 | 8/2011 | Tabor |
| 2011/0224785 A1 | 9/2011 | Hacohen |
| 2011/0319988 A1 | 12/2011 | Schankereli et al. |
| 2012/0022639 A1 | 1/2012 | Hacohen et al. |
| 2012/0035703 A1 | 2/2012 | Lutter et al. |
| 2012/0035713 A1 | 2/2012 | Lutter et al. |
| 2012/0053680 A1 | 3/2012 | Bolling et al. |
| 2012/0053682 A1 | 3/2012 | Kovalsky et al. |
| 2012/0078347 A1 | 3/2012 | Braido et al. |
| 2012/0078360 A1 | 3/2012 | Rafiee |
| 2012/0101571 A1 | 4/2012 | Thambar et al. |
| 2012/0165930 A1 | 6/2012 | Gifford, III et al. |
| 2012/0179239 A1 | 7/2012 | Quadri |
| 2012/0179244 A1 | 7/2012 | Schankereli et al. |
| 2012/0203336 A1 | 8/2012 | Annest |
| 2012/0283824 A1 | 11/2012 | Lutter et al. |
| 2013/0172978 A1 | 7/2013 | Vidlund et al. |
| 2013/0190860 A1 | 7/2013 | Sundt, III |
| 2013/0190861 A1 | 7/2013 | Chau et al. |
| 2013/0197354 A1 | 8/2013 | Maschke et al. |
| 2013/0197630 A1 | 8/2013 | Azarnoush |
| 2013/0204356 A1 | 8/2013 | Dwork et al. |
| 2013/0204358 A1 | 8/2013 | Matheny |
| 2013/0226289 A1 | 8/2013 | Shaolian et al. |
| 2013/0226290 A1 | 8/2013 | Yellin et al. |
| 2013/0231735 A1 | 9/2013 | Deem et al. |
| 2013/0238089 A1 | 9/2013 | Lichtenstein et al. |
| 2013/0244927 A1 | 9/2013 | Lal et al. |
| 2013/0253641 A1 | 9/2013 | Lattouf |
| 2013/0253642 A1 | 9/2013 | Brecker |
| 2013/0253643 A1 | 9/2013 | Rolando et al. |
| 2013/0259337 A1 | 10/2013 | Guhring et al. |
| 2013/0261737 A1 | 10/2013 | Costello |
| 2013/0261738 A1 | 10/2013 | Calgue et al. |
| 2013/0261739 A1 | 10/2013 | Kuehn |
| 2013/0261741 A1 | 10/2013 | Accola |
| 2013/0268066 A1 | 10/2013 | Rowe |

(56) References Cited

U.S. PATENT DOCUMENTS

| | | |
|---|---|---|
| 2013/0274870 A1 | 10/2013 | Lombardi et al. |
| 2013/0282059 A1 | 10/2013 | Ketai et al. |
| 2013/0282060 A1 | 10/2013 | Tuval |
| 2013/0282110 A1 | 10/2013 | Schweich, Jr. et al. |
| 2013/0289642 A1 | 10/2013 | Hedberg et al. |
| 2013/0289717 A1 | 10/2013 | Solem |
| 2013/0289718 A1 | 10/2013 | Tsukashima et al. |
| 2013/0296851 A1 | 11/2013 | Boronyak et al. |
| 2013/0296999 A1 | 11/2013 | Burriesci et al. |
| 2013/0304180 A1 | 11/2013 | Green et al. |
| 2013/0304181 A1 | 11/2013 | Green et al. |
| 2013/0304197 A1 | 11/2013 | Buchbinder et al. |
| 2013/0304198 A1 | 11/2013 | Solem |
| 2013/0304200 A1 | 11/2013 | McLean et al. |
| 2013/0309292 A1 | 11/2013 | Andersen |
| 2013/0310436 A1 | 11/2013 | Lowes et al. |
| 2013/0310925 A1 | 11/2013 | Eliasen et al. |
| 2013/0310928 A1 | 11/2013 | Morriss et al. |
| 2013/0317603 A1 | 11/2013 | McLean et al. |
| 2013/0325110 A1 | 12/2013 | Khalil et al. |
| 2013/0325114 A1 | 12/2013 | McLean et al. |
| 2013/0331864 A1 | 12/2013 | Jelich et al. |
| 2013/0338684 A1 | 12/2013 | Hausen |
| 2013/0338763 A1 | 12/2013 | Rowe et al. |
| 2013/0345797 A1 | 12/2013 | Dahlgren et al. |
| 2013/0345803 A1 | 12/2013 | Bergheim, III |
| 2014/0005778 A1 | 1/2014 | Buchbinder et al. |
| 2014/0018906 A1 | 1/2014 | Rafiee |
| 2014/0018913 A1 | 1/2014 | Cartledge et al. |
| 2014/0023261 A1 | 1/2014 | Watanabe et al. |
| 2014/0025164 A1 | 1/2014 | Montorfano et al. |
| 2014/0031928 A1 | 1/2014 | Murphy et al. |
| 2014/0046219 A1 | 2/2014 | Sauter et al. |
| 2014/0046436 A1 | 2/2014 | Kheradvar |
| 2014/0052237 A1 | 2/2014 | Lane et al. |
| 2014/0052240 A1 | 2/2014 | Zhang |
| 2014/0056906 A1 | 2/2014 | Yue et al. |
| 2014/0066895 A1 | 3/2014 | Kipperman |
| 2014/0067048 A1 | 3/2014 | Chau et al. |
| 2014/0067052 A1 | 3/2014 | Chau et al. |
| 2014/0067054 A1 | 3/2014 | Chau et al. |
| 2014/0088071 A1 | 3/2014 | Nakai et al. |
| 2014/0088680 A1 | 3/2014 | Costello et al. |
| 2014/0088693 A1 | 3/2014 | Seguin et al. |
| 2014/0088695 A1 | 3/2014 | Figulla et al. |
| 2014/0128965 A1 | 3/2014 | Figulla et al. |
| 2014/0094906 A1 | 4/2014 | Spence et al. |
| 2014/0107775 A1 | 4/2014 | Hjelle et al. |
| 2014/0114404 A1 | 4/2014 | Gammie et al. |
| 2014/0114407 A1 | 4/2014 | Rajamannan |
| 2014/0135913 A1 | 4/2014 | Spence et al. |
| 2014/0163652 A1 | 4/2014 | Hjelle et al. |
| 2014/0163668 A1 | 4/2014 | Gammie et al. |
| 2014/0172076 A1 | 4/2014 | Rajamannan |
| 2014/0121763 A1 | 5/2014 | Duffy et al. |
| 2014/0172084 A1 | 5/2014 | Duffy et al. |
| 2014/0172085 A1 | 5/2014 | Rafiee |
| 2014/0172086 A1 | 5/2014 | Lichtenstein et al. |
| 2014/0179993 A1 | 6/2014 | Witzel et al. |
| 2014/0180401 A1 | 6/2014 | Rafiee |
| 2014/0188108 A1 | 6/2014 | Jonsson et al. |
| 2014/0188215 A1 | 6/2014 | Callas et al. |
| 2014/0194920 A1 | 6/2014 | Quadri et al. |
| 2014/0194976 A1 | 6/2014 | Quadri et al. |
| 2014/0200397 A1 | 6/2014 | Alexander et al. |
| 2014/0200649 A1 | 6/2014 | Quill et al. |
| 2014/0200657 A1 | 7/2014 | Goodine et al. |
| 2014/0200662 A1 | 7/2014 | Hlavka et al. |
| 2014/0214159 A1 | 7/2014 | Krahbichler |
| 2014/0219524 A1 | 7/2014 | Starksen et al. |
| 2014/0222040 A1 | 7/2014 | Raman et al. |
| 2014/0222138 A1 | 7/2014 | Essinger et al. |
| 2014/0228942 A1 | 7/2014 | Maurer et al. |
| 2014/0228946 A1 | 7/2014 | Eftel et al. |
| 2014/0242086 A1 | 8/2014 | Lal et al. |
| 2014/0243860 A1 | 8/2014 | Morris et al. |
| 2014/0243954 A1 | 8/2014 | Shannon |
| 2014/0243964 A1 | 8/2014 | Venkatasubramanian |
| 2014/0249621 A1 | 9/2014 | Eidenschink |
| 2014/0257101 A1 | 9/2014 | Gaudiani |
| 2014/0257466 A1 | 9/2014 | Board et al. |
| 2014/0257467 A1 | 9/2014 | Lane et al. |
| 2014/0257473 A1 | 9/2014 | Rajamannan |
| 2014/0257475 A1 | 9/2014 | Gross et al. |
| 2014/0275757 A1 | 9/2014 | Goodwin et al. |
| 2014/0276395 A1 | 9/2014 | Wilson et al. |
| 2014/0276609 A1 | 9/2014 | Magee et al. |
| 2014/0276762 A1 | 9/2014 | Paskar |
| 2014/0276971 A1 | 9/2014 | Kovach |
| 2014/0277119 A1 | 9/2014 | Akpinar |
| 2014/0277390 A1 | 9/2014 | Ratz et al. |
| 2014/0277404 A1 | 9/2014 | Wilson et al. |
| 2014/0277405 A1 | 9/2014 | Wilson et al. |
| 2014/0277406 A1 | 9/2014 | Arcidi |
| 2014/0277407 A1 | 9/2014 | Dale et al. |
| 2014/0277408 A1 | 9/2014 | Folan |
| 2014/0277409 A1 | 9/2014 | Bortlein et al. |
| 2014/0277410 A1 | 9/2014 | Bortlein et al. |
| 2014/0277411 A1 | 9/2014 | Bortlein et al. |
| 2014/0277412 A1 | 9/2014 | Bortlein et al. |
| 2014/0277420 A1 | 9/2014 | Migliazza et al. |
| 2014/0277422 A1 | 9/2014 | Ratz et al. |
| 2014/0288480 A1 | 9/2014 | Zimmerman et al. |
| 2014/0296878 A1 | 10/2014 | Oz et al. |
| 2014/0296969 A1 | 10/2014 | Tegels et al. |
| 2014/0296970 A1 | 10/2014 | Ekvall et al. |
| 2014/0296971 A1 | 10/2014 | Tegels et al. |
| 2014/0296975 A1 | 10/2014 | Tegels et al. |
| 2014/0303719 A1 | 10/2014 | Cox et al. |
| 2014/0303721 A1 | 10/2014 | Fung et al. |
| 2014/0309727 A1 | 10/2014 | Lameias et al. |
| 2014/0309730 A1 | 10/2014 | Alon et al. |
| 2014/0309731 A1 | 10/2014 | Quadri et al. |
| 2014/0309732 A1 | 10/2014 | Solem |
| 2014/0316516 A1 | 10/2014 | Vidlund et al. |
| 2014/0324164 A1 | 10/2014 | Gross et al. |
| 2014/0358222 A1 | 12/2014 | Gorman, III et al. |
| 2014/0358224 A1 | 12/2014 | Tegels et al. |
| 2014/0364944 A1 | 12/2014 | Lutter et al. |
| 2014/0371643 A1 | 12/2014 | Wilson; et al. |
| 2014/0371646 A1 | 12/2014 | Wilson et al. |
| 2014/0371844 A1 | 12/2014 | Dale et al. |
| 2014/0379074 A1 | 12/2014 | Spence et al. |
| 2014/0379076 A1 | 12/2014 | Vidlund et al. |
| 2015/0005874 A1 | 1/2015 | Vidlund et al. |
| 2015/0005875 A1 | 1/2015 | Tuval et al. |
| 2015/0025623 A1 | 1/2015 | Granada et al. |
| 2015/0032127 A1 | 1/2015 | Gammie et al. |
| 2015/0045878 A1 | 2/2015 | Rowe |
| 2015/0066140 A1 | 3/2015 | Quadri et al. |
| 2015/0094802 A1 | 4/2015 | Buchbinder et al. |
| 2015/0094803 A1* | 4/2015 | Navia ............... A61F 2/2445 623/2.36 |
| 2015/0100116 A1 | 4/2015 | Mohl et al. |
| 2015/0112427 A1 | 4/2015 | Schweich, Jr. et al. |
| 2015/0112429 A1 | 4/2015 | Khairkhahan et al. |
| 2015/0112433 A1 | 4/2015 | Schweich, Jr. et al. |
| 2015/0119978 A1 | 4/2015 | Tegels et al. |
| 2015/0119981 A1 | 4/2015 | Khairkhahan et al. |
| 2015/0119982 A1 | 4/2015 | Quill et al. |
| 2015/0127091 A1 | 5/2015 | Cecere et al. |
| 2015/0127096 A1 | 5/2015 | Rowe et al. |
| 2015/0142101 A1 | 5/2015 | Coleman et al. |
| 2015/0142103 A1 | 5/2015 | Vidlund |
| 2015/0142105 A1 | 5/2015 | Bolling et al. |
| 2015/0150678 A1 | 6/2015 | Brecker |
| 2015/0157458 A1 | 6/2015 | Thambar et al. |
| 2015/0157459 A1 | 6/2015 | Macoviak et al. |
| 2015/0164637 A1 | 6/2015 | Khairkhahan et al. |
| 2015/0164641 A1 | 6/2015 | Annest |
| 2015/0173697 A1 | 6/2015 | Raanani et al. |
| 2015/0173898 A1 | 6/2015 | Drasler et al. |
| 2015/0173900 A1 | 6/2015 | Hauser et al. |
| 2015/0190229 A1 | 7/2015 | Seguin |

(56) References Cited

U.S. PATENT DOCUMENTS

| | | |
|---|---|---|
| 2015/0196390 A1 | 7/2015 | Ma et al. |
| 2015/0196393 A1 | 7/2015 | Vidlund et al. |
| 2015/0202043 A1 | 7/2015 | Zakai et al. |
| 2015/0209137 A1 | 7/2015 | Quadri et al. |
| 2015/0209139 A1 | 7/2015 | Granada et al. |
| 2015/0216655 A1 | 8/2015 | Lane et al. |
| 2015/0216661 A1 | 8/2015 | Hacohen et al. |
| 2015/0223802 A1 | 8/2015 | Tegzes |
| 2015/0223934 A1 | 8/2015 | Vidlund et al. |
| 2015/0223935 A1 | 8/2015 | Subramanian et al. |
| 2015/0230920 A1 | 8/2015 | Alfieri et al. |
| 2015/0230921 A1 | 8/2015 | Chau et al. |
| 2015/0238312 A1 | 8/2015 | Lashinski |
| 2015/0238313 A1 | 8/2015 | Spence et al. |
| 2015/0250590 A1 | 9/2015 | Gries et al. |
| 2015/0257877 A1 | 9/2015 | Hernandez |
| 2015/0257878 A1 | 9/2015 | Lane et al. |
| 2015/0257879 A1 | 9/2015 | Bortlein et al. |
| 2015/0257881 A1 | 9/2015 | Bortlein et al. |
| 2015/0257882 A1 | 9/2015 | Bortlein et al. |
| 2015/0272737 A1 | 10/2015 | Dale et al. |
| 2015/0305861 A1 | 10/2015 | Annest |
| 2015/0305864 A1 | 10/2015 | Quadri et al. |
| 2015/0313739 A1 | 11/2015 | Hummen et al. |
| 2015/0320553 A1 | 11/2015 | Chau et al. |
| 2015/0327999 A1 | 11/2015 | Board et al. |
| 2015/0328000 A1 | 11/2015 | Ratz et al. |
| 2015/0342733 A1 | 12/2015 | Alkhatib et al. |
| 2015/0351906 A1 | 12/2015 | Hammer et al. |
| 2015/0351908 A1 | 12/2015 | Keranen et al. |
| 2015/0359628 A1 | 12/2015 | Keranen |
| 2015/0359629 A1 | 12/2015 | Ganesan et al. |
| 2015/0359631 A1 | 12/2015 | Sheehan et al. |
| 2015/0366666 A1 | 12/2015 | Khairkhahan et al. |
| 2015/0374495 A1 | 12/2015 | Ruyra Baliarda et al. |
| 2016/0000983 A1 | 1/2016 | Mohl et al. |
| 2016/0015513 A1 | 1/2016 | Lashinski et al. |
| 2016/0015514 A1 | 1/2016 | Lashinski et al. |
| 2016/0015515 A1 | 1/2016 | Lashinski et al. |
| 2016/0030171 A1 | 2/2016 | Quijano et al. |
| 2016/0038246 A1 | 2/2016 | Wang et al. |
| 2016/0038280 A1 | 2/2016 | Morriss et al. |
| 2016/0038283 A1 | 2/2016 | Divekar et al. |
| 2016/0038286 A1 | 2/2016 | Yellin et al. |
| 2016/0074160 A1 | 3/2016 | Christianson et al. |
| 2016/0106539 A1 | 4/2016 | Buchbinder et al. |
| 2016/0113764 A1 | 4/2016 | Sheahan et al. |
| 2016/0113765 A1 | 4/2016 | Ganesan et al. |
| 2016/0113766 A1 | 4/2016 | Ganesan et al. |
| 2016/0113768 A1 | 4/2016 | Ganesan et al. |
| 2016/0120643 A1 | 5/2016 | Kupumbati |
| 2016/0143730 A1 | 5/2016 | Kheradvar |
| 2016/0151154 A1 | 6/2016 | Gorman, III et al. |
| 2016/0151156 A1 | 6/2016 | Seguin et al. |
| 2016/0151552 A1 | 6/2016 | Solem |
| 2016/0157999 A1 | 6/2016 | Lane et al. |
| 2016/0158000 A1 | 6/2016 | Granada et al. |
| 2016/0158001 A1 | 6/2016 | Wallace et al. |
| 2016/0158002 A1 | 6/2016 | Wallace et al. |
| 2016/0158003 A1 | 6/2016 | Wallace et al. |
| 2016/0184095 A1 | 6/2016 | Spence et al. |
| 2016/0206280 A1 | 7/2016 | Vidlund et al. |
| 2016/0206424 A1 | 7/2016 | Al-Jilaihawi et al. |
| 2016/0262881 A1 | 9/2016 | Schankereli et al. |
| 2016/0317290 A1 | 11/2016 | Chau et al. |
| 2017/0079790 A1 | 3/2017 | Vidlund et al. |
| 2017/0100248 A1 | 4/2017 | Tegels et al. |
| 2017/0100250 A1 | 4/2017 | Marsot et al. |
| 2017/0119526 A1 | 5/2017 | Luong et al. |
| 2017/0128198 A1 | 5/2017 | Cartledge et al. |
| 2017/0128205 A1 | 5/2017 | Tamir et al. |
| 2017/0128206 A1 | 5/2017 | Rafiee et al. |
| 2017/0128208 A1 | 5/2017 | Christianson et al. |
| 2017/0156860 A1 | 6/2017 | Lashinski |
| 2017/0165054 A1 | 6/2017 | Benson et al. |
| 2017/0165055 A1 | 6/2017 | Hauser et al. |
| 2017/0172737 A1 | 6/2017 | Kuetting et al. |
| 2017/0181851 A1 | 6/2017 | Annest |
| 2017/0189179 A1 | 7/2017 | Ratz et al. |
| 2017/0189180 A1 | 7/2017 | Alkhatib |
| 2017/0189181 A1 | 7/2017 | Alkhatib et al. |
| 2017/0231762 A1 | 8/2017 | Quadri et al. |
| 2017/0231763 A1 | 8/2017 | Yellin et al. |
| 2017/0258585 A1 | 9/2017 | Marquez et al. |
| 2017/0266001 A1 | 9/2017 | Vidlund et al. |
| 2017/0281345 A1 | 10/2017 | Yang et al. |
| 2017/0290659 A1 | 10/2017 | Ulmer et al. |
| 2017/0296339 A1 | 10/2017 | Thambar et al. |
| 2017/0319333 A1 | 11/2017 | Tegels et al. |
| 2017/0325941 A1 | 11/2017 | Wallace et al. |
| 2017/0325945 A1 | 11/2017 | Dale et al. |
| 2017/0325948 A1 | 11/2017 | Wallace et al. |
| 2017/0333186 A1 | 11/2017 | Spargias |
| 2017/0333188 A1 | 11/2017 | Carpentier et al. |
| 2017/0340440 A1 | 11/2017 | Ratz et al. |
| 2017/0348098 A1 | 12/2017 | Rowe et al. |
| 2017/0348100 A1 | 12/2017 | Lane et al. |
| 2017/0354496 A1 | 12/2017 | Quadri et al. |
| 2017/0354497 A1 | 12/2017 | Quadri et al. |
| 2017/0354499 A1 | 12/2017 | Granada et al. |
| 2017/0360426 A1 | 12/2017 | Hacohen et al. |
| 2017/0360549 A1 | 12/2017 | Lashinski et al. |
| 2017/0360558 A1 | 12/2017 | Ma |
| 2017/0360585 A1 | 12/2017 | White |

FOREIGN PATENT DOCUMENTS

| | | |
|---|---|---|
| CN | 101291637 | 10/2008 |
| CN | 103491900 | 1/2014 |
| DE | 19605042 | 1/1998 |
| DE | 102006052564 | 12/2007 |
| EP | 0186104 | 7/1986 |
| EP | 1512383 | 3/2005 |
| EP | 1545371 | 6/2005 |
| EP | 1551274 | 7/2005 |
| EP | 1629794 | 3/2006 |
| EP | 1646332 | 4/2006 |
| EP | 1702247 | 9/2006 |
| EP | 1734903 | 12/2006 |
| EP | 1891914 | 2/2008 |
| EP | 2026280 | 2/2009 |
| EP | 2037829 | 3/2009 |
| EP | 2081519 | 7/2009 |
| EP | 2111190 | 10/2009 |
| EP | 2142143 | 1/2010 |
| EP | 2167742 | 3/2010 |
| EP | 2278944 | 2/2011 |
| EP | 2306821 | 4/2011 |
| EP | 2327429 | 6/2011 |
| EP | 2400924 | 1/2012 |
| EP | 2400926 | 1/2012 |
| EP | 2410947 | 2/2012 |
| EP | 2444031 | 4/2012 |
| EP | 2488126 | 8/2012 |
| EP | 2509538 | 10/2012 |
| EP | 2549955 | 1/2013 |
| EP | 2549956 | 1/2013 |
| EP | 2566416 | 3/2013 |
| EP | 2586492 | 5/2013 |
| EP | 2618784 | 7/2013 |
| EP | 2623066 | 8/2013 |
| EP | 2626013 | 8/2013 |
| EP | 2629699 | 8/2013 |
| EP | 2633457 | 9/2013 |
| EP | 2637659 | 9/2013 |
| EP | 2641569 | 9/2013 |
| EP | 2644158 | 10/2013 |
| EP | 2654624 | 10/2013 |
| EP | 2656794 | 10/2013 |
| EP | 2656795 | 10/2013 |
| EP | 2656796 | 10/2013 |
| EP | 2667823 | 12/2013 |
| EP | 2670358 | 12/2013 |
| EP | 2676640 | 12/2013 |

(56) References Cited

FOREIGN PATENT DOCUMENTS

| | | |
|---|---|---|
| EP | 2688041 | 1/2014 |
| EP | 2697721 | 2/2014 |
| EP | 2713953 | 4/2014 |
| EP | 2714068 | 4/2014 |
| EP | 2723272 | 4/2014 |
| EP | 2723273 | 4/2014 |
| EP | 2723277 | 4/2014 |
| EP | 2739214 | 6/2014 |
| EP | 2741711 | 6/2014 |
| EP | 2750630 | 7/2014 |
| EP | 2750631 | 7/2014 |
| EP | 2755562 | 7/2014 |
| EP | 2755602 | 7/2014 |
| EP | 2757962 | 7/2014 |
| EP | 2777616 | 9/2014 |
| EP | 2777617 | 9/2014 |
| EP | 2782523 | 10/2014 |
| EP | 2785282 | 10/2014 |
| EP | 2786817 | 10/2014 |
| EP | 2790609 | 10/2014 |
| EP | 2793751 | 10/2014 |
| EP | 2809263 | 12/2014 |
| EP | 2810620 | 12/2014 |
| EP | 2814428 | 12/2014 |
| EP | 2814429 | 12/2014 |
| EP | 2819617 | 1/2015 |
| EP | 2819618 | 1/2015 |
| EP | 2819619 | 1/2015 |
| EP | 2416739 | 2/2015 |
| EP | 2833836 | 2/2015 |
| EP | 2838475 | 2/2015 |
| EP | 2839815 | 2/2015 |
| EP | 2844190 | 3/2015 |
| EP | 2849680 | 3/2015 |
| EP | 2849681 | 3/2015 |
| EP | 2852354 | 4/2015 |
| EP | 2870933 | 5/2015 |
| EP | 2873011 | 5/2015 |
| EP | 2875797 | 5/2015 |
| EP | 2382374 | 6/2015 |
| EP | 2760375 | 6/2015 |
| EP | 2866084 | 6/2015 |
| EP | 2886082 | 6/2015 |
| EP | 2886083 | 6/2015 |
| EP | 2895111 | 7/2015 |
| EP | 2901966 | 8/2015 |
| EP | 2907479 | 8/2015 |
| EP | 2945572 | 11/2015 |
| EP | 2948094 | 12/2015 |
| EP | 2948102 | 12/2015 |
| EP | 2964152 | 1/2016 |
| EP | 2967859 | 1/2016 |
| EP | 2967860 | 1/2016 |
| EP | 2967866 | 1/2016 |
| EP | 2968847 | 1/2016 |
| EP | 2981208 | 2/2016 |
| EP | 2982336 | 2/2016 |
| EP | 2999433 | 3/2016 |
| EP | 3003187 | 4/2016 |
| EP | 3003219 | 4/2016 |
| EP | 3003220 | 4/2016 |
| EP | 3010447 | 4/2016 |
| EP | 3013281 | 5/2016 |
| EP | 3017792 | 5/2016 |
| EP | 3021792 | 5/2016 |
| EP | 3023117 | 5/2016 |
| EP | 3027143 | 6/2016 |
| EP | 3033048 | 6/2016 |
| EP | 3037064 | 6/2016 |
| EP | 3229736 | 11/2016 |
| EP | 2999436 | 5/2017 |
| EP | 3184081 | 6/2017 |
| EP | 3191027 | 7/2017 |
| EP | 2611389 | 8/2017 |
| EP | 3082656 | 8/2017 |
| EP | 3206628 | 8/2017 |
| EP | 2010103 | 9/2017 |
| EP | 2509538 | 9/2017 |
| EP | 3223751 | 10/2017 |
| EP | 3027144 | 11/2017 |
| EP | 3110368 | 11/2017 |
| EP | 3110369 | 11/2017 |
| EP | 3132773 | 11/2017 |
| EP | 3245980 | 11/2017 |
| EP | 3250154 | 12/2017 |
| EP | 3256077 | 12/2017 |
| EP | 3258883 | 12/2017 |
| EP | 3273910 | 1/2018 |
| JP | H06504516 | 5/1994 |
| JP | H10258124 | 9/1998 |
| JP | 2002509756 | 4/2002 |
| JP | 2005280917 | 10/2005 |
| JP | 2008528117 | 7/2008 |
| JP | 2008541863 | 11/2008 |
| JP | 2009195712 | 9/2009 |
| JP | 2010518947 | 6/2010 |
| JP | 2012500665 | 1/2012 |
| JP | 5219518 | 6/2013 |
| WO | WO1992017118 | 10/1992 |
| WO | WO1995016407 | 6/1995 |
| WO | WO1999004730 | 2/1999 |
| WO | WO1999039648 | 8/1999 |
| WO | WO1999049799 | 10/1999 |
| WO | WO2001010343 | 2/2001 |
| WO | WO2002003892 | 1/2002 |
| WO | WO2002028421 | 4/2002 |
| WO | WO2002039908 | 5/2002 |
| WO | WO2003043685 | 5/2003 |
| WO | WO2004084746 | 10/2004 |
| WO | WO2004093728 | 11/2004 |
| WO | WO2004096097 | 11/2004 |
| WO | WO2004112657 | 12/2004 |
| WO | WO2005002466 | 1/2005 |
| WO | WO2005007219 | 1/2005 |
| WO | WO2005009285 | 2/2005 |
| WO | WO2005009506 | 2/2005 |
| WO | WO2005087140 | 9/2005 |
| WO | WO2006041877 | 4/2006 |
| WO | WO2006063199 | 6/2006 |
| WO | WO2007008371 | 1/2007 |
| WO | WO2007067820 | 6/2007 |
| WO | WO2008022077 | 2/2008 |
| WO | WO2008028569 | 3/2008 |
| WO | WO2008035337 | 3/2008 |
| WO | 2008103722 | 8/2008 |
| WO | WO2008103497 | 8/2008 |
| WO | WO2008129405 | 10/2008 |
| WO | WO2009045338 | 4/2009 |
| WO | WO2009091509 | 7/2009 |
| WO | WO2010006627 | 1/2010 |
| WO | WO2010008549 | 1/2010 |
| WO | WO2010057262 | 5/2010 |
| WO | WO2010080594 | 7/2010 |
| WO | WO2010098857 | 9/2010 |
| WO | WO2010099032 | 9/2010 |
| WO | WO2010117680 | 10/2010 |
| WO | WO2010121076 | 10/2010 |
| WO | WO2011025981 | 3/2011 |
| WO | WO2011047168 | 4/2011 |
| WO | WO2011051043 | 5/2011 |
| WO | WO2011057087 | 5/2011 |
| WO | WO2011072084 | 6/2011 |
| WO | WO2011106137 | 9/2011 |
| WO | WO2011106544 | 9/2011 |
| WO | WO2011111047 | 9/2011 |
| WO | WO2011137531 | 11/2011 |
| WO | WO2011139747 | 11/2011 |
| WO | WO2012011018 | 1/2012 |
| WO | WO2012011108 | 1/2012 |
| WO | WO2012027487 | 3/2012 |
| WO | WO2012035279 | 3/2012 |
| WO | WO2012040655 | 3/2012 |
| WO | WO2012047644 | 4/2012 |
| WO | WO2012052718 | 4/2012 |

(56) References Cited

FOREIGN PATENT DOCUMENTS

| | | |
|---|---|---|
| WO | WO2012055498 | 5/2012 |
| WO | WO2012087842 | 6/2012 |
| WO | WO2012095455 | 7/2012 |
| WO | WO2012102928 | 8/2012 |
| WO | WO2012106602 | 8/2012 |
| WO | WO2012118508 | 9/2012 |
| WO | WO2012118816 | 9/2012 |
| WO | WO2012118894 | 9/2012 |
| WO | WO2012177942 | 12/2012 |
| WO | WO2013021374 | 2/2013 |
| WO | WO2013021375 | 2/2013 |
| WO | WO2013028387 | 2/2013 |
| WO | WO2013059743 | 4/2013 |
| WO | WO2013059747 | 4/2013 |
| WO | WO2013114214 | 8/2013 |
| WO | WO2013120181 | 8/2013 |
| WO | WO2013123059 | 8/2013 |
| WO | WO2013128432 | 9/2013 |
| WO | WO2013130641 | 9/2013 |
| WO | WO2013131925 | 9/2013 |
| WO | WO2013140318 | 9/2013 |
| WO | WO2013148017 | 10/2013 |
| WO | WO2013148018 | 10/2013 |
| WO | WO2013148019 | 10/2013 |
| WO | WO2013150512 | 10/2013 |
| WO | WO2013152161 | 10/2013 |
| WO | WO2013158613 | 10/2013 |
| WO | WO2013169448 | 11/2013 |
| WO | WO2013175468 | 11/2013 |
| WO | WO2013176583 | 11/2013 |
| WO | WO2013188077 | 12/2013 |
| WO | WO2013192107 | 12/2013 |
| WO | WO2014036113 | 3/2014 |
| WO | WO2014043527 | 3/2014 |
| WO | WO2014047111 | 3/2014 |
| WO | WO2014047325 | 3/2014 |
| WO | WO2014055981 | 4/2014 |
| WO | WO2014059432 | 4/2014 |
| WO | WO2014064694 | 5/2014 |
| WO | WO2014066365 | 5/2014 |
| WO | WO2014093861 | 6/2014 |
| WO | WO2014111918 | 7/2014 |
| WO | WO2014114794 | 7/2014 |
| WO | WO2014114795 | 7/2014 |
| WO | WO2014114796 | 7/2014 |
| WO | WO2014114798 | 7/2014 |
| WO | WO2014116502 | 7/2014 |
| WO | WO2014121280 | 8/2014 |
| WO | WO2014128705 | 8/2014 |
| WO | WO2014134277 | 9/2014 |
| WO | WO2014138194 | 9/2014 |
| WO | WO2014138284 | 9/2014 |
| WO | WO2014138482 | 9/2014 |
| WO | WO2014138868 | 9/2014 |
| WO | WO2014144100 | 9/2014 |
| WO | WO2014144937 | 9/2014 |
| WO | WO2014145338 | 9/2014 |
| WO | WO2014147336 | 9/2014 |
| WO | WO2014152306 | 9/2014 |
| WO | WO2014152375 | 9/2014 |
| WO | WO2014152503 | 9/2014 |
| WO | WO2014153544 | 9/2014 |
| WO | WO2014158617 | 10/2014 |
| WO | WO2014162181 | 10/2014 |
| WO | WO2014162306 | 10/2014 |
| WO | WO2014163705 | 10/2014 |
| WO | WO2014168655 | 10/2014 |
| WO | WO2014179391 | 11/2014 |
| WO | WO2014181336 | 11/2014 |
| WO | WO2014189974 | 11/2014 |
| WO | WO2014191994 | 12/2014 |
| WO | WO2014194178 | 12/2014 |
| WO | WO2014201384 | 12/2014 |
| WO | WO2014201452 | 12/2014 |
| WO | WO2014205064 | 12/2014 |
| WO | WO2014207699 | 12/2014 |
| WO | WO2014210124 | 12/2014 |
| WO | WO2014210299 | 12/2014 |
| WO | WO2015009503 | 1/2015 |
| WO | WO2015020971 | 2/2015 |
| WO | WO2015028986 | 3/2015 |
| WO | WO2015051430 | 4/2015 |
| WO | WO2015052663 | 4/2015 |
| WO | WO2015057407 | 4/2015 |
| WO | WO2015057735 | 4/2015 |
| WO | WO2015057995 | 4/2015 |
| WO | WO2015061378 | 4/2015 |
| WO | WO2015061431 | 4/2015 |
| WO | WO2015061463 | 4/2015 |
| WO | WO2015061533 | 4/2015 |
| WO | WO2015075128 | 5/2015 |
| WO | WO2015081775 | 6/2015 |
| WO | WO2015089334 | 6/2015 |
| WO | WO2015092554 | 6/2015 |
| WO | WO2015120122 | 8/2015 |
| WO | WO2015125024 | 8/2015 |
| WO | WO2015127264 | 8/2015 |
| WO | WO2015127283 | 8/2015 |
| WO | WO2015191604 | 8/2015 |
| WO | WO2015191839 | 8/2015 |
| WO | WO2015195823 | 8/2015 |
| WO | WO2016011185 | 8/2015 |
| WO | WO2015128739 | 9/2015 |
| WO | WO2015128741 | 9/2015 |
| WO | WO2015128747 | 9/2015 |
| WO | WO2015132667 | 9/2015 |
| WO | WO2015132668 | 9/2015 |
| WO | WO2015135050 | 9/2015 |
| WO | WO2015142648 | 9/2015 |
| WO | WO2015142834 | 9/2015 |
| WO | WO2016020918 | 9/2015 |
| WO | WO2016027272 | 9/2015 |
| WO | WO2016059533 | 9/2015 |
| WO | WO2016065158 | 9/2015 |
| WO | WO2016073741 | 9/2015 |
| WO | WO2016083551 | 9/2015 |
| WO | WO2016093877 | 9/2015 |
| WO | WO2015148241 | 10/2015 |
| WO | WO2015171190 | 11/2015 |
| WO | WO2015171743 | 11/2015 |
| WO | WO2015179181 | 11/2015 |
| WO | WO2016097337 | 6/2016 |
| WO | WO2016108181 | 7/2016 |
| WO | WO2016133950 | 8/2016 |
| WO | WO2016150806 | 9/2016 |
| WO | 2017062640 | 4/2017 |
| WO | 2017096157 | 6/2017 |
| WO | 2017101232 | 6/2017 |
| WO | 2017117388 | 7/2017 |
| WO | WO-2017127939 | 8/2017 |
| WO | WO-2017136596 | 8/2017 |
| WO | 2017196511 | 11/2017 |
| WO | 2017196909 | 11/2017 |
| WO | 2017196977 | 11/2017 |
| WO | 2017197064 | 11/2017 |
| WO | 2017218671 | 12/2017 |
| WO | 2018017886 | 1/2018 |

OTHER PUBLICATIONS

Bernard et al., "Aortic Valve Area Evolution After Percutaneous Aortic Valvuloplasty," European Heart Journal, Jul. 1990, vol. 11 (2), pp. 98-107.

BlueCross BlueShield of Northern Carolina Corporate Medical Policy "Balloon valvuloplasty, Percutaneous", (Jun. 1994).

Cimino et al., "Physics of Ultrasonic Surgery Using Tissue Fragmentation: Part I and Part II", Ultrasound in Medicine and Biologyl, Jun. 1996, vol. 22 (1), pp. 89-100, and pp. 101-117.

Cimino, "Ultrasonic Surgery: Power Quantification and Efficiency Optimization", Aesthetic Surgery Journal, Feb. 2001, pp. 233-241.

Cowell et al., "A Randomized Trial of Intensive Lipid-Lowering Therapy in Calcific Aortic Stenosis," NEJM, Jun. 2005, vol. 352 (23), pp. 2369-2397.

(56) References Cited

OTHER PUBLICATIONS

De Korte et al., "Characterization of Plaque Components and Vulnerability with Intravascular Ultrasound Elastography", Phys. Med. Biol., Feb. 2000, vol. 45, pp. 1465-1475.
European Search Report dated Mar. 13, 2015 for European Application. No. 05853460.3.
Feldman, "Restenosis Following Successful Balloon Valvuloplasty: Bone Formation in Aortic Valve Leaflets", Cathet Cardiovasc Diagn, May 1993, vol. 29 (1), pp. 1-7.
Final Office Action dated Aug. 29, 2014 for U.S. Appl. No. 13/842,785.
Final Office Action dated Aug. 29, 2014 for U.S. Appl. No. 13/946,552.
Final Office Action dated Feb. 17, 2010 for U.S. Appl. No. 11/299,246.
Final Office Action dated Jan. 5, 2015 for U.S. Appl. No. 13/842,785.
Final Office Action dated Jan. 5, 2015 for U.S. Appl. No. 13/946,628.
Final Office Action dated Jan. 6, 2014 for U.S. Appl. No. 13/329,083.
Final Office Action dated Jan. 8, 2015 for U.S. Appl. No. 13/946,552.
Final Office Action dated Jul. 15, 2014 for U.S. Appl. No. 13/949,098.
Final Office Action dated Jul. 3, 2012 for U.S. Appl. No. 12/870,270.
Final Office Action dated Jun. 6, 2008 for U.S. Appl. No. 11/299,246.
Final Office Action dated Sep. 2, 2014 for U.S. Appl. No. 13/946,628.
Final Office Action dated Sep. 27, 2016 for U.S. Appl. No. 14/820,830.
Final Office Action dated Sep. 27, 2016 for U.S. Appl. No. 14/815,651.
Fitzgerald et al., "Intravascular Sonotherapy Decreased Neointimal Hyperplasia After Stent implantation in Swine", Circulation, Feb. 2001, vol. 103, pp. 1828-1831.
Freeman et al., "Ultrasonic Aortic Valve Decalcification: Serial Doppler Echocardiographic Follow Up", J Am Coll Cardiol., Sep. 1990, vol. 16 (3), pp. 623-630.
Greenleaf et al., "Selected Methods for Imaging Elastic Properties of Biological Tissues", Annu. Rev. Biomed. Eng., Apr. 2003, vol. 5, pp. 57-78.
Gunn et al., "New Developments in Therapeutic Ultrasound-Assisted Coronary Angioplasty", Curr Interv Cardiol Rep., Dec. 1990, vol. 1 (4), pp. 281-290.
Guzman et al., "Bioeffects Caused by Changes in Acoustic Cavitation Bubble Density and Cell Concentration: A Unified Explanation Based on Cell-to-Bubble Ratio and Blast Radius", Ultrasound in Med. & Biol., Mar. 2003, vol. 29 (8), pp. 1211-1222.
Hallgrimsson et al., "Chronic Non-Rheumatic Aortic Valvular Disease: a Population Study Based on.Autopsies", J Chronic Dis., Jun. 1979, vol. 32 (5), pp. 355-363.
Isner et al., "Contrasting Histoarchitecture of Calcified Leaflets from Stenotic Bicuspid Versus Stenotic Tricuspid Aortic Valves", J Am Coll Cardiol., Apr. 1990, vol. 15 (5), p. 1104-1108.
Lung et al., "A Prospective Survey of Patients with Valvular Heart Disease in Europe: The Euro Heart Survey on Valvular Heart Disease", Euro Heart Journal, Mar. 2003, vol. 24, pp. 1231-1243.
McBride et al "Aortic Valve Decalcification", J Thorac Cardiovas-Surg, Jul. 1990, vol. 100, pp. 36-42.
Miller et al., "Lysis and Sonoporation of Epidermoid and Phagocytic Monolayer Cells by Diagnostic Ultrasound Activation of Contrast Agent Gas Bodies", Ultrasound in Med. & Biol., May 2007, vol. 27 (8), pp. 1107-1113.
Mohler, "Mechanisms of Aortic Valve Calcificaion", Am J Cardiol, Dec. 2004, vol. 94 (11), pp. 1396-1402.
Non Final Office Action dated Apr. 7, 2009 for U.S. Appl. No. 11/299,246.
Non Final Office Action dated Aug. 22, 2007 for U.S. Appl. No. 11/299,246.
Non Final Office Action dated Dec. 10, 2015 for U.S. Appl. No. 13/329,083.
Non Final Office Action dated Dec. 18, 2014 for U.S. Appl. No. 13/949,098.
Non Final Office Action dated Feb. 24, 2014 for U.S. Appl. No. 13/949,098.
Non Final Office Action dated Feb. 3, 2014 for U.S. Appl. No. 13/842,785.
Non Final Office Action dated Feb. 3, 2014 for U.S. Appl. No. 13/946,552.
Non Final Office Action dated Feb. 4, 2014 for U.S. Appl. No. 13/946,628.
Non Final Office Action dated Jul. 1, 2016 for U.S. Appl. No. 15/146,750.
Non Final Office Action dated Jul. 25, 2013 for U.S. Appl. No. 13/329,083.
Non Final Office Action dated Jul. 5, 2016 for U.S. Appl. No. 15/146,773.
Non Final Office Action dated Jun. 14, 2016 for U.S. Appl. No. 14/352,964.
Non Final Office Action dated Mar. 14, 2016 for U.S. Appl. No, 14/807,788.
Non Final Office Action dated May 20, 2016 for U.S. Appl. No. 14/815,651.
Non Final Office Action dated May 20, 2016 for U.S. Appl. No. 14/820,830.
Non Final Office Action dated Nov. 18, 2011 for U.S. Appl. No. 12/870,270.
Non Final Office Action dated Oct. 16, 2008 for U.S. Appl. No. 11/299,246.
Notice of Allowance dated Apr. 7, 2015 for U.S. Appl. No. 13/842,785.
Notice of Allowance dated Mar. 25, 2015 for U.S. Appl. No. 13/946,552.
Notice of Allowance dated Mar. 25, 2015 for U.S. Appl. No. 13/946,628.
Notice of Allowance dated May 27, 2010 for U.S. Appl. No. 11/299,246.
Notice of Allowance dated May 8, 2015 for U.S. Appl. No. 13/949,098.
Notice of Allowance dated Nov. 12, 2016 for U.S. Appl. No. 14/627,566.
Notice of Allowance dated Oct. 26, 2016 for U.S. Appl. No. 14/775,575.
Office Action dated Aug. 29, 2016 for Japanese Application No. 2014537341.
Office Action dated Feb. 23, 2011 for Japanese Application No. 2007545650.
Otto et al., "Three-Year Outcome After Balloon Aortic Valvuloplasty. Insights into Prognosis of Valvular Aortic Stenosis", Circulation, Feb. 1994, vol. 89, pp. 642-650.
Passik et al., "Temporal Changes in the Causes of Aortic Sternosis: A Surgical Pathologic Study of 646 Cases", Mayo Clin Proc, Feb. 1987, vol. 62, pp. 19-123.
Quaden et al., "Percutaneous Aortic Valve Replacement: Resection Before Implantation", Bur J.Cardiothorac Surg, Jan. 2005, vol. 27, pp, 836-840.
Riebman et al., "New Concepts in the Management of Patients with Aortic Valve Disease", Abstract, Valvular Heart Disease, JACC, Mar. 2004, p. 34A.
Rosenschein et al., "Percutaneous Transluminal Therapy of Occluded Saphenous Vein Grafts" Circulation, Jan. 1999, vol. 99, pp. 26-29.
Sakata et al., "Percutaneous Balloon Aortic Valvuloplasty: Antegrade Transseptal vs. Conventional Retrograde Transarterial Approach", Catheter Cardiovasc Interv., Mar. 2005, vol. 64 (3), pp. 314-321.
Sasaki et al., "Scanning Electron Microscopy and Fourier Transformed Infrared Spectroscopy Analysis of Bone Removal Using Er:YAG and CO2 Lasers", J Periodontol., Jun. 2002, vol. 73 (6), pp, 643-652.
Search Report and Written Opinion dated Dec. 10, 2012 for PCT Application No. PCT/US2012/043636.
Search Report and Written Opinion dated Dec. 6, 2016 for PCT Application No. PCT/US2016/047831.
Search Report and Written Opinion dated Jan. 30, 2013 PCT Application No. PCT/US2012/061215.
Search Report and Written Opinion dated Jan. 30, 2013 PCT Application No. PCT/US2012/061219.
Search Report and Written Opinion dated Mar. 2, 2015 for PCT Application No. PCT/US2014/029549.
Search Report and Written Opinion dated May 1, 2012 for PCT Application No. PCT/US2011/065627.

(56) References Cited

OTHER PUBLICATIONS

Search Report and Written Opinion dated May 22, 2007 for PCT Application No. PCT/US2005/044543.
Search Report and Written Opinion dated Oct. 20, 2014 for PCT Application No. PCT/US2014/038849.
Search Report and Written Opinion dated Sep. 4, 2014 for PCT Application No. PCT/US2014/014704.
The CoreValve System Medtronic, 2012, 4 Pages.
Van Den Brand et al., "Histological Changes in the Aortic Valve after Balloon Diiation: Evidence for a Delayed Healing Process", Br Heart J, Jun. 1992,vol. 67, pp. 445-459.
Verdaadadonk et al., "The Mechanism of Action of the Ultrasonic Tissue Resectors Disclosed Using High-Speed and Thermal Imaging Techniques", SPIE, Jan. 1999, vol. 3594, pp. 221-231.
Voelker et al., "Inoperative Valvuloplasty in Calcific Aortic Stenosis: a Study Comparing the Mechanism of a Novel Expandable Device with Conventional Balloon Dilation", Am Heart J., Nov. 1991, vol. 122 (5), pp. 1327-1333.
Waller et al., "Catheter Balloon Valvuloplasty of Stenotic Aortic Valves. Part II: Balloon Valvuloplasty During Life Subsequent Tissue Examination", Clin Cardiol., Nov. 1991, vol. 14 (11), pp. 924-930.
Wang, "Balloon Aortic Valvuloplasty", Prog Cardiovasc Dis., Jul.-Aug. 1997, vol. 40 (1), pp. 27-36.
Wilson et al., "Elastography—The movement Begins", Phys. Med. Biol., Jun. 2000, vol. 45, pp. 1409-1421.
Yock et al, "Catheter-Based Ultrasound Thrombolysis", Circulation, Mar. 1997, vol. 95 (6), pp. 1411-1416.
International Search Report and Written Opinion dated Jul. 11, 2018 for PCT Application No. PCT/US2018/027990, 15 pages.
International Search Report and Written Opinion dated Jun. 28, 2018 for PCT Application No. PCT/US2018/027983, 15 pages.
International Search Report and Written Opinion dated Aug. 3, 2018 for PCT Application No. PCT/US2018/035086, 15 pages.
International Search Report and Written Opinion dated Aug. 9, 2018 for PCT Application No. PCT/US2018/035081, 11 pages.

* cited by examiner

IMPLANT HEART VALVE DEVICES, MITRAL VALVE REPAIR DEVICES AND ASSOCIATED SYSTEMS AND METHODS

CROSS-REFERENCE TO RELATED APPLICATION

The present application claims priority to U.S. Provisional Patent Application No. 62/208,458, filed Aug. 21, 2015, entitled "IMPLANTABLE HEART VALVE DEVICES, MITRAL VALVE REPAIR DEVICES AND ASSOCIATED SYSTEMS AND METHODS", which is incorporated by reference in its entirety.

TECHNICAL FIELD

The present technology relates generally to implantable heart valve devices. In particular, several embodiments are directed to mitral valve devices for percutaneous repair of native mitral valves and associated systems and methods for repair and/or replacement of native mitral valves.

BACKGROUND

Conditions affecting the proper functioning of the mitral valve include, for example, mitral valve regurgitation, mitral valve prolapse and mitral valve stenosis. Mitral valve regurgitation is a disorder of the heart in which the leaflets of the mitral valve fail to coapt into apposition at peak systolic contraction pressures such that blood leaks abnormally from the left ventricle into the left atrium. There are a number of structural factors that may affect the proper closure of the mitral valve leaflets.

One structural factor that causes the mitral valve leaflet to separate is dilation of the heart muscle. FIG. 1A is a schematic illustration of a native mitral valve showing normal coaptation between the anterior mitral valve leaflet (AMVL) and the posterior mitral valve leaflet (PMVL), and FIG. 1B is a schematic illustration of a native mitral valve following a myocardial infarction which has dilated the ventricular free wall to an extent that mitral valve regurgitation has developed. Functional mitral valve disease is characterized by dilation of the left ventricle and a concomitant enlargement of the mitral annulus. As shown in FIG. 1B, the enlarged annulus separates the free edges of the anterior and posterior leaflets from each other such that the mitral leaflets do not coapt properly. The enlarged left ventricle also displaces the papillary muscles further away from the mitral annulus. Because the chordae tendineae are of a fixed length, displacement of the papillary displacement can cause a "tethering" effect that can also prevent proper coaptation of the mitral leaflets. Therefore, dilation of the heart muscle can lead to mitral valve regurgitation.

Another structural factor that can cause abnormal backflow is compromised papillary muscle function due to ischemia or other conditions. As the left ventricle contracts during systole, the affected papillary muscles do not contract sufficiently to effect proper closure of the valve. This in turn can lead to mitral valve regurgitation.

Treatment for mitral valve regurgitation has typically involved the application of diuretics and/or vasodilators to reduce the amount of blood flowing back into the left atrium. Other procedures have involved surgical approaches (open and intravascular) for either the repair or replacement of the valve. Replacement surgery, either done through large open thoracotomies or less invasively through a percutaneous approach, can be effective, but there are compromises of implanting a prosthetic valve. For example, prosthetic mechanical valves require a lifetime of anticoagulation therapy and risks associated with stroke or bleeding. Additionally, prosthetic tissue valves have a finite lifetime, eventually wearing out, for example, over twelve or fifteen years. Therefore, valve replacement surgeries have several shortcomings.

Mitral valve replacement also poses unique anatomical obstacles that render percutaneous mitral valve replacement significantly more challenging than other valve replacement procedures, such as aortic valve replacement. First, aortic valves are relatively symmetric and uniform, but in contrast the mitral valve annulus has a non-circular D-shape or kidney-like shape, with a non-planar, saddle-like geometry often lacking symmetry. Such unpredictability makes it difficult to design a mitral valve prosthesis having that properly conforms to the mitral annulus. Lack of a snug fit between the prosthesis and the native leaflets and/or annulus may leave gaps therein that allows backflow of blood through these gaps. Placement of a cylindrical valve prosthesis, for example, may leave gaps in commissural regions of the native valve that cause perivalvular leaks in those regions. Thus, the anatomy of mitral valves increases the difficulty of mitral valve replacement procedures and devices.

In addition to its irregular, unpredictable shape, which changes size over the course of each heartbeat, the mitral valve annulus lacks radial support from surrounding tissue. The aortic valve, for example, is completely surrounded by fibro-elastic tissue that provides good support for anchoring a prosthetic valve at a native aortic valve. The mitral valve, on the other hand, is bound by muscular tissue on the outer wall only. The inner wall of the mitral valve is bound by a thin vessel wall separating the mitral valve annulus from the inferior portion of the aortic outflow tract. As a result, significant radial forces on the mitral annulus, such as those imparted by an expanding stent prostheses, could lead to impairment of the inferior portion of the aortic tract.

Typical mitral valve repair approaches have involved cinching or resecting portions of the dilated annulus. Cinching of the annulus has been accomplished by implanting annular or peri-annular rings that are generally secured to the annulus or surrounding tissue. Other repair procedures have also involved suturing or clipping of the valve leaflets into partial apposition with one another. For example, the Evalve (Abbott Vascular) MitraClip® clips the two mitral valve leaflets together in the region where the leaflets fail to coapt to thereby reduce or eliminate regurgitation. Mitral valve repair surgery has proven effective, and especially for patients with degenerative disease. Repair surgery typically involves resecting and sewing portions of the valve leaflets to optimize their shape and repairing any torn chordae tendineae, and such surgeries usually include placement of an annuloplasty ring to shrink the overall circumference of the annulus in a manner that reduces the anterior-posterior dimension of the annulus.

Efforts to develop technologies for percutaneous mitral annuloplasty that avoid the trauma, complications, and recovery process associated with surgery, have led to devices and methods for cinching the annulus via the coronary sinus, or cinching the annulus via implantation of screws or anchors connected by a tensioned suture or wire. In operation, the tensioned wire draws the anchors closer to each other to cinch (i.e., pull) areas of the annulus closer together. Additional techniques proposed previously include implanting paired anchors on the anterior and posterior areas of the annulus and pulling them together, and using RF energy to shrink the annular tissue among other approaches.

However, all of these percutaneous annuloplasty approaches have eluded meaningful clinical or commercial success to date, at least partly due to the forces required to change the shape of the native annulus, which is relatively stiff and is subject to significant loads due to ventricular pressure. Furthermore, many of the surgical repair procedures are highly dependent upon the skill of the cardiac surgeon where poorly or inaccurately placed sutures may affect the success of procedures. Overall, many mitral valve repair and replacement procedures have limited durability due to improper sizing or valve wear.

Given the difficulties associated with current procedures, there remains the need for simple, effective, and less invasive devices and methods for treating dysfunctional heart valves, for example, in patients suffering functional mitral valve disease.

SUMMARY OF TECHNOLOGY

At least some embodiments are directed to a method of repairing a native mitral valve having an anterior leaflet and a posterior leaflet between a left atrium and a left ventricle. A repair device having a support can be implanted under the posterior leaflet. The support can be pressed against a portion of an underside of the posterior leaflet and thereby push at least a portion of the posterior leaflet toward the anterior leaflet.

In some embodiments, a method of repairing a native mitral valve having an anterior leaflet and a posterior leaflet between a left atrium and a left ventricle includes positioning a repair device in the left ventricle under the posterior leaflet and between a wall of the left ventricle and chordae tendineae. The repair device can engage an underside of the posterior leaflet such that a portion of the posterior leaflet moves toward the anterior leaflet. In some embodiments, the repair device can further include an appendage extending (e.g., hanging) down beyond an edge of the posterior leaflet and extending that leaflet closer to the anterior leaflet.

At least some embodiments are directed to a method for repairing a native valve of a patient and includes positioning a heart valve repair device in a subannular position behind at least one leaflet connected to chordae tendineae. The repair device has a support in an unexpanded configuration. The support in the subannular position is expanded such that the support engages an interior surface of a heart wall and a downstream-facing surface of the leaflet. The repair device is configured to reposition the leaflet into an at least partially closed position and brace the leaflet to affect native valve function. In some embodiments, the repair device is configured to improve function of the native valve by bracing the leaflet.

In some embodiments, a repair device for repairing a native mitral valve having an anterior leaflet and a posterior leaflet between a left atrium and a left ventricle comprises a support having (a) a contracted configuration in which the support is sized to be inserted under the posterior leaflet between a wall of the left ventricle and chordae tendineae and (b) an extended configuration in which the support projects anteriorly with respect to a posterior wall of the left ventricle by a distance sufficient to position at least a portion of the posterior leaflet toward the anterior leaflet sufficiently to improve coaptation of the posterior and anterior leaflets.

In some embodiments, a heart valve repair device to treat a native valve of a patient comprises a support implantable in a subannular position relative to the native valve. The support can be configured to engage an interior surface of a heart wall and an outward-facing surface of a leaflet of the native valve in the subannular position such that the support repositions the leaflet into a desired position (e.g., at least partially closed position).

In further embodiments, a heart valve repair device to treat a native valve of a patient comprises a frame have a first end configured to be placed at least proximate a first commissure of the native valve, a second end configured to be placed at least proximate a second commissure of the native valve, and a curved region between the first and second ends. The curved region of the frame is configured to engage a backside of a leaflet of the native heart valve so as to reposition the leaflet such that the leaflet at least partially coapts with an adjacent leaflet of the native valve.

In some embodiments, a system to treat a native valve of a patient comprises a prosthetic valve repair device implantable in a subannular position relative to the native valve. The repair device includes a support configured to engage an interior surface of a heart wall and an outward-facing surface of a leaflet of the native valve in a subannular position of the native valve. The support is configured to change an effective annulus shape and/or an effective annulus cross-sectional dimension when the device is in a deployed configuration. In certain embodiments, the system further includes a prosthetic valve having a radially expandable support structure with a lumen and a valve in the lumen and coupled to the support structure. The radially expandable support structure is configured to be deployed within the native valve when the prosthetic valve repair device is implanted in the subannular position and supported within the changed annulus shape or changed annulus cross-sectional dimension.

At least some embodiments are directed to a valve repair device that comprises means for supporting a posterior leaflet. The means for supporting the posterior leaflet has contracted configuration for insertion under the posterior leaflet between a wall of the left ventricle and chordae tendineae and an extended configuration for projecting anteriorly with respect to a posterior wall of the left ventricle. In one embodiment, the means for supporting extends a distance sufficient to position at least a portion of the posterior leaflet toward the anterior leaflet to affect coaptation of the posterior and anterior leaflets. In one embodiment, the means for supporting includes one or more extensions units expandable using one or more filler materials. The means for supporting can further include an elongated spine coupled to the extension unit(s).

BRIEF DESCRIPTION OF THE DRAWINGS

Many aspects of the present disclosure can be better understood with reference to the following drawings. The components in the drawings are not necessarily to scale. Instead, emphasis is placed on illustrating clearly the principles of the present disclosure. Furthermore, components can be shown as transparent in certain views for clarity of illustration only and not to indicate that the illustrated component is necessarily transparent.

DETAILED DESCRIPTION

Figure 1A:
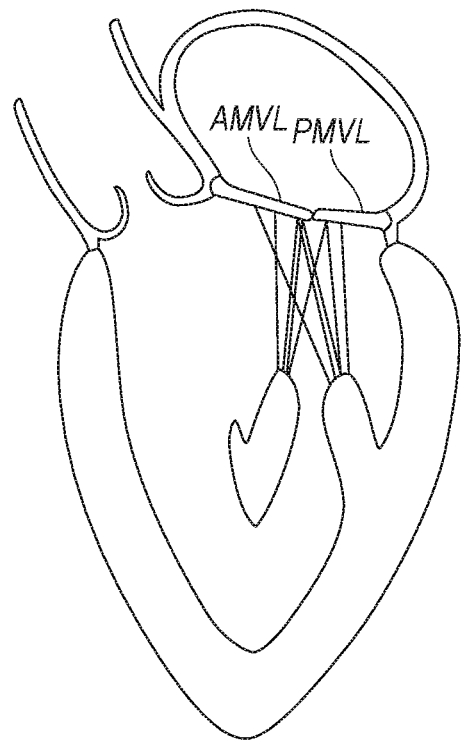
FIG. 1A is a schematic illustration of a native mitral valve showing normal coaptation between the anterior mitral valve leaflet and the posterior mitral valve leaflet.
Figure 1B:
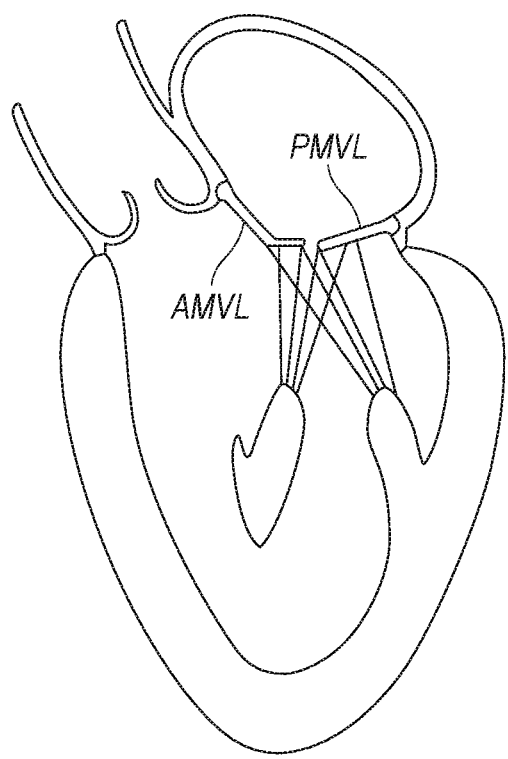
FIG. 1B is a schematic illustration of a native mitral valve following myocardial infarction which has caused the ventricular free wall to dilate, and wherein mitral valve regurgitation has developed.

Specific details of several embodiments of the technology are described below with reference to FIGS. 1A-22.

Although many of the embodiments are described below with respect to devices, systems, and methods for percutaneous repair of a native mitral valve using prosthetic heart valve repair devices, other applications and other embodiments in addition to those described herein are within the scope of the technology. Additionally, several other embodiments of the technology can have different configurations, components, or procedures than those described herein. A person of ordinary skill in the art, therefore, will accordingly understand that the technology can have other embodiments with additional elements, or the technology can have other embodiments without several of the features shown and described below with reference to FIGS. 1A-22.

With regard to the terms "distal" and "proximal" within this description, unless otherwise specified, the terms can reference a relative position of the portions of a heart valve repair device and/or an associated delivery device with reference to an operator and/or a location in the vasculature or heart. For example, in referring to a delivery catheter suitable to deliver and position various heart valve repair or replacement devices described herein, "proximal" can refer to a position closer to the operator of the device or an incision into the vasculature, and "distal" can refer to a position that is more distant from the operator of the device or further from the incision along the vasculature (e.g., the end of the catheter). With respect to a prosthetic heart valve repair or replacement device, the terms "proximal" and "distal" can refer to the location of portions of the device with respect to the direction of blood flow. For example, proximal can refer to an upstream-oriented position or a position of blood inflow, and distal can refer to a downstream-oriented position or a position of blood outflow.

Additionally, the term "expanded configuration" refers to the configuration or state of the device when allowed to freely expand to an unrestrained size without the presence of constraining or distorting forces. The terms "deployed configuration" or "deployed" refer to the device after expansion at the native valve site and subject to the constraining and distorting forces exerted by the native anatomy. The terms "extended configuration" or "extended state" refer to the "expanded configuration and/or deployed configuration," and the terms "contracted configuration" or "contracted state" refer to the device in a compressed or otherwise collapsed state.

For ease of reference, throughout this disclosure identical reference numbers and/or letters are used to identify similar or analogous components or features, but the use of the same reference number does not imply that the parts should be construed to be identical. Indeed, in many examples described herein, the identically numbered parts are distinct in structure and/or function. The headings provided herein are for convenience only.

Overview

Systems, devices and methods are provided herein for percutaneous repair of native heart valves, such as mitral valves. Several of the details set forth below are provided to describe the following examples and methods in a manner sufficient to enable a person skilled in the relevant art to practice, make and use them. Several of the details and advantages described below, however, may not be necessary to practice certain examples and methods of the technology. Additionally, the technology may include other examples and methods that are within the scope of the claims but are not described in detail.

Embodiments of the present technology provide systems, methods and apparatus to treat valves of the body, such as heart valves including the mitral valve. The apparatus and methods enable a percutaneous approach using a catheter delivered intravascularly through a vein or artery into the heart. Additionally, the apparatus and methods enable other less-invasive approaches including trans-apical, trans-atrial, and direct aortic delivery of a heart valve repair device to a target location in the heart. The apparatus and methods enable a prosthetic device to be anchored at or near a native valve location by engaging a subannular surface and other sub-valvular elements of the valve annulus, chordae tendineae, and/or valve leaflets. Additionally, the embodiments of the devices and methods described herein can be combined with many known surgeries and procedures, such as known methods of accessing the valves of the heart (e.g., the mitral valve or tricuspid valve) with antegrade or retrograde approaches, and combinations thereof.

The devices and methods described herein provide a valve repair device that has the flexibility to adapt and conform to the variably-shaped native mitral valve anatomy while physically supporting or bracing (e.g., pushing) the posterior leaflet of the mitral valve toward the anterior leaflet in at least a partially closed position to facilitate coaptation of the native mitral leaflets during systole. Several embodiments of the device effectively reduce the size of the mitral orifice and render the native mitral valve competent. The device has the structural strength and integrity necessary to withstand the dynamic conditions of the heart over time and to permanently anchor the repair device in the subannular position so that the patient can resume a substantially normal life. The systems and methods further deliver such a device in a less-invasive manner to provide a patient with a new, permanent repair device using a lower-risk procedure that has a faster recovery period compared to conventional procedures.

Several embodiments of the present technology include devices for repairing a native valve of a heart. Native heart valves have an annulus and leaflets, and such repair devices include a support for engaging an interior surface of a heart wall and an outward-facing surface (e.g., a backside, underside or downstream side) of a leaflet of the native valve in a subannular position of the native valve. The device can be configured to support the leaflet in an at least partially closed position. In the at least partially closed position the leaflet can be positioned so that valve function is improved, usually by improving the coaptation of the leaflets. For example, in the at least partially closed position the leaflet can be held closer to an opposing leaflet of the native valve such that the two leaflets coapt, or sealingly engage with one another, through a portion of the cardiac cycle. The leaflet may be positioned so that a portion of the leaflet—which may be the free edge of the leaflet or a mid-portion of the leaflet—coapts with a surface of the opposing leaflet with which the leaflet did not coapt prior to treatment. The device can have a support that optionally can include a spine or beam and an extension unit coupled to or extending from or around the spine. In one embodiment, the extension unit can include a biocompatible material suitable to support tissue ingrowth. In various embodiments, the extension unit can include a plurality of projections configured to expand or otherwise extend between and/or engage chordae tendineae associated with the leaflet. In some embodiments, the extension unit comprises a flexible, fluid-impermeable cover, such as an inflatable bladder or balloon, and an injectable filler material within the cover that expands portions of the extension unit and maintains the expanded configuration over time (e.g., filling and expanding the plurality of projections).

Some embodiments of the disclosure are directed to systems to repair a native valve of a patient and implant a prosthetic valve. In one embodiment, the system can have a prosthetic heart valve repair device implantable in a subannular position relative to the native valve and having a support for engaging an interior surface of a heart wall and an outward-facing surface (e.g., a backside, underside or downstream side) of a leaflet of the native valve in a subannular position of the native valve. In this embodiment, the support can be configured to change an annulus shape and/or an annulus cross-sectional dimension when the device is in a deployed configuration. For example, the support can be configured to change the annulus shape from a non-circular cross-section to a more circular or substantially circular cross-section. The system can also include a prosthetic heart valve. The prosthetic heart valve can, for example, include a radially expandable support structure with a lumen and a valve coupled to the support structure in the lumen. In this arrangement, when the prosthetic heart valve repair device is implanted in the subannular position, the radially expandable support structure can be supported within the changed annulus shape or changed annulus cross-sectional dimension. In a particular example, the heart valve repair device can be positioned behind a posterior mitral valve leaflet in a subannular region, and the prosthetic heart valve can have a substantially circular cross-sectional dimension.

Other aspects of the present technology are directed to methods for repairing a native valve of a patient. In one embodiment, a method includes positioning a heart valve repair device in a subannular position behind at least one leaflet connected to chordae tendineae. The repair device can have a support that is initially in a contracted configuration. The method can also include expanding or otherwise extending the support in the subannular position such that the support engages an interior surface of a heart wall and an outward-facing surface (e.g., a backside, underside or downstream side) of the leaflet. In one example, the native valve is a mitral valve and the support can engage a left ventricular wall and a posterior mitral valve leaflet. In exemplary embodiments the support is extended toward a free edge of the leaflet, or toward an opposing leaflet with which the supported leaflet should coapt. In embodiments for mitral valve repair, the support may be extended in an anterior direction (i.e., away from a posterior wall of the ventricle and toward the anterior leaflet), or toward the anterior edge of the posterior leaflet. In various embodiments, the repair device is configured to support the leaflet in at least a partially closed position to facilitate coaptation of the valve leaflets and thereby repair the native valve. This coaptation may occur at the distal free edges of one or both leaflets, or along a middle portion of one or both leaflets.

Another embodiment of the disclosure is directed to a heart valve repair device to treat a native valve of a patient. In various arrangements, the repair device can comprise a frame having a first end configured to be placed at least proximate a first commissure of the native valve and a second end configured to be placed at least proximate a second commissure of the native valve. The frame can further include a curved region between the first and second ends. The curved region of the frame can be configured to engage a backside of a leaflet of the native heart valve such that the leaflet at least partially coapts with an adjacent leaflet of the native valve.

The devices and methods disclosed herein can be configured for treating non-circular, asymmetrically shaped valves and bileaflet or bicuspid valves, such as the mitral valve. It can also be configured for treating other valves of the heart such as the tricuspid valve. Many of the devices and methods disclosed herein can further provide for long-term (e.g., permanent) and reliable anchoring of the prosthetic device even in conditions where the heart or native valve may experience gradual enlargement or distortion.

Cardiac and Mitral Valve Physiology

Figure 2:
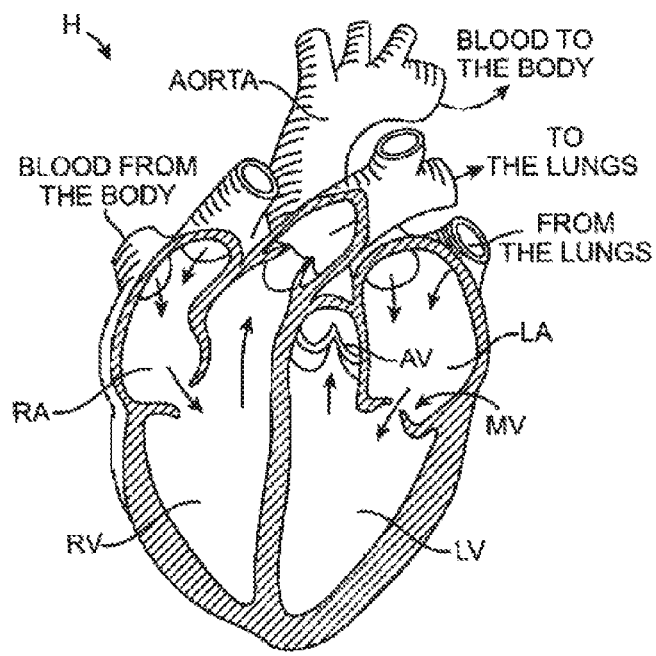
FIGS. 2 and 3 are schematic illustrations of a mammalian heart having native valve structures.
Figure 3:
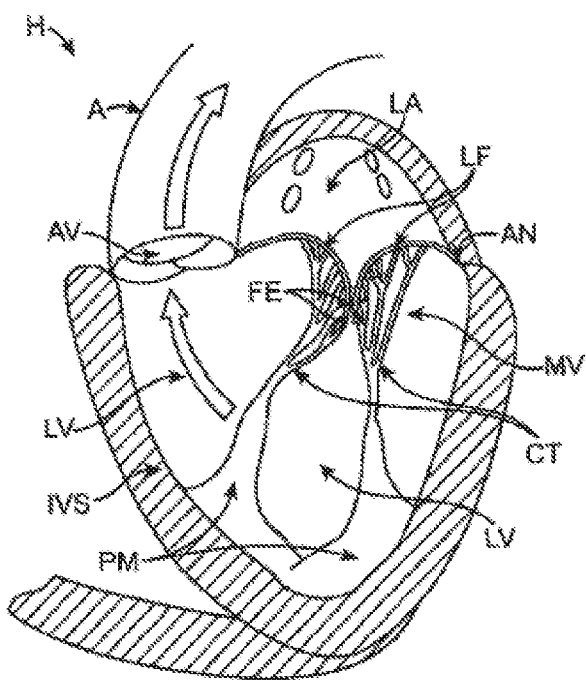

FIGS. 2 and 3 show a normal heart H. The heart comprises a left atrium that receives oxygenated blood from the lungs via the pulmonary veins PV and pumps this oxygenated blood through the mitral valve MV into the left ventricle LV. The left ventricle LV of a normal heart H in systole is illustrated in FIG. 3. The left ventricle LV is contracting and blood flows outwardly through the aortic valve AV in the direction of the arrows. Back flow of blood or "regurgitation" through the mitral valve MV is prevented since the mitral valve is configured as a "check valve" which prevents back flow when pressure in the left ventricle is higher than that in the left atrium LA. More specifically, the mitral valve MV comprises a pair of leaflets having free edges FE which meet evenly, or "coapt" to close, as illustrated in FIG. 3. The opposite ends of the leaflets LF are attached to the surrounding heart structure via an annular region of tissue referred to as the annulus AN.

Figure 4:
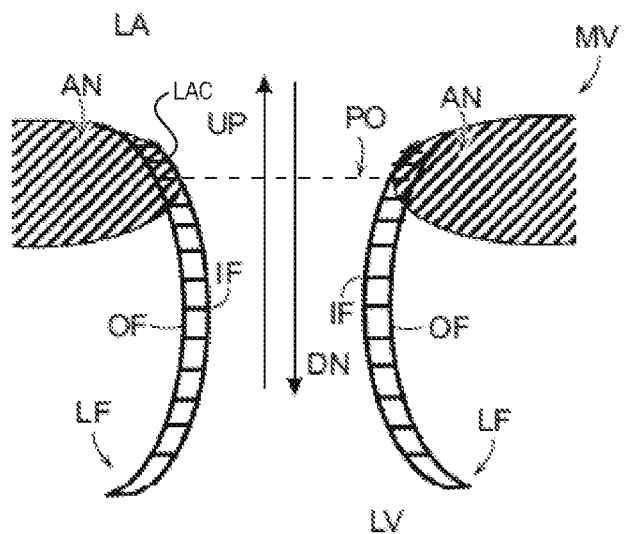
FIG. 4 is a schematic cross-sectional side view of a native mitral valve showing the annulus and leaflets.

FIG. 4 is a schematic cross-sectional side view showing an annulus and leaflets of a mitral valve in greater detail. As illustrated, the opposite ends of the leaflets LF are attached to the surrounding heart structure via a fibrous ring of dense connective tissue referred to as the annulus AN, which is distinct from both the leaflet tissue LF as well as the adjoining muscular tissue of the heart wall. The leaflets LF and annulus AN are comprised of different types of cardiac tissue having varying strength, toughness, fibrosity, and flexibility. Furthermore, the mitral valve MV may also comprise a unique region of tissue interconnecting each leaflet LF to the annulus AN that is referred to herein as leaflet/annulus connecting tissue LAC (indicated by overlapping cross-hatching).

Referring back to FIG. 3, the free edges FE of the mitral leaflets LF are secured to the lower portions of the left ventricle LV through chordae tendineae CT which include a plurality of branching tendons secured over the lower surfaces of each of the valve leaflets LF. The primary chordae CT in turn, are attached to the papillary muscles PM, which extend upwardly from the lower wall of the left ventricle LV and interventricular septum IVS. Although FIG. 3 shows the primary chordae tendineae (CT) which connect the leaflets to the papillary muscles, the posterior leaflet of the mitral valve (as well as the leaflets of the tricuspid valve) also have secondary and tertiary chordae tendineae which connect the leaflets directly to the ventricular wall. These secondary and tertiary chordae tendineae have a range of lengths and positions, connecting to the leaflets at all heights, including close to the leaflets' connection to the valve annulus. The secondary and tertiary chordae tendineae are illustrated in FIGS. 3, 5, 12, 13-16B and 19, and described in further detail herein.

Figure 5:
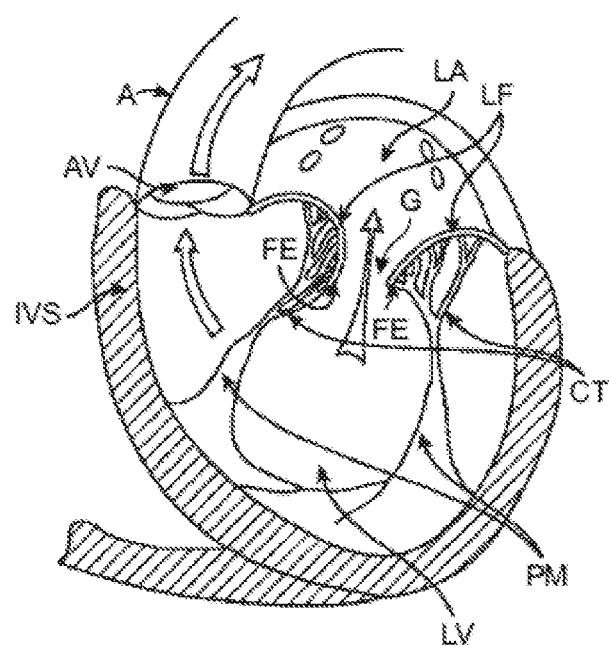
FIG. 5 is a schematic illustration of a heart in a patient suffering from cardiomyopathy, and which is suitable for combination with various prosthetic heart valve repair devices in accordance with embodiments of the present technology.

Referring now to FIG. 5, regurgitation can occur in patients suffering from functional mitral valve disease (e.g., cardiomyopathy) where the heart is dilated and the increased size prevents the valve leaflets LF from meeting properly. The enlargement of the heart causes the mitral annulus to become enlarged such that the free edges FE cannot meet (e.g., coapt) during systole. The free edges FE of the anterior and posterior leaflets normally meet along a line of coaptation C as shown in FIG. 6A, a view of the top or left atrial side of the valve, but a significant gap G can be left in patients suffering from cardiomyopathy, as shown in FIG. 6B.

Figure 6A:
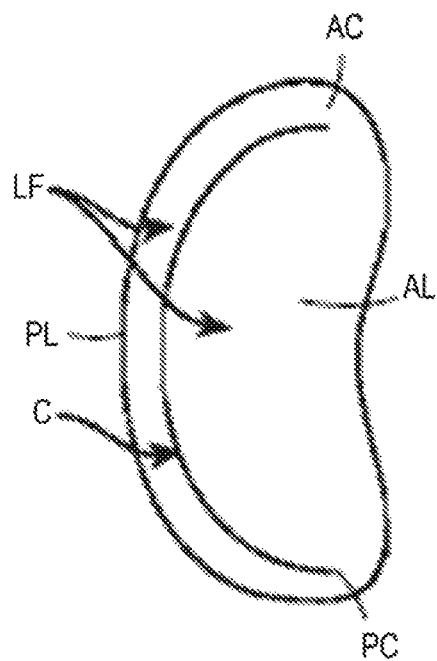
FIG. 6A is a schematic illustration of a native mitral valve of a heart showing normal closure of native mitral valve leaflets.
Figure 6B:
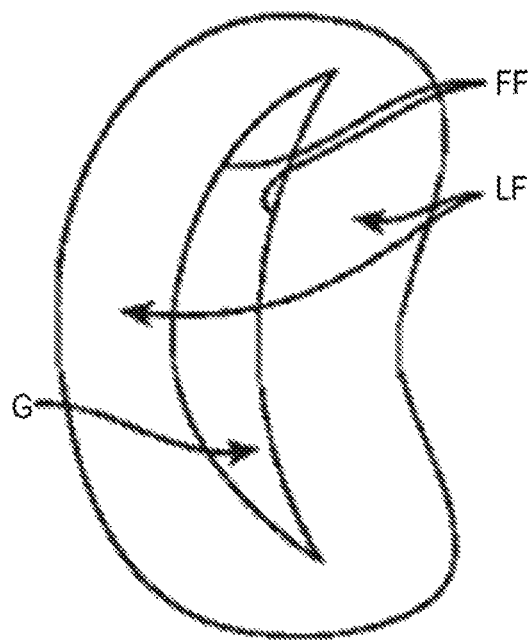
FIG. 6B is a schematic illustration of a native mitral valve of a heart showing abnormal closure of native mitral valve leaflets in a dilated heart, and which is suitable for combination with various prosthetic heart valve repair devices in accordance with embodiments of the present technology.
Figure 6C:
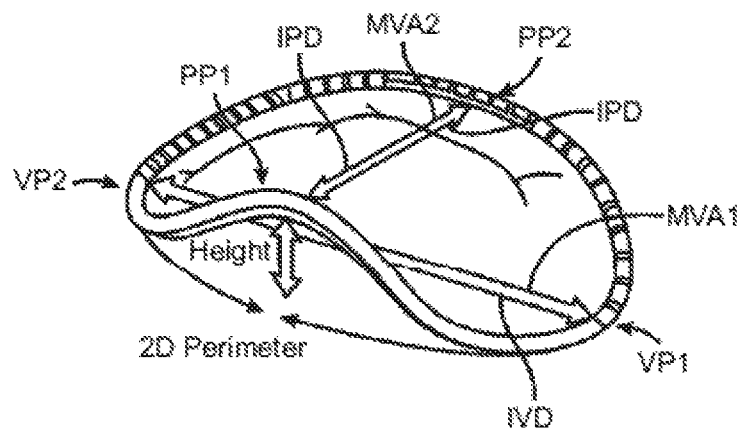
FIG. 6C is a schematic illustration of a mitral valve of a heart showing dimensions of the annulus, and which is suitable for combination with various prosthetic heart valve repair devices in accordance with embodiments of the present technology.

FIGS. 6A-6C further illustrates the shape and relative sizes of the leaflets L of the mitral valve. As shown in FIG. 6C, the overall mitral valve has a generally "D"-shape or kidney-like shape, with a long axis MVA1 and a short axis MVA2. In healthy humans the long axis MVA1 is typically within a range from about 33.3 mm to about 42.5 mm in length (37.9+/−4.6 mm), and the short axis MVA2 is within a range from about 26.9 to about 38.1 mm in length (32.5+/−5.6 mm). However, with patients having decreased cardiac function these values can be larger, for example MVA1 can be within a range from about 45 mm to 55 mm and MVA2 can be within a range from about 35 mm to about 40 mm. The line of coaptation C is curved or C-shaped such that the anterior leaflet AL is larger than the posterior leaflet PL (FIG. 6A). Both leaflets appear generally crescent-shaped from the superior or atrial side, with the anterior leaflet AL being substantially wider in the middle of the valve than the posterior leaflet PL. As illustrated in FIG. 6A, at the opposing ends of the line of coaptation C, the leaflets join together at corners called the anterolateral commissure AC and posteromedial commissure PC.

FIG. 6C shows the shape and dimensions of the annulus of the mitral valve. As described above, the annulus is an annular area around the circumference of the valve comprised of fibrous tissue which is thicker and tougher than that of the leaflets LF and distinct from the muscular tissue of the ventricular and atrial walls. The annulus may comprise a saddle-like shape with a first peak portion PP1 and a second peak portion PP2 located along an interpeak axis IPD, and a first valley portion VP1 and a second valley portion VP2 located along an intervalley axis IVD. The first and second peak portion PP1 and PP2 are higher in elevation relative to a plane containing the nadirs of the two valley portions VP1, VP2, typically being about 8-19 mm higher in humans, thus giving the valve an overall saddle-like shape. The distance between the first and second peak portions PP1, PP2, referred to as interpeak span IPD, is substantially shorter than the intervalley span IVD, the distance between first and second valley portions VP1, VP2.

Referring back to FIG. 4, "subannular," as used herein, refers to a portion of the mitral valve MV that lies on or downstream DN of the plane PO of the native orifice. As used herein, the plane PO of the native valve orifice is a plane generally perpendicular to the direction of blood flow through the valve and which contains either or both the major axis MVA1 or the minor axis MVA2 (FIG. 6C). Thus, a subannular surface of the mitral valve MV is a tissue surface lying on the ventricular side of the plane PO, and preferably one that faces generally downstream, toward the left ventricle LV. The subannular surface may be disposed on the annulus AN itself or the ventricular wall behind the native leaflets LF, or it may comprise an outward-facing or downward-facing surface of the native leaflet OF, which lies below the plane PO. The subannular surface or subannular tissue may thus comprise the annulus AN itself, the outward-facing surface OF of the native leaflets LF, leaflet/annulus connective tissue, the ventricular wall or combinations thereof.

A person of ordinary skill in the art will recognize that the dimensions and physiology of the mitral valves may vary among patients, and although some patients may comprise differing physiology, the teachings as described herein can be adapted for use by many patients having various conditions, dimensions and shapes of the mitral valve. For example, work in relation to embodiments suggests that some patients may have a long dimension across the annulus and a short dimension across the annulus without well-defined peak and valley portions, and the methods and device as described herein can be configured accordingly.

Access to the Mitral Valve

Access to the mitral valve or other atrioventricular valves can be accomplished through the patient's vasculature in a percutaneous manner. By percutaneous it is meant that a location of the vasculature remote from the heart is accessed through the skin; typically using a surgical cut down procedure or a minimally invasive procedure, such as using needle access through, for example, the Seldinger technique. The ability to percutaneously access the remote vasculature is well-known and described in the patent and medical literature. Depending on the point of vascular access, the approach to the mitral valve may be antegrade and may rely on entry into the left atrium by crossing the inter-atrial septum. Alternatively, approach to the mitral valve can be retrograde where the left ventricle is entered through the aortic valve. Once percutaneous access is achieved, the interventional tools and supporting catheter(s) may be advanced to the heart intravascularly and positioned adjacent the target cardiac valve in a variety of manners.

Figure 7:
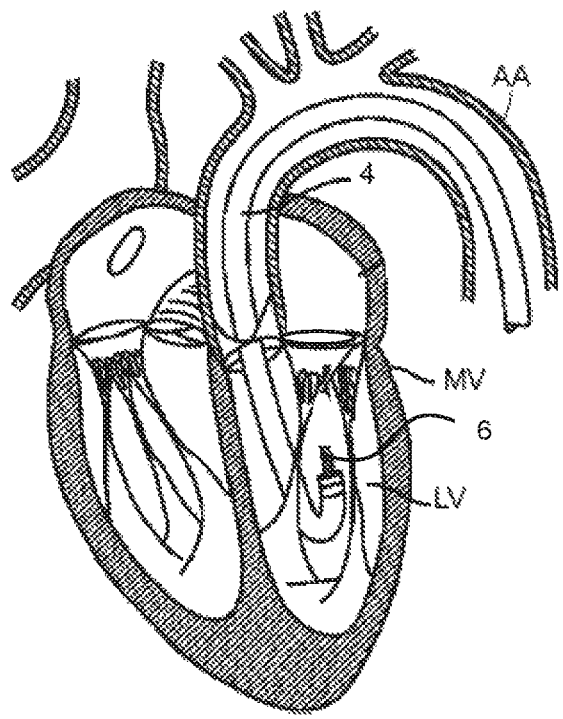
FIGS. 7 and 8 are schematic cross-sectional illustrations of the heart showing retrograde approaches to the native mitral valve through the aortic valve and arterial vasculature in accordance with various embodiments of the present technology.
Figure 8:
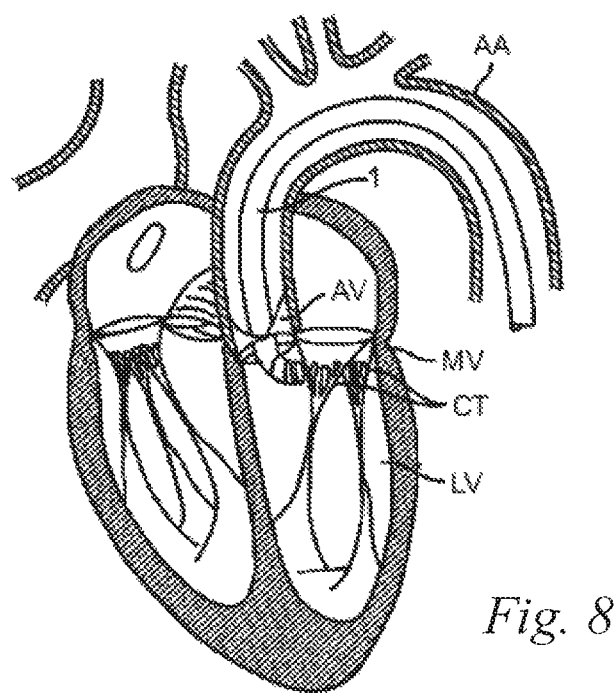

An example of a retrograde approach to the mitral valve is illustrated in FIGS. 7 and 8. The mitral valve MV may be accessed by an approach from the aortic arch AA, across the aortic valve AV, and into the left ventricle LV below the mitral valve MV. The aortic arch AA may be accessed through a conventional femoral artery access route, as well as through more direct approaches via the brachial artery, axillary artery, radial artery, or carotid artery. Such access may be achieved with the use of a guidewire 6. Once in place, a guide catheter 4 may be tracked over the guidewire 6. Alternatively, a surgical approach may be taken through an incision in the chest, preferably intercostally without removing ribs, and placing a guide catheter through a puncture in the aorta itself. The guide catheter 4 affords subsequent access to permit placement of the prosthetic valve device, as described in more detail herein.

In some specific instances, a retrograde arterial approach to the mitral valve may be selected due to certain advantages. For example, use of the retrograde approach can eliminate the need for a trans-septal puncture (described below). The retrograde approach is also more commonly used by cardiologists and thus has the advantage of familiarity.

Figure 9:
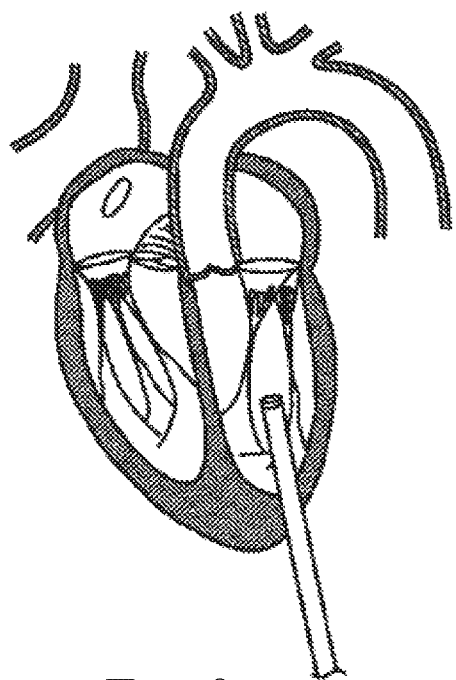
FIG. 9 is a schematic cross-sectional illustration of the heart showing an approach to the native mitral valve using a trans-apical puncture in accordance with various embodiments of the present technology.

An additional approach to the mitral valve is via trans-apical puncture, as shown in FIG. 9. In this approach, access to the heart is gained via thoracic incision, which can be a conventional open thoracotomy or sternotomy, or a smaller intercostal or sub-xyphoid incision or puncture. An access cannula is then placed through a puncture in the wall of the left ventricle at or near the apex of the heart and then sealed by a purse-string suture. The catheters and prosthetic devices of the invention may then be introduced into the left ventricle through this access cannula.

The trans-apical approach has the feature of providing a shorter, straighter, and more direct path to the mitral or aortic valve. Further, because it does not involve intravascular access, the trans-apical procedure can be performed by surgeons who may not have the necessary training in interventional cardiology to perform the catheterizations required in other percutaneous approaches.

Using a trans-septal approach, access is obtained via the inferior vena cava IVC or superior vena cava SVC, through the right atrium RA, across the inter-atrial septum IAS and into the left atrium LA above the mitral valve MV.

Figure 10A:
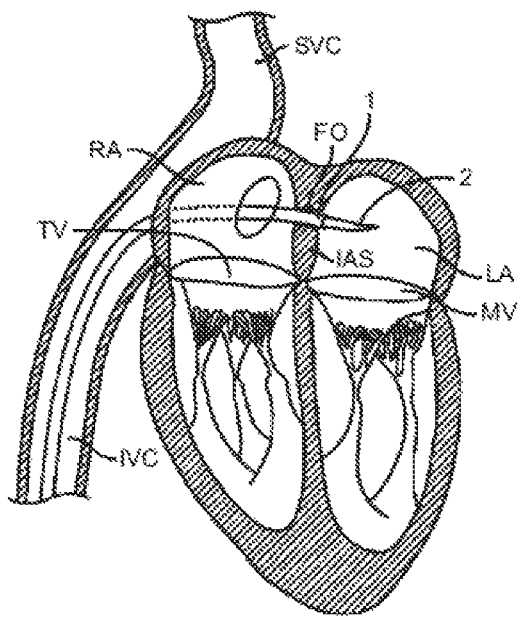
FIG. 10A is a schematic cross-sectional illustration of the heart showing an antegrade approach to the native mitral valve from the venous vasculature in accordance with various embodiments of the present technology.

As shown in FIG. 10A, a catheter 1 having a needle 2 may be advanced from the inferior vena cava IVC into the right atrium RA. Once the catheter 1 reaches the anterior side of the inter-atrial septum IAS, the needle 2 may be advanced so that it penetrates through the septum, for example at the fossa ovalis FO or the foramen ovale into the left atrium LA. The catheter is then advanced into the left atrium over the needle. At this point, a guidewire may be exchanged for the needle 2 and the catheter 1 withdrawn.

Figure 10B:
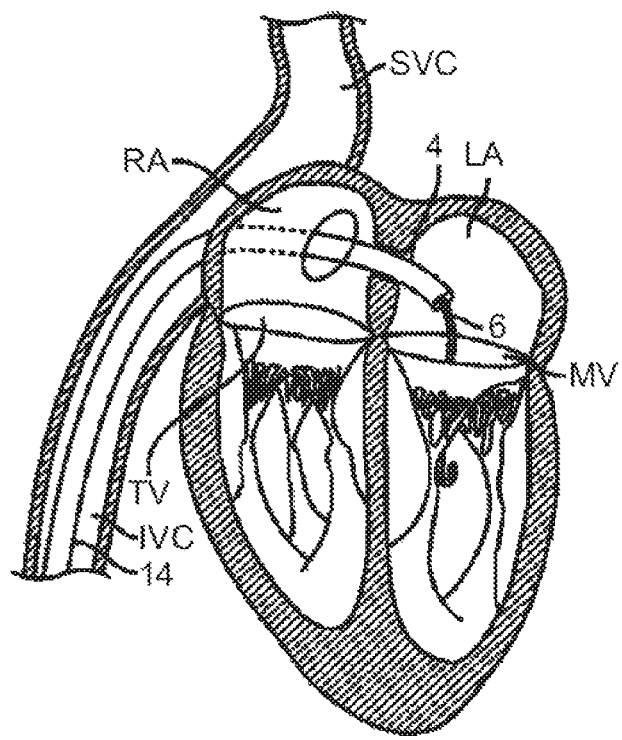
FIG. 10B is a schematic cross-sectional illustration of the heart showing access through the inter-atrial septum (IAS) maintained by the placement of a guide catheter over a guidewire in accordance with various embodiments of the present technology.

As shown in FIG. 10B, access through the inter-atrial septum IAS may usually be maintained by the placement of a guide catheter 4, typically over a guidewire 6 which has been placed as described above. The guide catheter 4 affords subsequent access to permit introduction of the device to repair the mitral valve, as described in more detail herein.

In an alternative antegrade approach (not shown), surgical access may be obtained through an intercostal incision, preferably without removing ribs, and a small puncture or incision may be made in the left atrial wall. A guide catheter may then be placed through this puncture or incision directly into the left atrium, sealed by a purse string-suture.

The antegrade or trans-septal approach to the mitral valve, as described above, can be advantageous. For example, the antegrade approach may decrease risks associated with crossing the aortic valve as in retrograde approaches. This can be particularly relevant to patients with prosthetic aortic valves, which may not be crossed at all or without substantial risk of damage.

The prosthetic valve repair device may also be implanted using conventional open-surgical approaches. For some patients, the devices and methods of the invention may offer a therapy better suited for the treatment of certain valve pathologies or more durable than existing treatments such as annuloplasty or valve replacement.

The prosthetic valve repair device may be specifically designed for the approach or interchangeable among approaches. A person of ordinary skill in the art can identify an appropriate approach for an individual patient and design the treatment apparatus for the identified approach in accordance with embodiments described herein.

Orientation and steering of the prosthetic valve repair device can be combined with many known catheters, tools and devices. Such orientation may be accomplished by gross steering of the device to the desired location and then refined steering of the device components to achieve a desired result.

Gross steering may be accomplished by a number of methods. A steerable guidewire may be used to introduce a guide catheter and the prosthetic valve repair device into the proper position. The guide catheter may be introduced, for example, using a surgical cut down or Seldinger access to the femoral artery in the patient's groin. After placing a guidewire, the guide catheter may be introduced over the guidewire to the desired position. Alternatively, a shorter and differently shaped guide catheter could be introduced through the other routes described above.

A guide catheter may be pre-shaped to provide a desired orientation relative to the mitral valve. For access via the trans-septal approach, the guide catheter may have a curved, angled or other suitable shape at its tip to orient the distal end toward the mitral valve from the location of the septal puncture through which the guide catheter extends. For the retrograde approach, as shown in FIGS. 7 and 8, guide catheter 4 may have a pre-shaped J-tip which is configured so that it turns toward the mitral valve MV after it is placed over the aortic arch AA and through the aortic valve AV. As shown in FIG. 7, the guide catheter 4 may be configured to extend down into the left ventricle LV and to assume a J-shaped configuration so that the orientation of an inter- ventional tool or catheter is more closely aligned with the axis of the mitral valve MV. As shown in FIG. 8, the guide catheter might alternatively be shaped in a manner suitable to advance behind the posterior leaflet. In either case, a pre-shaped guide catheter may be configured to be straightened for endovascular delivery by means of a stylet or stiff guidewire which is passed through a lumen of the guide catheter. The guide catheter might also have pull-wires or other means to adjust its shape for more fine steering adjustment.

Selected Embodiments of Prosthetic Heart Valve Repair Devices and Methods

Embodiments of the present technology can be used to treat one or more of the valves of the heart as described herein, and several embodiments are well suited for treating the mitral valve. Introductory examples of prosthetic heart valve repair devices, system components, and associated methods in accordance with embodiments of the present technology are described in this section with reference to FIGS. 11A-22. It will be appreciated that specific elements, substructures, advantages, uses, and/or other features of the embodiments described with reference to FIGS. 11A-22 can be suitably interchanged, substituted or otherwise configured with one another. Furthermore, suitable elements of the embodiments described with reference to FIGS. 11A-22 can be used as stand-alone and/or self-contained devices.

Systems, devices and methods in accordance with the present technology provide percutaneous implantation of prosthetic heart valve repair devices in a heart of a patient. In some embodiments, methods and devices treat valve diseases by minimally invasive implantation of repair devices behind one or more native leaflets in a subannular position using the techniques described above with respect to FIGS. 7-10B. In one embodiment, the repair device can be suitable for engaging an interior surface of a heart wall, such as a left ventricular wall, and a backside of a leaflet (e.g., the posterior leaflet of a mitral valve in the heart of a patient). In another embodiment, the repair device can be suitable for implantation and repair of another valve in the heart of the patient (e.g., a bicuspid or tricuspid valve).

Figure 11A:
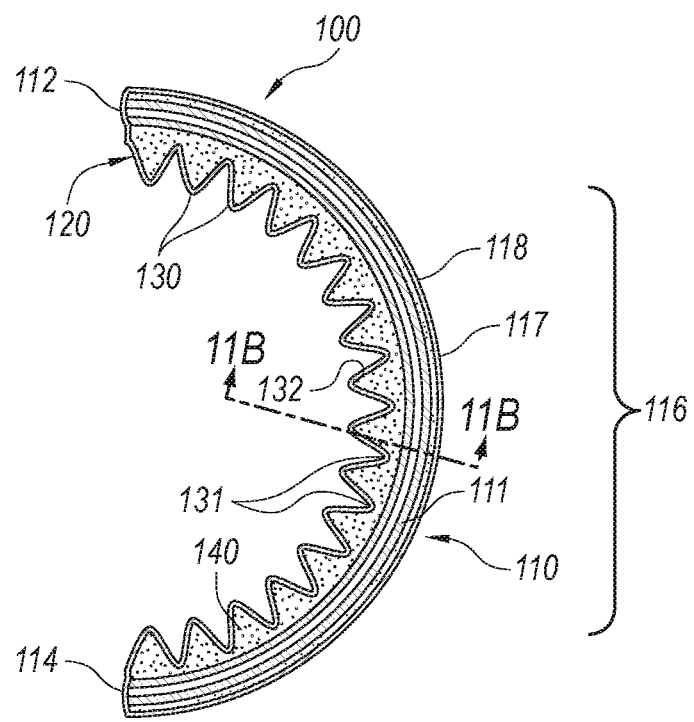
FIG. 11A is a cross-sectional top view of a prosthetic heart valve repair device in an expanded configuration in accordance with an embodiment of the present technology.
Figure 11B:
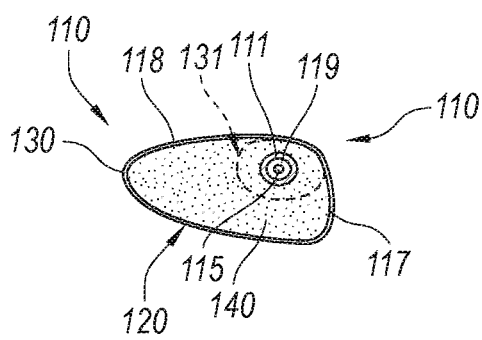
FIG. 11B is a cross-sectional side view of a prosthetic heart valve repair device in an expanded configuration in accordance with an embodiment of the present technology.
Figure 11C:
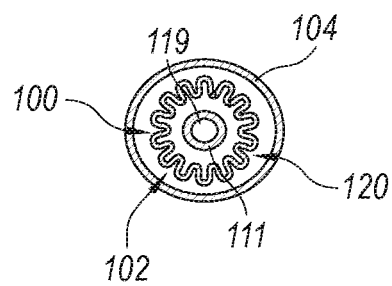
FIG. 11C is a cross-sectional side view of a prosthetic heart valve repair device in a contracted configuration in accordance with an embodiment of the present technology.

FIG. 11A is a cross-sectional top view showing a prosthetic heart valve repair device 100 ("repair device 100") in an expanded or extended configuration in accordance with an embodiment of the present technology, and FIGS. 11B and 11C are cross-sectional side views showing the repair device 100 in the expanded configuration and a contracted or delivery configuration, respectively. The repair device 100 can be movable between the delivery configuration shown in FIG. 11C and the expanded configuration shown in FIGS. 11A-B to be deployed under the posterior leaflet of the mitral valve. In the delivery configuration shown in FIG. 11C, the repair device 100 has a low profile suitable for delivery through a lumen 102 of a small-diameter catheter 104 positioned in the heart via the trans-septal, retrograde, or trans-apical approaches described herein. In some embodiments, the delivery configuration of the repair device 100 will preferably have an outer diameter as small as possible, such as no larger than about 8-10 mm for trans-septal approaches, about 6-8 mm for retrograde approaches, or about 8-12 mm for trans-apical approaches to the mitral valve MV. In some embodiments, the repair device 100 can be resilient and relatively resistant to compression once deployed, making it easier to position and retain the device in the target location. As seen in FIG. 11A, repair device 100 may be preformed to assume a curved shape or other non-straight shape when unconstrained in the deployed configuration. Accordingly, repair device 100 may be flexible and resilient so that it may be formed in a more linear shape when positioned in lumen 102 of catheter 104 and it will resiliently return to its preformed deployed configuration when released from the catheter. Alternatively or additionally, repair device 100 may be inflatable or fillable with a fluid material as further described below, and it may be configured to assume a predetermined deployed shape as a result of fluid pressure.

In the embodiment shown in FIG. 11A, the repair device 100 includes a support 110 for engaging and at least partially conforming to a subannular position between an interior surface of a heart chamber wall (e.g., a left ventricle wall) and a backside of a native valve leaflet (e.g., the mitral valve posterior leaflet). The support 110 can generally have a first end 112, a second end 114, and curved region 116 between the first and second ends 112, 114. In one embodiment, the support 110 can be positioned as close as possible to the valve annulus in the subannular region (e.g., at the highest point in the space between the outside-facing surface of the valve leaflet and the ventricular wall). The curved shape of the curved region 116 may accommodate and/or otherwise conform to the curved shape of the posterior mitral annulus, or it may be relatively stiff to encourage a specific shape. The length of the support 110 can extend substantially the entire distance between the commissures, or only part way around the posterior leaflet PL without reaching the commissures, or beyond one or both commissures so as to extend below a portion of the anterior leaflet AL. The support 110 is preferably configured to be wedged or retained by compression or friction with the underside (e.g., the outward-facing surface or downstream side) of the posterior leaflet PL and the inner wall of the ventricle, and/or engagement with the chordae tendineae attached to the posterior leaflet PL. In some embodiments the support 110 is configured to be positioned between the basal and/or tertiary chordae tendineae and the ventricular wall. The support 110 will preferably be sufficiently rigid to deflect the posterior leaflet PL to the desired post-treatment configuration, but still having some flexibility to allow it to flex and avoid tissue damage under high forces. The support 110 may also have some resilience and compressibility to remain engaged with the chordae tendineae, the leaflet and the wall tissue as the heart changes shape both acutely and long-term. The support can be a frame, bladder, balloon, foam, tube (e.g., a mesh tube), or other structure that is configured to extend (e.g., expand) at a target site in a manner that pushes or otherwise repositions a leaflet of a native valve from a pre-treatment position in which the native leaflets fail to coapt properly to a post-treatment position in which the leaflets coapt during a portion of the cardiac cycle. The support can be further configured to brace, support, or otherwise maintain the leaflet in the post-treatment position for at least a portion of the cardiac cycle, preferably permanently.

The support 110 can be pre-shaped such that upon deployment, the repair device 100 accommodates (e.g., approximates) the shape of the native anatomy or the desired post-treatment shape of the native anatomy. For example, the support 110 can be pre-shaped to expand into a "C" shape or other suitably curved shape to accommodate the curvature of the mitral valve annulus and/or to conform to a portion of the native mitral valve annulus. In some embodiments, several components of the support 110 can have a subannular engaging surface 118 that includes one or more peaks (not shown) and one or more valleys (not shown) in the upstream-downstream direction for accommodating or conforming to the native saddle-shape contour of the mitral annulus. An outer edge 117 of the curved region 116 of the support 110 can be positionable against the interior surface of the heart wall.

Referring to FIGS. 11A and 11B together, the support 110 can include a central spine 111 (e.g., a beam, a tube, or a frame) that may be a stent structure, such as a balloon-expandable or self-expanding stent. In other embodiments, the spine 111 can be a coiled spring, a braided tube, a wire, a polymeric member, or other form. The spine 111 and/or other portions of the support 110, in various embodiments, can include metal material such as nickel-titanium alloys (e.g. nitinol), stainless steel, or alloys of cobalt-chrome. In other embodiments, the support 110 can include a polymer such as Dacron®, polyester, polypropylene, nylon, Teflon®, PTFE, ePTFE, etc. Other suitable materials known in the art of elastic and/or expandable or flexible implants may be also be used to form some components of the support 110. As shown in FIG. 11A, several embodiments of the spine 111 can be formed, at least in part, from a cylindrical braid or stent structure comprising elastic filaments. Accordingly, the spine 111 and/or other portions of the support 110 can include an elastic, superelastic or other shape memory component that self-expands upon deployment of the device 100 to a formed or a preformed configuration at a target site. The spine 111 can further include a lumen 119 through which a guidewire (not shown) and/or strengthening/stiffening elements 115 (shown in FIG. 11B), such as wires, coils, or polymeric elements, can be placed into or integrated within the support 110. Such strengthening/stiffening elements 115 can be inserted into the lumen 119 before or during deployment of the repair device 100 to provide additional resistive pressure against the cardiac tissue once implanted. Spine 111 can be flexible and resilient so it can be straightened for delivery in a catheter or sheath or over a wire, and it can resiliently return to a curved shape (e.g., a curved shape similar to the native valve annulus) when unconstrained. In some embodiments, the spine 111 preferably has sufficient stiffness to structurally support the treated valve leaflet in the desired position and shape. In some embodiments, spine 111 may be covered with a biocompatible, flexible fabric or polymer, preferably one that allows tissue ingrowth.

The support 110 can further include an extension unit 120 attached to and/or positioned around at least a portion of the spine 111. In one embodiment, for example, the extension unit 120 can be biocompatible with cardiac tissue at or near the native valve of the patient so as to promote tissue ingrowth and strengthen implantation of the repair device 100 within the native valve region. In exemplary embodiments, extension unit 120 can comprise a flexible cover of biocompatible fabric or polymer that surrounds spine 111. In one embodiment, the extension unit 120 can include an expandable member, such as an expandable tube, balloon, bladder, foam or other expandable material, that is coupled to the spine 111. The expandable member may itself surround spine 111, may be held within a flexible fabric or polymeric cover extending around or attached to spine 111, or may be attached directly to a lateral side of spine 111. For example, the extension unit 120 can be an elastic or inelastic balloon made from impermeable, flexible biocompatible materials. The extension unit 120 can comprise a fabric or other flexible, stretchable and/or biocompatible material such as braided, woven, or crocheted Dacron®, expanded PTFE)(Gore-Tex®, bovine pericardium, or other suitable flexible material to integrate with adjacent tissue and promote tissue ingrowth to facilitate further stability of the repair device 100 in the subannular position. In other embodiments, the extension unit 120 can include polyester fabric, a polymer, thermoplastic polymer, a synthetic fiber, a natural fiber or polyethylene terephthalate (PET). Several embodiments of the extension unit 120 may be pre-shaped to accommodate a relatively fixed maximal dimension and shape when the repair device 100 is implanted. In various embodiments, the extension unit 120 can be porous and/or adhere to the interior surface of the heart wall and/or the backside of the leaflet. Tissue ingrowth into the extension unit 120 can form a pannus of tissue which is hemocompatible and can strengthen the combined structure of the repair device 100, the subannular tissue and/or interior surface of the heart wall, and the backside of the leaflet. Extension unit 120 will be expandable (e.g., in a transverse or radial direction relative to the longitudinal axis of the spine 111) from a collapsed configuration for endovascular or trans-apical delivery to an expanded configuration suitable for bracing the valve leaflet in the desired position. Extension unit 120 will usually be more flexible than spine 111 when in an unexpanded configuration, and in some embodiments will become substantially more rigid when expanded, e.g. by filling or inflating with a fluid. This rigidity may be imparted solely by fluid pressure, or by hardening or curing the fluid (e.g. epoxy or cement) within the extension unit.

The support 110 can further include a plurality of projections 130 and depressions 131 in the expanded configuration. The projections 130 alternate with depressions 131 such that each depression is disposed between two projections, forming a series of peaks and valleys. For example, the projections 130 can be features of the extension unit 120 that extend toward the other native leaflet and generally parallel to the underside of the supported leaflet such that the projections 130 extend between and engage the secondary and/or tertiary chordae tendineae that tether the leaflet (e.g., the mitral valve posterior leaflet) to the ventricular wall. In some embodiments all or a portion of the projections 130 may extend in generally the same (anterior) direction, while in other embodiments the projections 130 may extend in a radially inward direction relative to the curvature of the spine 111 (or native valve annulus). As such, a portion of the secondary and/or tertiary chordae tendineae can be positioned in the depressions 131 after the repair device 100 has been deployed. The upper or leaflet-facing sides of the projections 130 are preferably smooth and wide enough to support the leaflet without abrading or damaging the leaflet should it move or rub against the projections during the cardiac cycle. The depressions 131 are preferably wide enough to receive at least one of the chordae somewhat snugly to inhibit lateral movement of the support.

Referring still to FIGS. 11A-B and in accordance with an embodiment of the present technology, the extension unit 120 can include a plurality of pockets 132 that can be configured to receive filler material 140 during or upon deployment of the device 100 to form the projections 130. For example, a liquid that cures into a permanently semi-flexible or rigid material can be injected into the extension unit 120 to at least partially fill the pockets 132 of the extension unit 120 and thereby form the projections 130. In other embodiments, not shown, the pockets 132 can be expanded to form the projections 130 using internal elements such as segmented stents, one or more coiled spring elements, or other reinforcement structures. For example, the stent or spring might be pre-shaped to help the device 100 assume the deployed configuration (e.g., shape and profile). Accordingly, once in the deployed configuration, the projections 130 can be interspersed between the chordae tendineae CT.

The side of the support opposite the projections 130 (i.e., posterior side in mitral embodiments) will preferably be configured to atraumatically and compressively engage the ventricular wall to assist in anchoring the device in place. The posterior surface may be a soft, compressive, and resilient material, preferably atraumatic to the heart wall, and preferably one that encourages tissue in-growth. In some embodiments, the posterior side may have retention elements, e.g. spikes, hooks, bristles, points, bumps, or ribs, protruding from its surface, to engage the ventricular wall to further assist in anchoring and immobilizing the device. The posterior side may also have one or more expandable, resilient, or spring-like elements thereon that engage the ventricular wall and urge the support 110 in the anterior direction (away from the wall) to firmly and compressively engage the chordae tendonae between the projections 130. This can supplement or substitute for the expansion of the support 110 or extension member.

Figure 12A:
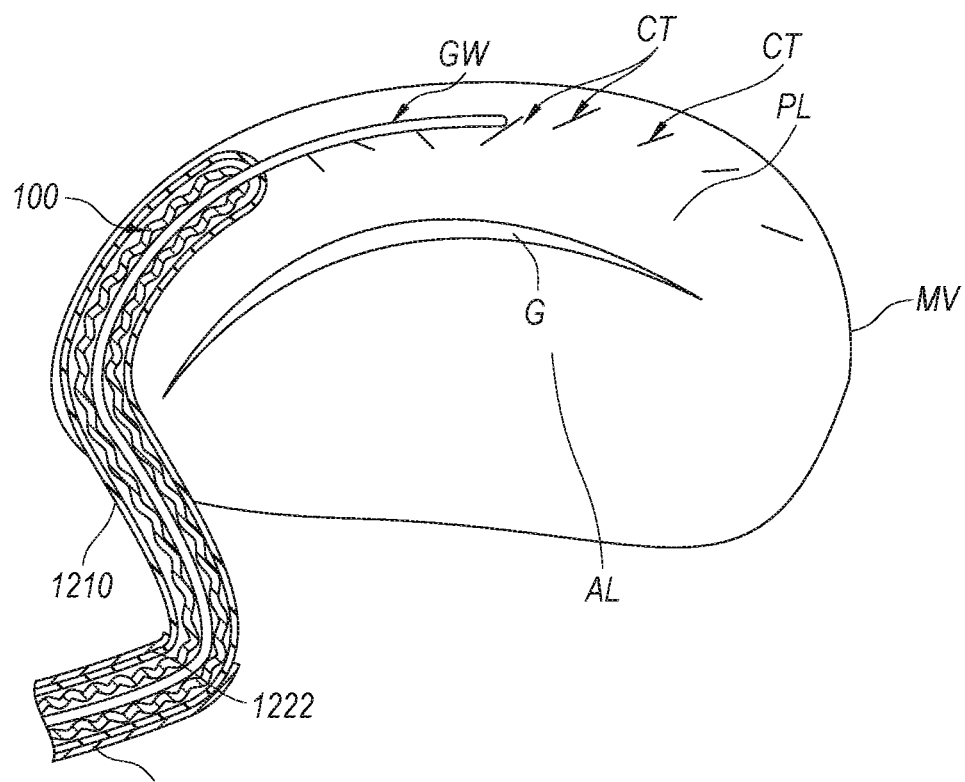
FIG. 12A is a cross-sectional top view of a prosthetic heart valve repair device and a delivery system at a stage of implanting the prosthetic heart repair valve device in accordance with an embodiment of the present technology.
Figure 12B:
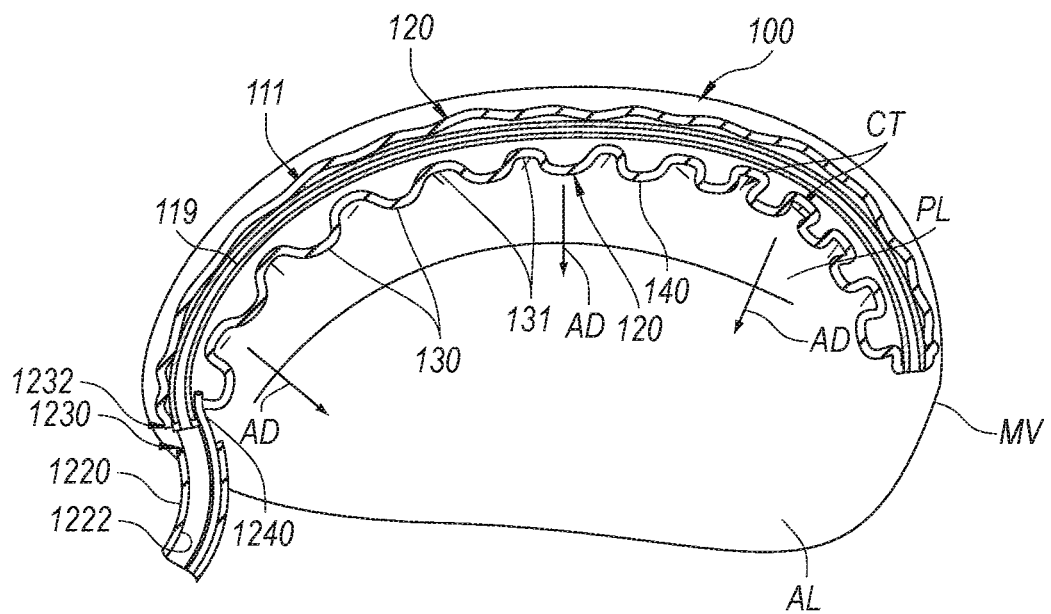
FIG. 12B is a cross-sectional top view of the prosthetic heart valve repair device and delivery system of FIG. 12A at a subsequent stage of implanting the prosthetic heart repair valve device in accordance with an embodiment of the present technology.

FIGS. 12A and 12B are cross-sectional top views of the repair device 100 and a delivery system at stages of implanting the repair device 100 (spine 111 removed for clarity in FIG. 12A) in accordance with an embodiment of the present technology. Referring to FIG. 12A, a guidewire GW is positioned at the implant site and a guide catheter 1210 is passed over the guidewire GW until the guide catheter 1210 is positioned at least proximate the valve. An optional delivery catheter or sheath 1220 can then be passed through the guide catheter 1210. The guidewire GW can be withdrawn, and the repair device 100 is then passed through the guide catheter 1210 or the optional sheath 1220. In another embodiment, the guidewire GW is received in the lumen 119 (FIGS. 11A and 11B) of the repair device 100 such that the repair device 100 passes over the guidewire GW during implantation. When the repair device 100 is used to repair a native mitral valve MV, the guidewire GW can be positioned under the posterior leaflet PL of the native mitral valve MV, the guide catheter 1210 and/or optional sheath 1220 are then placed at a target site under the posterior leaflet PL, and then the repair device 100 is positioned within the guide catheter 1210 and/or the optional sheath 1220 at the target site. At this stage, the anterior and posterior leaflets fail to coapt, resulting in a gap G between the posterior leaflet PL and the anterior leaflet AL.

FIG. 12B shows a subsequent stage of implanting the repair device 100 under the posterior leaflet PL of the native mitral valve MV. The sheath 1220 can have a lumen 1222, and the repair device 100 can be attached to a shaft 1230 by a release mechanism 1232. Additionally, an inflation tube 1240 can extend along or through the sheath 1220 and through a one-way valve (not shown) into the extension unit 120 of the support 110. In one embodiment, the repair device 100 is contained in a radially collapsed state in the lumen 1222 of the sheath 1220 as the repair device 100 is positioned under the posterior leaflet PL, and then the sheath 1220 is retracted proximally to expose the repair device 100 at the target site. After the repair device 100 has been exposed, the filler material 140 is injected into the extension unit 120 via the inflation tube 1240 causing the projections 130 to extend away from the spine 111 towards the central axis of the valve orifice (arrows AD). The projections 130 accordingly push at least the free edge of the posterior leaflet PL toward the anterior leaflet AL until the gap G (FIG. 12A) at least partially closes to enhance the competency of the native mitral valve MV. In the embodiment shown in FIG.

12B, the gap G is completely eliminated such that the free edge of the posterior leaflet PL fully coapts with the free edge of the anterior leaflet AL. Additionally, the chordae tendineae CT positioned in the depressions 131 between the projections 130 secure the repair device 100 in the subannular space. The release mechanism 1232 is then activated to separate the repair device 100 from the shaft 1230. The sheath 1220 along with the shaft 1230 and inflation tube 1240 are then withdrawn from the patient.

In other embodiments, the repair device 100 may include a fluid absorbing material that expands after implantation by absorption of blood or other fluids to inflate the extension unit 120 either in addition to or in lieu of using the inflation tube 1240. For example, the extension unit 120 may have a fluid permeable cover and an absorbent material within the cover that expands as it absorbs fluid, or the extension unit 120 can be a foam that expands to form the projections 130. Alternatively, the extension unit 120 may be filled with a fluid absorbing substance such as a biocompatible hydrogel which expands when exposed to blood or other fluid. In this way, the support 110 may be implanted and optionally expanded partially, then allowed to expand to its fully expanded configuration by absorption of fluids. Alternatively, the extension unit 120 may be sufficiently porous to allow blood to pass into it such that blood will collect and fill up the extension unit. Eventually, the blood may clot and be replaced by tissue to strengthen and rigidify the repair device 100. In further embodiments, the extension unit 120 may be configured to receive an injectable material to realize a fully-expanded configuration.

Figure 13:
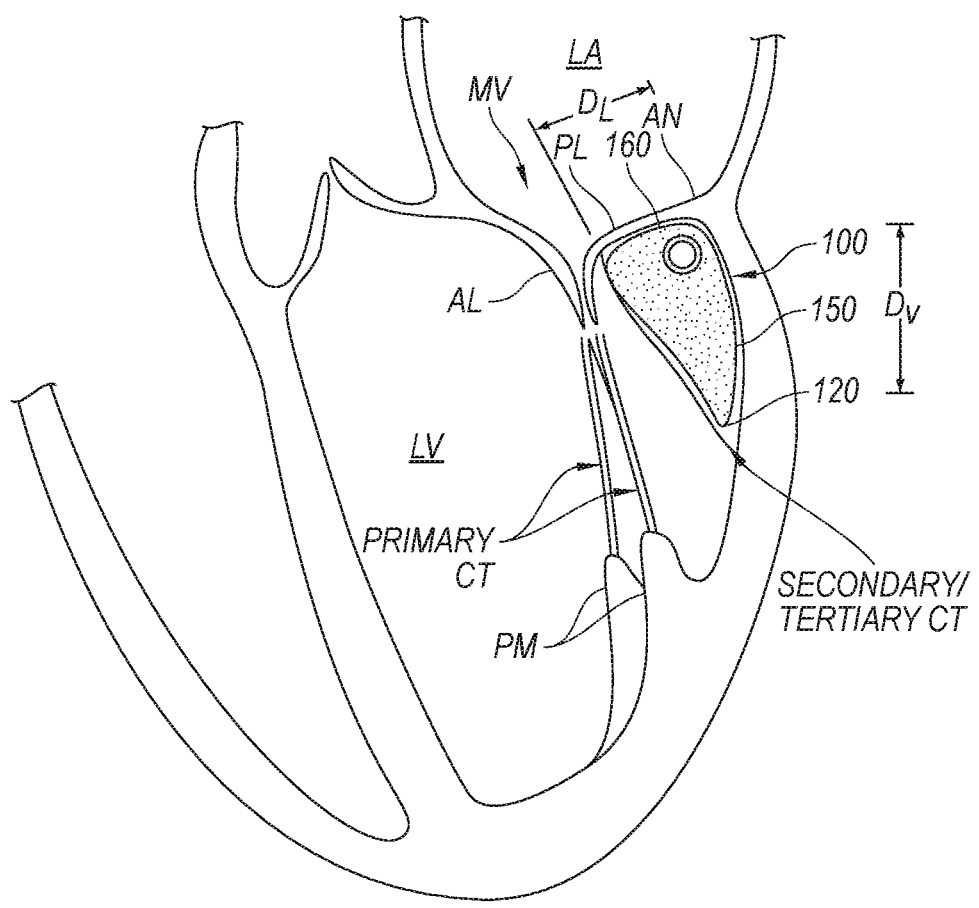
FIG. 13 is a cross-sectional view schematically illustrating a left atrium, left ventricle, and native mitral valve of a heart with an embodiment of a prosthetic heart valve repair device implanted in the native mitral valve region in accordance with an embodiment of the present technology.

FIG. 13 is a cross-sectional view schematically illustrating a left atrium, left ventricle, and native mitral valve of a heart with an embodiment of the repair device 100 implanted in the native mitral valve region. In this embodiment, the repair device 100 is implanted in a subannular position and behind the posterior leaflet PL of the native mitral valve MV at the ventricular side of the mitral annulus AN as described above with reference to FIGS. 12A and 12B. The repair device 100, for example, can have a ventricular wall engaging surface 150 that engages the ventricular wall along a distance $D_V$ and a posterior leaflet engaging surface 160 configured to engage the outward-facing surface (e.g., underside or downstream side) of the posterior leaflet PL. The repair device 100 is retained in this subannular position by the chordae tendineae CT (e.g., the basal or tertiary chordae tendineae which are associated with the posterior leaflet PL closest to the annulus AN). As repair device 100 is expanded from a collapsed, delivery configuration to an expanded, deployed configuration, the width or area of the posterior leaflet engaging surface 160 enlarges. In some embodiments, repair device 100 can be expanded until the posterior leaflet engaging surface has the desired width or area, e.g., until the posterior leaflet is repositioned and/or reshaped such that it coapts with the anterior leaflet and regurgitation through the valve is reduced or eliminated. As shown in FIG. 13, when the device 100 is in the deployed configuration, the posterior leaflet engaging surface 160 engages the outward-facing surface (e.g., underside) of at least the posterior leaflet PL along a distance $D_L$ from the posterior wall of the ventricle toward the anterior leaflet AL to push, brace or otherwise support the posterior leaflet PL such that it coapts with the anterior leaflet AL and/or otherwise reduces mitral valve regurgitation (e.g., drives the posterior leaflet PL toward the anterior leaflet AL into at least a partially closed position). The distance $D_L$ can be selected or controlled to adapt the repair device 100 to the specific anatomy of the patient. In several embodiments, the distance $D_L$ is from about 2-20 mm, preferably at least about 8 mm, or in other embodiments from about 8 to about 12 mm. In some embodiments, the device 100 can support the posterior leaflet PL in a fully closed position, and in further embodiments the repair device 100 can extend the posterior leaflet PL toward the anterior leaflet to a closed position that extends beyond the leaflet's naturally closed position. For example, the shape of the posterior leaflet PL may be changed by expanding the repair device 100 to push it toward or bracing it in a position closer to the anterior leaflet AL. In one example, the repair device 100 can have a triangular or polygonal cross-section for engaging the ventricular wall, the annulus AN, and the outward-facing surface of the posterior leaflet PL. In other embodiments, the repair device 100 can have a circular, oval, elliptical, or oblong cross-section.

Figure 14A:
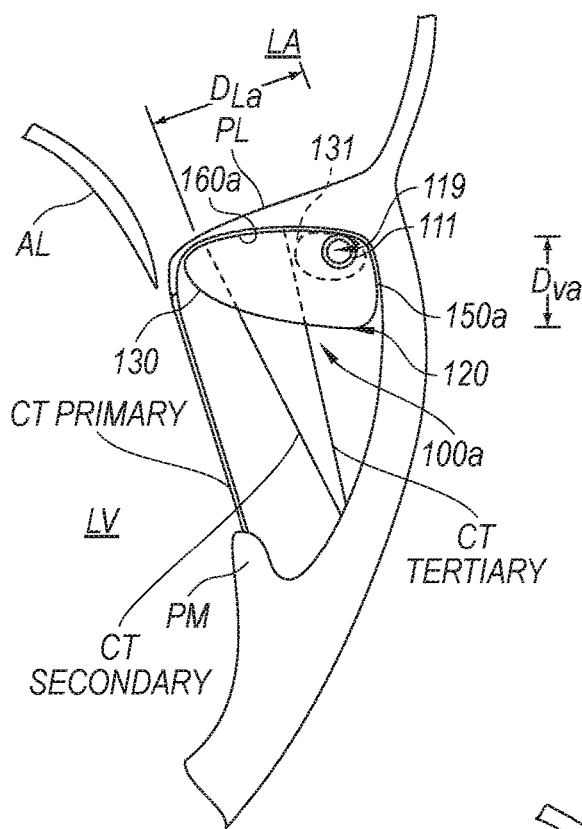
FIG. 14A is a cross-sectional view schematically illustrating a portion of a left atrium, left ventricle, and native mitral valve of a heart with an embodiment of a prosthetic heart valve repair device implanted in the native mitral valve region in accordance with an embodiment of the present technology.

The overall cross-sectional shape of the repair device 100 can determine the resting location of the posterior leaflet PL as it is braced in the at least partially closed position. Therefore, the distances $D_V$ and $D_L$, and the curvatures of the ventricular wall engaging surface 150 and the posterior leaflet engaging surface 160, can be configured to accommodate different anatomical requirements of different patients. For example, FIG. 14A shows another embodiment of a repair device 100a similar to the repair device 100 illustrated in FIG. 13, but in the deployed configuration the repair device 100a includes a ventricular wall engaging surface 150a with a vertical or cranial-caudal distance $D_{Va}$ that is less than the corresponding distance $D_V$ of the ventricular wall engaging surface 150 of the repair device 100 shown in FIG. 13. The repair device 100a further includes a posterior leaflet engaging surface 160a that contacts the underside of the posterior leaflet PL along posterior-anterior dimension by a distance $D_{La}$ greater than that of the posterior engaging surface 160 of the repair device 100 of FIG. 13. As such, the repair device 100a is able to support the posterior leaflet PL in a position closer to the anterior leaflet AL than the device 100; the repair device 100, more specifically, can move the line along which posterior leaflet PL hinges to open and close away from the posterior heart wall of the left ventricle and closer to the anterior leaflet AL to reduce the size of the movable portion of the posterior leaflet that opens and closes during the cardiac cycle. The leaflet hinge may alternatively be eliminated altogether so that the leaflet is substantially stationary throughout the cardiac cycle.

Figure 14B:
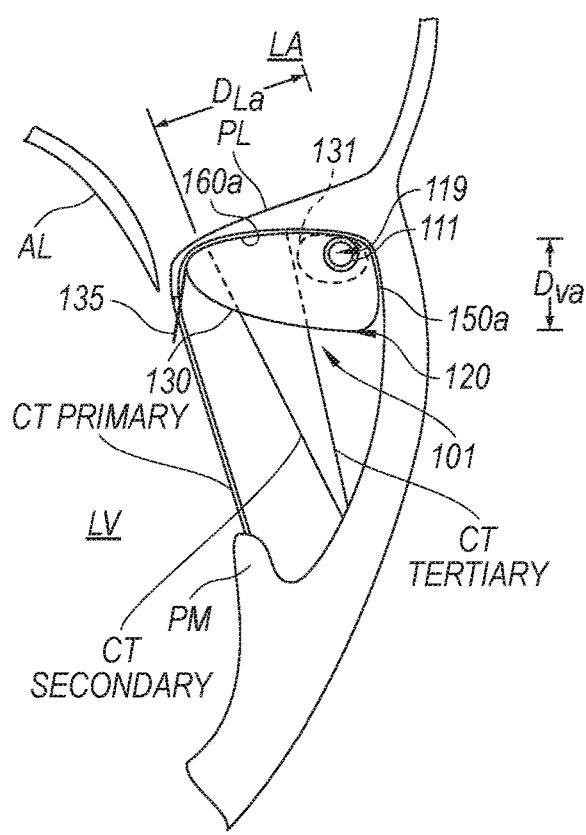
FIG. 14B is a cross-sectional view schematically illustrating a portion of a left atrium, left ventricle, and native mitral valve of a heart with an additional embodiment of a prosthetic heart valve repair device implanted in the native mitral valve region in accordance with an embodiment of the present technology.
Figure 15:
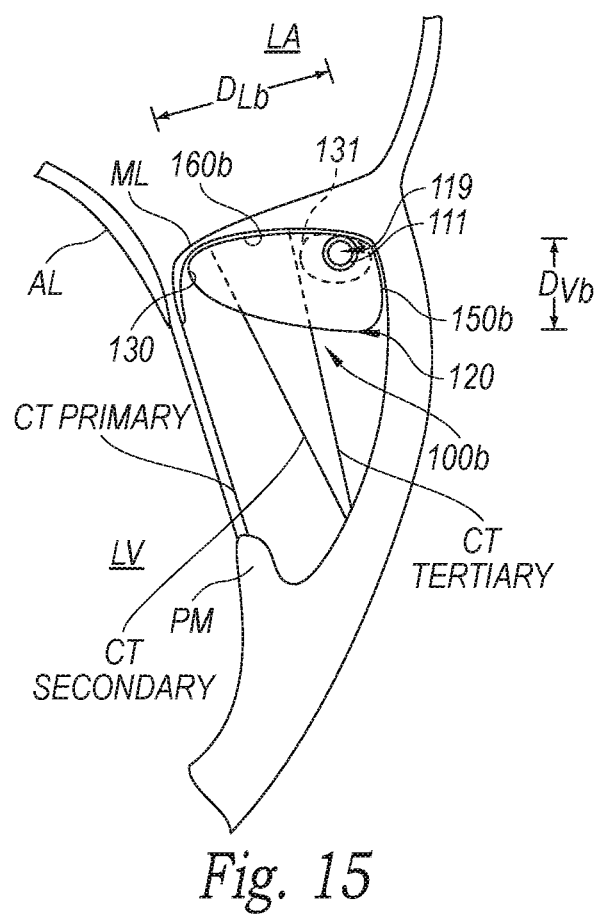
FIG. 15 is a cross-sectional view schematically illustrating a portion of a left atrium, left ventricle, and native mitral valve of a heart with an embodiment of a prosthetic heart valve repair device implanted in the native mitral valve region in accordance with an embodiment of the present technology.

FIG. 14B illustrates yet another embodiment of a repair device 101 similar to the repair devices 100 and 100a illustrated in FIGS. 13 and 14A, respectively, but in the deployed configuration the repair device 101 includes an appendage 135, such as an apron or flap. The appendage 135 is positioned such that it extends (e.g., hangs) down beyond an edge of the posterior leaflet PL to extend the posterior leaflet toward the anterior leaflet AL. The appendage 135 is positioned behind the chordae tendineae CT in some areas, but is expected to be effective in extending the posterior leaflet PL between the two groups of chordae. In some embodiments, this feature is expected to help reduce or inhibit mitral regurgitation by closing the posterior leaflet PL and drawing its edge close to the anterior leaflet AL. It is expected that the appendage 135 is useful when the posterior leaflet PL and anterior leaflet AL are separated by a large distance.

configured in accordance with another embodiment of the present technology. The repair device 100b shown in FIG. 15 is similar to the repair device 100a shown in FIG. 14A, but 100b in the deployed configuration is flatter (shorter in the atrial-ventricular direction) than the repair device 100*a*. For example, the repair device 100*b* has a ventricular wall engaging surface 150*b* that engages the ventricular wall along a distance $D_{Vb}$ that is less than the distance $D_{Va}$ of the repair device 100*a*. The repair device 100*b* may be easier to implant than the repair device 100*a* because the lower profile of the repair device 100*b* can fit in a smaller delivery catheter and in the tight spaces between the ventricular heart wall and the chordae tendineae CT.

Figure 16A:
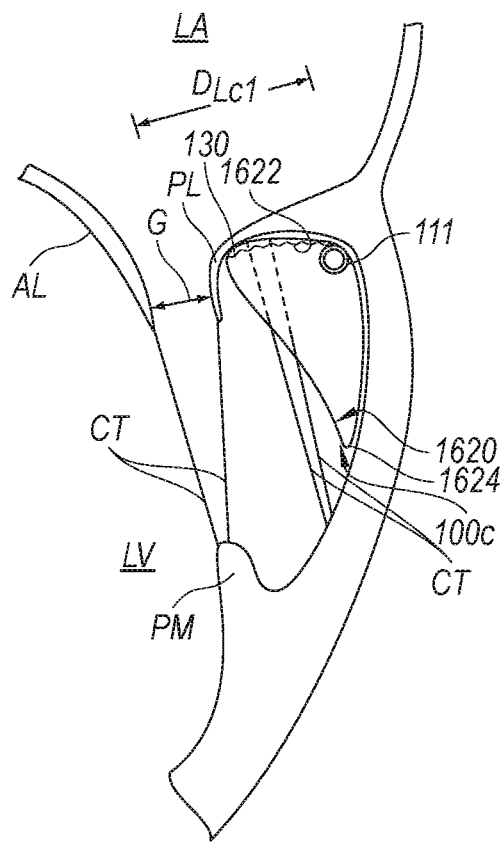
FIGS. 16A and 16B are cross-sectional views schematically illustrating a portion of a left atrium, left ventricle, and native mitral valve of a heart with an embodiment of a prosthetic heart valve repair device implanted in the native mitral valve region in accordance with an embodiment of the present technology.
Figure 16B:
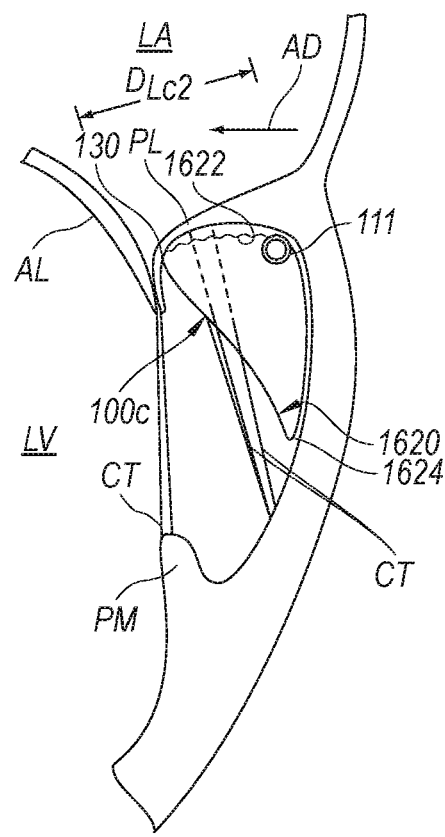

FIGS. 16A and 16B are cross-sectional side views of a repair device 100*c* configured in accordance with another embodiment of the present technology. In this embodiment, the repair device 100*c* has an extension unit 1620 including a bellows 1622 that preferentially expands in the anterior direction AD. The bellows 1622 can be an accordion style portion of the extension unit 1620, and the remainder of the extension unit 1620 can be a flexible fabric or polymeric material that is made from the same material as the bellows 1622 or a different material. In other embodiments, the portion of the extension unit 1620 other than the bellows 1622 can be made from a metal or other material that can flex at a lower bend 1624. In operation, as the extension unit 1620 is inflated, the bellows 1622 allows the projection 130 to move in the anterior direction AD such that the repair device 100*c* engages the underside of the posterior leaflet PL by an increasing distance (e.g., $D_{Lc1}$ in FIG. 16A to $D_{Lc2}$ in FIG. 16B).

Figure 17A:
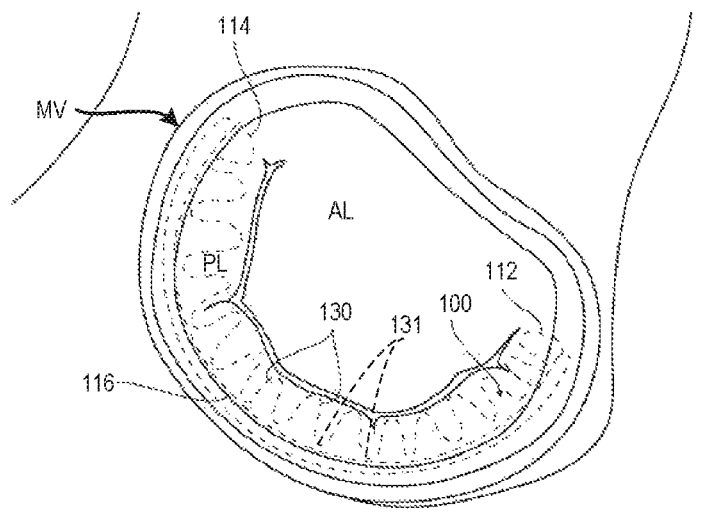
FIGS. 17A-17C are schematic top views of a native mitral valve in the heart viewed from the left atrium and showing a heart valve repair device implanted at the native mitral valve in accordance with additional embodiments of the present technology.
Figure 17B:
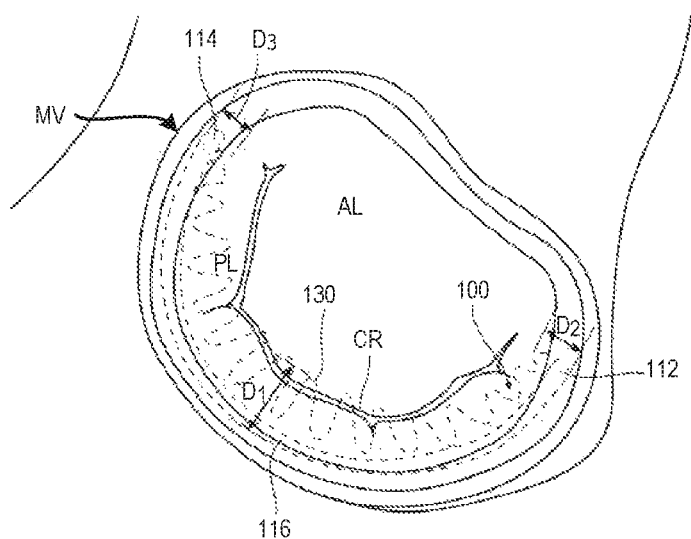
Figure 17C:
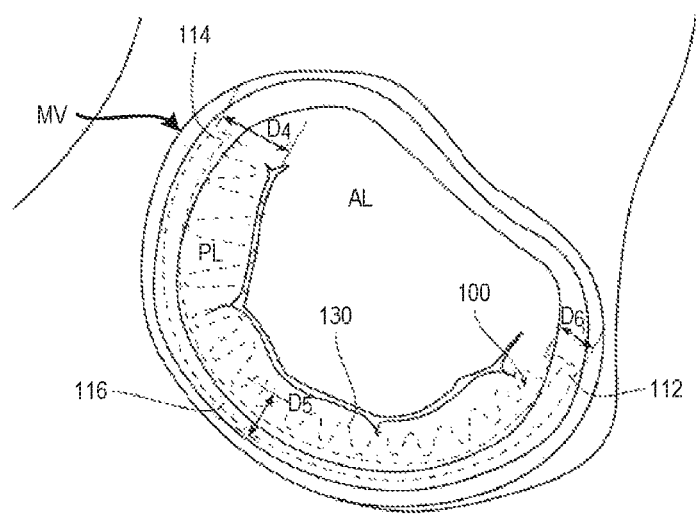

FIGS. 17A-17C are schematic top views of a native mitral valve MV in the heart viewed from the left atrium and showing an embodiment of any of the repair devices 100-100*c* described above implanted at the native mitral valve MV in accordance with additional embodiments of the present technology (repair devices 100-100*c* are identified collectively as "repair device 100" and shown in dotted lines with respect to FIGS. 17A-17C). The presence of the projections 130 may allow the repair device 100 to expand fully for supporting or bracing the outward-facing surface of the posterior leaflet PL in at least a partially closed position without tearing or excessively displacing or stretching the chordae tendineae which retain the repair device 100 at the target implantation location. In some embodiments, the chordae tendineae also help retain the repair device 100 in a desired cross-sectional shape. The projections 130 may be configured to extend anteriorly or radially along the underside of posterior leaflet PL through gaps between the basal or tertiary chordae by a sufficient distance to brace the posterior leaflet PL in the desired position for effective coaptation. The distal tips of the projections 130 are preferably rounded and smooth to avoid trauma to the leaflet and to allow the leaflet to bend or fold around the projections 130 in the partially closed position. The projections 130 may also have structures, materials, or coatings thereon to engage and retain the chordae tendineae such that the projections 130 will not pull out in the reverse direction. For example, the projections 130 may have an enlarged head or T-shape at their distal ends, scales or backward-pointing tines along their sidewalls, or other features that allow the projections 130 to slide easily between the chordae tendineae in one direction but to resist movement in the other. The projections 130 may also be coated with a tissue in-growth promoting agent. In some embodiments, the device 100 can include other materials that encourages tissue ingrowth and/or tissue healing around the device such that the depressions 131 between the projections 130 may be filled with tissue (e.g., pannus of tissue) leaving a relatively smooth surface exposed to the left ventricle.

As shown in FIG. 17A, the repair device 100 can have a relatively consistent cross-sectional dimension over the length of the device (e.g., at the first and second ends 112, 114 and along the curved region 116). In a different embodiment shown in FIG. 17B, the curved region 116 device 100 can have a cross-sectional dimension $D_1$ that is larger than cross-sectional dimensions $D_2$, $D_3$ at the first and second ends 112, 114, respectively. In this embodiment, the larger cross-sectional dimension $D_1$ may assist the coaptation of the posterior leaflet PL with the anterior leaflet AL in the central region CR of the native mitral valve MV. In other embodiments, the device 100 can be configured to have larger cross-sectional dimensions at one or more ends (e.g., first and/or second ends 112, 114). For example, FIG. 17C shows a repair device 100 having an asymmetric cross-section profile. As shown in FIG. 17C, the repair device can have a second end 114 having a cross-sectional dimension $D_4$ that is larger than cross-sectional dimensions $D_5$ and $D_6$ of the curved region 116 and the first end 112, respectively. Accordingly, the repair device 100 can include a variety of dimensions (e.g., cross-sectional dimensions) and shapes that can be used to address a specific heart valve morphology of a patient. For example, the device 100 could be shaped and sized to repair areas of regurgitation within the native valve while preserving functionality of the leaflets (e.g., posterior leaflet function) to the extent possible in healthy areas of the native valve. In alternative embodiments, the device 100 may have a plurality of expandable, inflatable, or fillable regions or pockets arranged along the length of the device which can be independently expanded by injection of fluid to create regions of different cross-sectional size or shape along the length of device 100. In some embodiments, each of these regions or pockets could be selectively expanded as the heart continues to beat until the posterior leaflet is positioned and shaped as needed to reduce or eliminate regurgitation through the valve.

Repair devices in accordance with any of the foregoing embodiments can have other shapes, dimensions, sizes and configurations to address patient specific anatomy or to otherwise achieve coaptation of the native valve leaflets in a specific patient. The shape and dimension of the repair device 100 may be selected such that the posterior leaflet is braced in a position which results in sealing coaptation of the posterior and anterior leaflets during systole. The repair device 100 may be adjustable in size or shape before or after placement to allow the physician to adjust the device to achieve the desired post-treatment leaflet position. For example, the repair device 100 may have malleable portions that can be manually shaped by the physician, mechanically articulating portions that can be remotely adjusted, or inflatable portions into which a fluid may be injected to change their shape or size.

One aspect of several embodiments of the repair devices 100-100*c* described above is that the support 110 is secured at the target site without anchors or other components that pierce the tissue of the leaflets, annulus and/or the wall of the heart. For example, the combination of expanding or otherwise extending the projections 130 between the chordae tendineae and pressing the support 110 against the underside of the posterior leaflet and the wall of the left ventricle securely holds the repair device in place. This is expected to simplify the treatment and reduce trauma to the heart.

In other embodiments, repair device 100 may have features on its exterior to enhance fixation with the native tissue. For example, the posterior surface that engages the wall of the ventricle, and/or the upper surface that engages the posterior leaflet, may have barbs, bumps, ribs, spikes, or other projections configured to engage the tissue and enhance fixation through friction or by penetration of the tissue surface. Additionally or alternatively, friction-enhancing fabrics, polymers or other materials may be provided on these surfaces. In other embodiments, loops or hooks may be coupled to repair device 100 which are configured to engage with or extend around the chordae or papillary muscles. Further, the material used to cover repair device 100 may enhance tissue ingrowth such that the device is encapsulated in tissue within a short time after implantation.

Another aspect of several embodiments of the repair devices 100-100c is that the degree to which the projections 130 of the extension unit 120 extend in an anterior direction can be controlled to custom tailor the repair device 100 to the anatomy of a specific patient. For example, when the extension unit 120 is an inflatable bladder or balloon, the distance that the projections 130 extend in the anterior direction can be controlled by the amount of filler material 140 that is injected into the extension unit 120. This is expected to provide enhanced flexibility and customization of the repair device 100.

Figure 18:
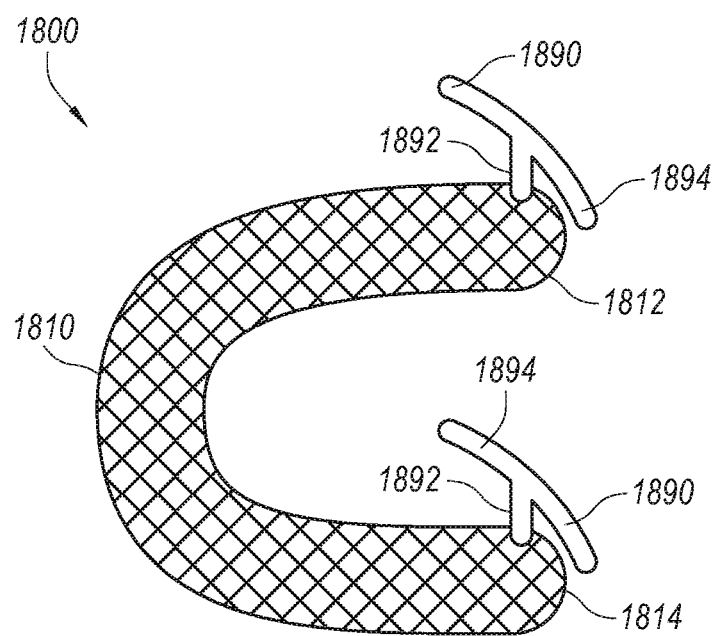
FIG. 18 is a perspective view of a prosthetic heart valve repair device in an expanded configuration in accordance with another embodiment of the present technology.

FIG. 18 is a perspective view of another embodiment of a repair device 1800 having a curved support 1810 with a first end 1812 and a second end 1814. The support 1810 may be similar to or the same as any of the supports 110 described above. The repair device 1800 further includes retention elements 1890 projecting from the support 1810 to enhance anchoring to the native tissue. Each retention member can have a post 1892 configured to extend through the opening between the valve leaflets and a cross-member 1894 configured rest on a upstream side or exterior surface of the valve leaflets. The retention elements 1890 may have a T-shape as shown in FIG. 18, lollipop shape, arrowhead shape, or other suitable structure to resist passing back between the leaflets. Optionally, the retention elements 1890 may be configured to press against, frictionally engage with, or penetrate the tissue of the native annulus, posterior leaflet, or atrial wall. In still other embodiments, the retention elements 1890 may be configured to engage and optionally penetrate into the ventricular wall. For example, a ventricular wall-engaging surface of the repair device may have one or more retention members in the form of spikes, barbs, ridges, bumps, hooks, or other frictional or wall-penetrating structures disposed thereon. Such retention members can be delivered through a central lumen of the repair device 1800 after placement, or be automatically deployed as the repair device 1800 expands.

Figure 19:
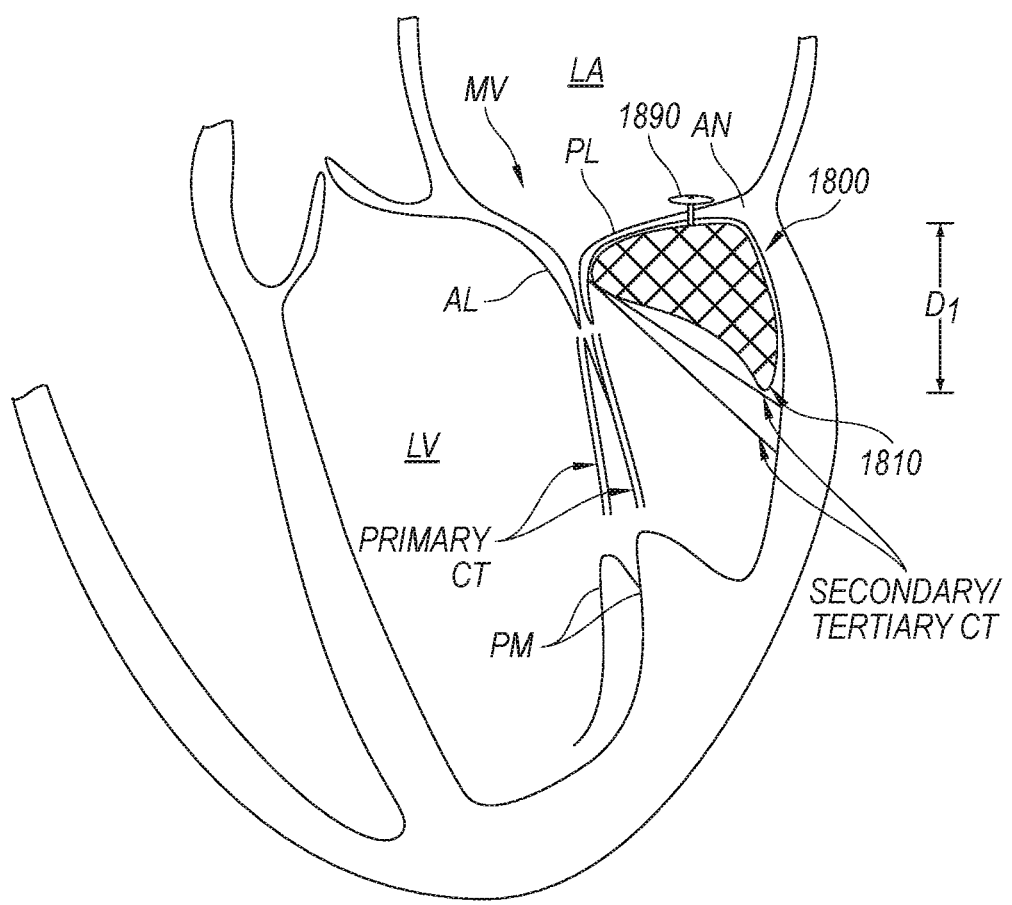
FIG. 19 is a cross-sectional view schematically illustrating a left atrium, left ventricle, and native mitral valve of a heart with a prosthetic heart valve repair device implanted in the native mitral valve region in accordance with an embodiment of the present technology.

FIG. 19 is a side cross-sectional view of the repair device 1800 after the repair device has been implanted under the posterior leaflet PL of a native mitral valve MV. In this embodiment, the retention elements 1890 extend from the support 1810 between the leaflets to an upstream or superannular side of the leaflets. Preferably, the retention elements 1890 are mounted near the ends 1812, 1814 of the support 1810 so as to extend through the commissures of the valve to the upstream side (shown in more detail in FIG. 20C below). Alternatively, the retention elements 1890 can penetrate through the leaflet itself (shown in more detail in FIG. 19).

Figure 20A:
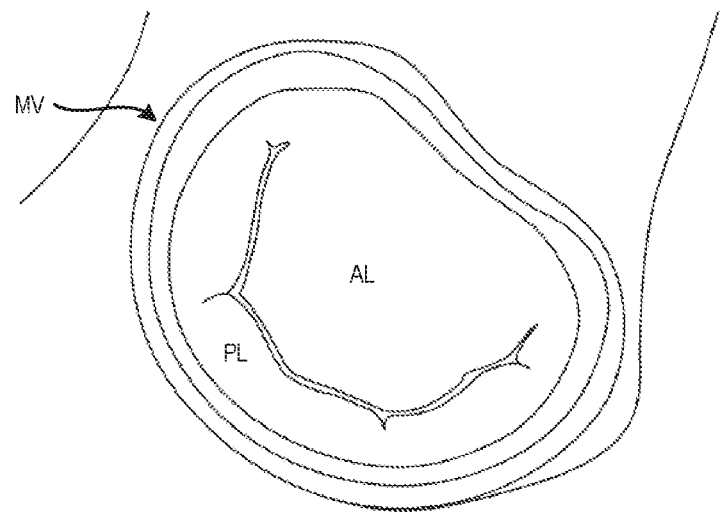
FIG. 20A is a schematic top view of a native mitral valve in the heart viewed from the left atrium and showing normal closure of native mitral valve leaflets.
Figure 20B:
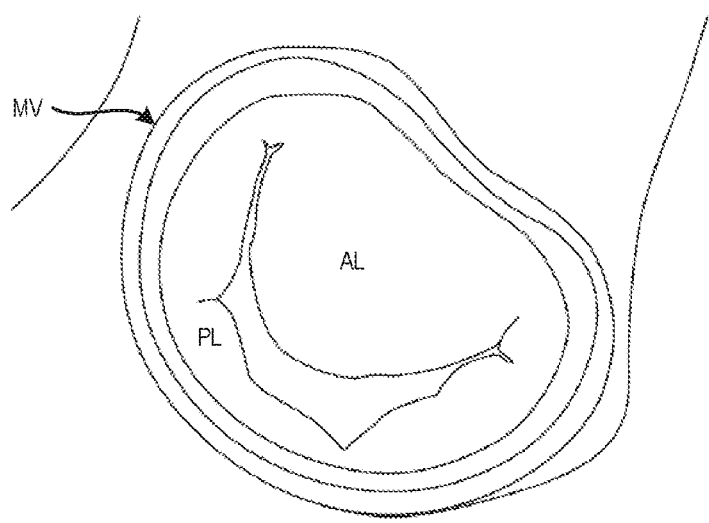
FIG. 20B is a schematic top view of a native mitral valve in the heart viewed from the left atrium and showing abnormal closure of native mitral valve leaflets, and which is suitable for combination with various prosthetic heart valve repair devices in accordance with embodiments of the present technology.
Figure 20C:
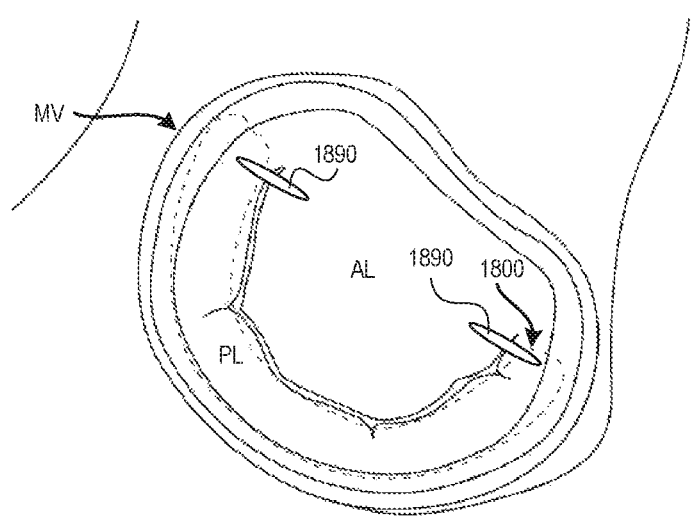
FIG. 20C is a schematic top view of a native mitral valve in the heart viewed from the left atrium and showing a heart valve repair device implanted at the native mitral valve in accordance with an embodiment of the present technology.

FIG. 20A is a schematic top view of a native mitral valve MV in the heart viewed from the left atrium and showing normal closure of a native posterior leaflet (PL) and a native anterior leaflet (AL), and FIG. 20B is a schematic top view of a native mitral valve MV in the heart viewed from the left atrium and showing abnormal closure of the posterior and anterior leaflets PL, AL. In FIG. 20B, the posterior leaflet PL fails to sufficiently coapt with the anterior leaflet AL, which in turn allows blood to regurgitate through the valve. FIG. 20C is a schematic top view showing an embodiment of the repair device 1800 (shown in dotted lines) implanted at a subannular location of the otherwise abnormally closed native mitral valve MV of FIG. 20B in accordance with an embodiment of the present technology. As shown in FIG. 20C, after the repair device 1800 is deployed behind the posterior leaflet PL in the subannular position, the repair device 1800 braces the posterior leaflet PL from the backside surface of the leaflet to support the leaflet in at least a partially closed position in which it sufficiently coapts with the anterior leaflet AL to reduce or eliminate regurgitation. The posterior leaflet PL in this example is braced such that it remains in a substantially closed position and is substantially prevented from moving away from the anterior leaflet AL during the cardiac cycle. The anterior leaflet AL can continue to open and close during diastole and systole, respectively. The repair device 1800 includes one or more retention elements 1890 as described above with respect to FIGS. 18 and 19. For example, the retention elements 1890 are shown extending through the commissures of the valve to the upstream side.

Various aspects of the present technology provide heart valve repair devices that can reduce the effective annular area of the mitral valve orifice, by holding the posterior leaflet permanently closed, or in other embodiments mostly closed, or in further embodiments in an extended position beyond its natural closed position state. When the repair device is deployed at the target region of the mitral valve, the native valve may have only a functional anterior leaflet, thereby reducing the effective orifice area. Not to be bound by theory, the remaining effective orifice area is believed to be sufficient to avoid a physiologically detrimental or an excessive pressure gradient through the mitral orifice during systole. Regurgitant mitral valves typically have dilated to a size much larger than their original area, so a reduction in the orifice area may not compromise the valve. Additionally, many conventional mitral valve repair surgeries result in a posterior leaflet that extends only a very short distance from the posterior annulus. After these surgeries, the motion of the anterior leaflet provides nearly all of the orifice area. Accordingly, immobilization of the posterior leaflet of a dilated mitral valve in the closed position is not believed to lead to hemodynamic complications due to a high pressure gradient during antegrade flow through the valve.

Following implantation and deployment of the repair device in the target location, and while the device extends and holds the posterior leaflet of the mitral valve at least partially in the closed position, the device additionally can apply tension from the valve leaflet to the chordae tendineae attached to the papillary muscles and the ventricular wall. This additional tension applied by the implanted repair device can, in some embodiments, pull the papillary muscles and the free wall of the left ventricle closer to the mitral valve to reduce the tethering effect on the anterior leaflet and allow the anterior leaflet to close more effectively. Thus, in addition to the hemodynamic benefit of a competent mitral valve by at least partially closing the posterior leaflet, the device might slightly improve morphology of both the anterior leaflet and the left ventricle, and help the valve to provide a structural benefit to the ventricle.

In another aspect of the present technology, several embodiments of the repair device 100 can be used in conjunction with a prosthetic heart valve replacement device delivered percutaneously or trans-apically to treat an abnormal or diseased native heart valve. Percutaneous or transapical replacement of the mitral valve is particularly challenging due, at least in part, to the non-circular, large, and asymmetric shape of the mitral annulus. In addition, a diseased mitral valve can enlarge over time making implantation of a percutaneous prosthetic heart valve even more challenging. In accordance with an embodiment of the present technology, the repair device 100 can be configured to change either an annulus shape or an annulus cross-sectional dimension when the device 100 is in the deployed configuration. In a particular example, the repair device 100 can be implanted in the sub annular position behind a posterior leaflet PL of a native mitral valve MV to decrease the effective size of the mitral valve annulus. In another embodiment, the repair device 100 can be configured to change the native annulus shape to a more circular shape or having a circular orifice, which may be advantageous for receiving some variations of implantable prosthetic heart valves. In one embodiment, the repair device 100 may be implanted in a first surgical step and implantation of a prosthetic heart valve device may occur at a second surgical step either immediately or at some future date.

Figure 21A:
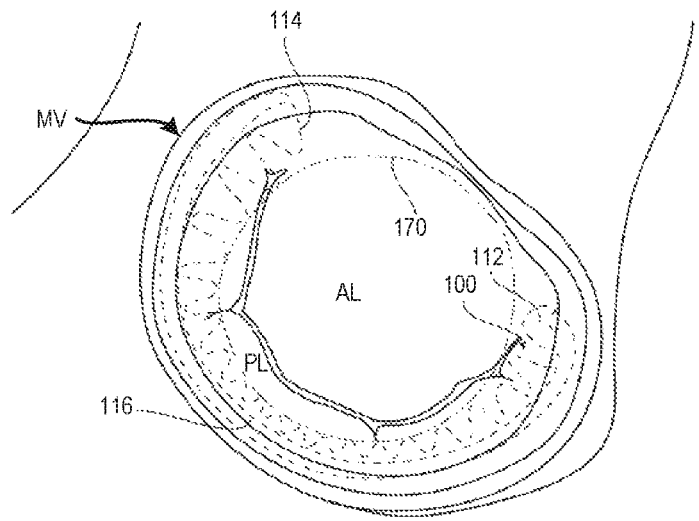
FIG. 21A is a schematic top view of a native mitral valve in the heart viewed from the left atrium and showing a heart valve repair device implanted at the native mitral valve in accordance with a further embodiment of the present technology.
Figure 21B:
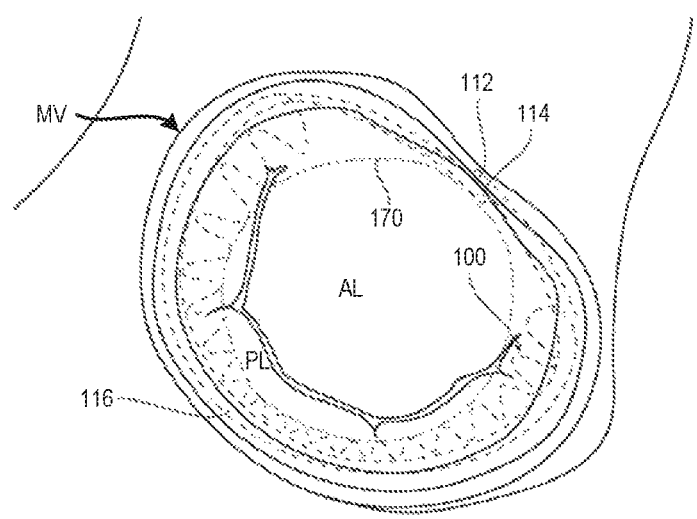
FIG. 21B is a schematic top view of a native mitral valve in the heart viewed from the left atrium and showing a heart valve repair device implanted at the native mitral valve in accordance with another embodiment of the present technology.

FIG. 21A is a schematic top view of a native mitral valve MV in the heart viewed from the left atrium and showing a heart valve repair device 100 (shown in dotted lines) implanted at the native mitral valve wherein the opposing ends 112, 114 of the repair device 100 extend beyond the native valve commissures of the posterior leaflet PL. In this embodiment the first and second ends 112, 114 can support at least a portion of the anterior leaflet AL and/or create a smaller and/or circular native mitral valve orifice 170 for receiving a replacement heart valve device. FIG. 21B illustrates another embodiment of a heart valve repair device 100 (shown in dotted lines) implanted at the native mitral valve MV, wherein the repair device 100 has first and second ends 112, 114 that extend beyond the native valve commissures and meet, overlap and/or join behind the anterior leaflet AL. Additional strengthening and/or stiffening materials (e.g., nitinol, stainless steel, etc.) can be used, in some embodiments, to hold the ends 112, 114 in desired locations behind the anterior leaflet AL. In the embodiment shown in FIG. 21B, the device 100 can either partially or fully support the subannular region behind the anterior leaflet AL as well as partially or fully support the anterior leaflet AL to effectively shrink the effective annular area and/or create a smaller and/or more circular native mitral valve orifice 170 for receiving a replacement heart valve device.

Figure 21C:
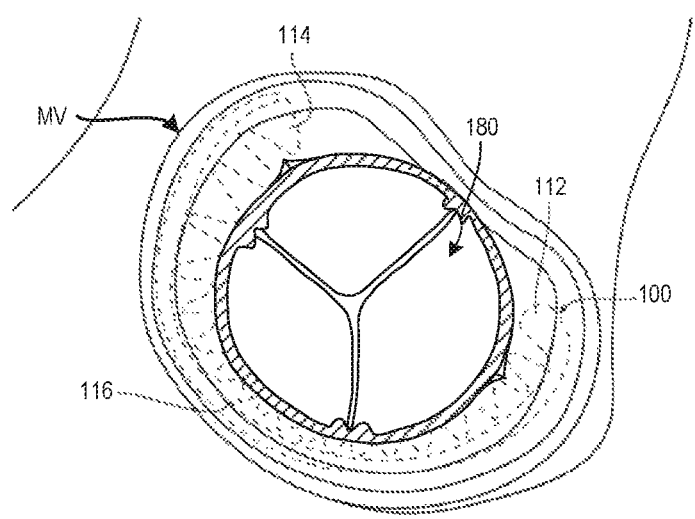
FIG. 21C is a schematic top view of a native mitral valve in the heart viewed from the left atrium and showing the heart valve repair device of FIG. 21A and a prosthetic heart valve implanted at the native mitral valve in accordance with an embodiment of the present technology.

In one example, the smaller and/or circular native mitral valve orifice 170 may be able to accommodate valve prostheses designed for implantation in circular orifices, such as aortic valve replacement devices. For example, FIG. 21C is a schematic top view of the native mitral valve MV shown in FIG. 21A and showing the heart valve repair device 100 (shown in dotted lines) and a prosthetic heart valve 180 implanted at the native mitral valve MV.

Figure 22:
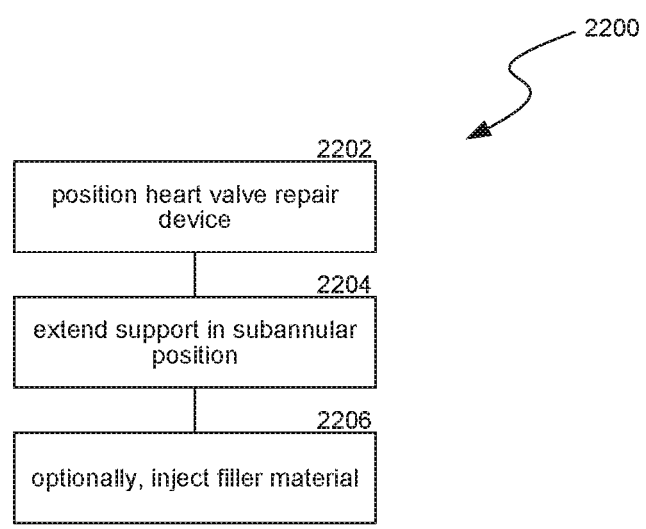
FIG. 22 illustrates a method for repairing a native valve of a patient in accordance with an embodiment of the present technology.

As described above with respect to FIGS. 7-10B, a variety of percutaneous and minimally invasive techniques can be used to access and implant the heart valve repair devices disclosed herein. In one specific embodiment, and in accordance with an embodiment of the present technology, FIG. 22 illustrates a method 2200 for repairing a native valve of a patient. The method 2200 can include positioning a heart valve repair device in a subannular position and behind at least one leaflet, wherein the leaflet is connected to chordae tendineae (block 2202). The repair device can have a support in a contracted configuration. Optionally, the support can include an extension unit configured to be biocompatible with cardiac tissue at or near the native valve of the patient. The method 2200 can also include extending the support in the subannular position such that the support engages an interior surface of a heart wall and a backside of the at least one leaflet (block 2204). Further optional steps of the method 2200 can include injecting a filler material into the extension unit (block 2206).

In one embodiment, positioning of a heart valve repair device can include placing a percutaneously positioned guide catheter with its distal tip approaching one of the mitral valve commissures and positioned at the end of the groove behind the posterior leaflet. A steerable guidewire and flexible catheter can then be advanced from the guide catheter around the groove behind the posterior leaflet and in the direction of the other opposite commissure. Once the catheter is in place, the guidewire can be withdrawn and the repair device can be introduced (e.g., in a contracted configuration) through the flexible catheter. If necessary, a flexible secondary guiding catheter or sheath can be placed over the guidewire or catheter before introducing the repair device. The repair device can be contained in the contracted configuration by a thin extension unit or sheath during the introduction process. Once the repair device is positioned behind the posterior leaflet, the sheath is withdrawn and the device is deployed or inflated. Further guidance can be used to ensure that the projections, if present, expand between the tertiary chordae tendineae. In some embodiments, radiopaque markers can be incorporated in known locations on the catheter, the sheath, or the repair device to ensure proper delivery to the target location.

The repair devices, systems and methods disclosed herein may also be used to repair and/or treat regurgitant tricuspid valves. The tricuspid valve, like the mitral valve, has leaflets tethered by chordae tendineae. Such a repair device as disclosed herein might be deployed behind one, two or all three of the tricuspid valve leaflets.

In still further applications, embodiments of the repair devices in accordance with the present technology can be used to enhance the functionality of various prosthetic valves. For example, the repair device can be configured to push or brace prosthetic leaflets or prosthetic aptation devices implanted at a native heart valve thereby facilitating coaptation of the prosthetic leaflets. In particular examples, several embodiments of repair devices in accordance with the present technology can be used to at least partially coapt (a) the prosthetic aptation devices shown and described in U.S. Pat. No. 7,404,824 B1, filed by Webler et al. on Nov. 12, 2003, which is herein incorporated by reference or (b) the prosthetic leaflets of devices shown and described in U.S. Pat. No. 6,730,118, filed by Spenser et al. on Oct. 11, 2002 and/or U.S. Patent Publication No. 2008/0243245, filed by Thambar et al. on May 28, 2008, which is also incorporated herein by reference. In another embodiment, several embodiments of repair devices in accordance with the present technology can also be used concomitantly with other valve therapies, such as the MitraClip® device sold by Abbott Laboratories, which connects the free edges of the two leaflets of the mitral valve.

Various aspects of the present disclosure provide heart valve repair devices, systems and methods for bracing at least a portion of the posterior leaflet of the native mitral valve in a closed or partially closed position to reduce or eliminate regurgitation occurrence in the mitral valve, while retaining enough effective valve area to prevent any significant pressure gradient across the mitral valve. Other aspects of the present disclosure provide heart valve repair devices, systems and methods for reducing the effective area of the mitral orifice and/or rendering a mitral valve competent without substantially reshaping the native annulus. Additionally, while additional tethering or anchoring mechanisms known in the art can be used to anchor the device in the target location, the devices described herein do not require additional tethering or anchoring mechanisms.

Features of the prosthetic heart valve device components described above also can be interchanged to form additional embodiments of the present technology. For example, the appendage 135 of the repair device 101 illustrated in FIG. 14B can be incorporated into the repair device 100 shown in FIGS. 11A-11C, the repair devices 100a-100c described above with reference to FIGS. 14A, 15, 16A and 16B, and the repair device 1800 shown in FIG. 18.

The following Examples are illustrative of several embodiments of the present technology.

EXAMPLES

1. A method of repairing a native mitral valve having an anterior leaflet and a posterior leaflet between a left atrium and a left ventricle, comprising:
   implanting a repair device having a support and an appendage under the posterior leaflet; and
   causing the support to press against a portion of an underside of the posterior leaflet and thereby push at least a portion of the posterior leaflet toward the anterior leaflet and extend the appendage beyond an edge of the posterior leaflet toward the anterior leaflet.

2. A method of repairing a native mitral valve having an anterior leaflet and a posterior leaflet between a left atrium and a left ventricle, comprising:
   positioning a repair device in the left ventricle under the posterior leaflet and between a wall of the left ventricle and chordae tendineae; and
   engaging an underside of the posterior leaflet with a support of the repair device such that a portion of the posterior leaflet moves toward the anterior leaflet,
   wherein, in the engaged arrangement, the repair device further includes a flap extending beyond an edge of the posterior leaflet toward the anterior leaflet.

3. The method of any of examples 1-2 wherein causing the support to press against the underside of the posterior leaflet or engaging the underside of the posterior leaflet with the support comprises projecting at least a portion of the support in an anterior direction such that the support urges a portion of the posterior leaflet towards the anterior leaflet.

4. The method of any of examples 1-3 wherein:
   the support comprises an extension unit;
   positioning the repair device under the posterior leaflet comprises implanting the extension unit under the posterior leaflet in an unexpanded state; and
   causing the support to press against an underside of the posterior leaflet or engaging the underside of the posterior leaflet with the support comprises extending at least a portion of the extension unit such that the support presses against a wider portion of the posterior leaflet than in the unexpanded state.

5. The method of example 4 wherein the extension unit comprises an inflatable bladder and extending the extension unit comprises injecting an inflation medium into the inflatable bladder.

6. The method of example 5 wherein the inflation medium comprises a biocompatible fluid.

7. The method of example 5 wherein the inflation medium comprises a curable fluid that is injected into the bladder in a fluidic state and then cures to a hardened state.

8. The method of example 4 wherein the extension unit comprises a self-expanding metal structure and extending at least a portion of the extension unit comprises releasing the self-expanding metal structure from a collapsed state such that the self-expanding metal structure presses against the underside of the posterior leaflet.

9. The method of any of examples 1-8 wherein the support comprises a plurality of projections and a plurality of depressions, each depression being disposed between two of the projections, and causing the support to press against an underside of the posterior leaflet or engaging the underside of the posterior leaflet with the support comprises extending the projections along the underside of the posterior leaflet such that an upper side of the projections presses against the posterior leaflet and the chordae tendineae are positioned in at least some of the depressions.

10. A method for repairing a native valve of a patient, the method comprising:
    positioning a heart valve repair device in a subannular position behind at least one leaflet connected to chordae tendineae, the repair device having a support in an unexpanded configuration; and
    expanding the support in the subannular position such that the support engages an interior surface of a heart wall and a downstream-facing surface of the at least one leaflet,
    wherein the repair device is configured to reposition the leaflet into an at least partially closed position and brace the leaflet such that the function of the native valve is improved,
    wherein, in the expanded arrangement, the repair device further includes an appendage extending beyond an edge of the at least one leaflet toward another leaflet.

11. The method of example 10 wherein the native valve is a mitral valve, and wherein the heart wall is a left ventricular wall and the leaflet is a posterior mitral valve leaflet.

12. The method of examples 10 or 11 wherein prior to positioning the heart valve repair device the patient has mitral valve regurgitation, and wherein the repair device reduces the regurgitation after expanding the support in the subannular position.

13. The method of any one of examples 10-12 wherein the support comprises an extension unit configured to expand along the downstream-facing surface of the at least one leaflet.

14. The method of example 13 wherein the extension unit is configured to expand in a direction toward a free edge of the at least one leaflet.

15. The method of example 13 wherein tissue grows into the extension unit after the repair device braces the leaflet in the partially closed position.

16. The method of any one of examples 13-15 wherein the extension unit comprises a plurality of projections configured to extend between the chordae tendineae connected to the leaflet.

17. The method of any one of examples 13-16, further comprising injecting a filler material into the extension unit.

18. The method of example 17 wherein the filler material fills and expands the plurality of projections so as to extend between the chordae tendineae.

19. The method of example 10 wherein, after expanding, the support is held in place by chordae tendineae attached to the leaflet.

20. The method of example 19 wherein the support is retained between the chordae tendineae and the leaflet and a subannular wall of the heart.

21. The method of examples 19 or 20 wherein the chordae tendineae are basal or tertiary chordae tendineae.

22. The method of example 10 wherein the repair device is held in place without penetrating the leaflet or heart wall tissue.

23. The method of example 10, further comprising releasing the repair device at the subannular position from a delivery device, wherein the repair device resides substantially entirely on the subannular side of the leaflet after being released from the delivery device.

24. The method of example 10, further comprising releasing the repair device at the subannular position from a delivery device, wherein the support maintains the leaflet so as not to open wider than the partially closed position after being released from the delivery device.

25. The method of example 24 wherein the support allows the leaflet to move between the partially closed position and a completely closed position during a cardiac cycle.

26. The method of example 10 wherein the support maintains a first leaflet of the valve in the partially closed position so as to sealingly engage a second leaflet of the valve during a portion of a cardiac cycle.

27. The method of example 10 wherein the repair device further comprises at least one retention member, wherein the retention member extends through or between one or more of the valve leaflets to a super-annular side thereof to maintain the support in the subannular position.

28. The method of example 10 wherein the repair device further comprises at least one retention member configured to engage the inward facing wall of the heart.

29. The method of example 10 wherein the support is expanded by injecting a fluid therein.

30. The method of example 10 wherein expanding the support includes releasing the support from a constrained configuration such that the support self-expands to an expanded configuration.

31. The method of example 10 wherein the support is expanded at least partially by absorption of blood or other body fluids.

32. The method of example 10 wherein an effective orifice area of the valve is reduced when the support is expanded.

33. The method of example 10 wherein expansion of the support changes the shape of an annulus of the valve and/or a shape of a functional orifice of the valve.

34. The method of example 10 wherein expansion of the support repositions the at least one leaflet such that an inward facing surface thereof coapts with an opposing surface of a second leaflet of the native valve during at least a portion of the cardiac cycle.

35. The method of example 10 wherein the placement and expansion of the support does not substantially change the shape of an annulus of the valve.

36. A repair device for repairing a native mitral valve having an anterior leaflet and a posterior leaflet between a left atrium and a left ventricle, the repair device comprising:
   a support having (a) a contracted configuration in which the support is sized to be inserted under the posterior leaflet between a wall of the left ventricle and chordae tendineae and (b) an extended configuration in which the support projects anteriorly with respect to a posterior wall of the left ventricle by a distance sufficient to position at least a portion of the posterior leaflet toward the anterior leaflet sufficiently to improve coaptation of the posterior and anterior leaflets; and
   an appendage, wherein in the extended configuration, the appendage extends beyond an edge of the posterior leaflet toward the anterior leaflet.

37. The repair device of example 36, wherein the support comprises an extension unit configured to push at least a portion of the leaflet towards an opposing leaflet of the native valve.

38. The repair device of example 37 wherein the extension unit is expandable from a contracted configuration to an expanded configuration.

39 The repair device of example 38 wherein the extension unit comprises an inflatable or fillable member.

40. The repair device of example 39, further comprising a port in communication with the inflatable or fillable member for delivering a fluid thereto.

41. The repair device of example 37 wherein the support comprises an elongated spine, the extension unit being coupled to the spine.

42. The repair device of example 41 wherein the extension unit is substantially more flexible than the spine in the contracted configuration.

43. The repair device of example 41 wherein the spine has a longitudinal axis and the extension unit is configured to expand in a direction transverse to the longitudinal axis.

44. The repair device of example 41 wherein the spine is curved in an unconstrained state and the extension unit is configured to expand in a radial direction relative to the spine.

45. The repair device of example 37 wherein the extension unit comprises a flexible cover extending around the spine.

46. The repair device of example 45 wherein the flexible cover is inflatable or fillable with a fluid.

47. The repair device of example 37 wherein the extension unit is substantially more rigid in the expanded configuration.

48. The repair device of example 36 wherein the support is formed of a biocompatible material for promoting tissue ingrowth.

49. The repair device of any one of examples 36-48 wherein the support is expandable.

50. The repair device of any one of examples 36-49 wherein the support is configured to conform to a shape defined by native tissue in the subannular position.

51. The repair device of example 50 wherein the support is configured to be held in place by chordae tendineae attached to the valve leaflet.

52. The repair device of example 51 wherein the support is configured to be compressively retained between the chordae tendineae and the leaflet and a subannular wall of the heart.

53. The repair device of example 36 wherein the support is configured to be held in the subannular position without penetrating the leaflet or heart wall tissue.

54. The repair device of example 36 wherein the support is configured to reside substantially entirely on the subannular side of the leaflet.

55. The repair device of example 36 wherein the support is configured to maintain the leaflet so as not to open wider than the partially closed position.

56. The repair device of example 55 wherein the support is configured to allow the leaflet to move between the partially closed position and a completely closed position during a cardiac cycle.

57. The repair device of example 36 wherein the support maintains a first leaflet of the valve in the partially closed position so as to sealingly engage a second leaflet of the valve during a portion of a cardiac cycle.

58. The repair device of any one of examples 36-57 wherein the repair device has a triangular or polygonal cross-section.

59. The repair device of any one of examples 36-58 wherein the repair device includes a plurality of projections configured to expand between and engage chordae tendineae attached to the leaflet.

60. The repair device of example 59 wherein the support is preformed to include the plurality of projections when in a deployed configuration.

61. The repair device of example 60 wherein the support includes at least one bladder configured to receive filler material, and wherein the support is expandable with the filler material to form the plurality of projections when the repair device is in a deployed configuration.

62. The repair device of example 36-61 wherein the support has a first radial cross-section near a first end of the support, a second radial cross-section near a second end of the support, and a third radial cross-section near a central region of the support, and wherein the first, second, and third radial cross-sections are substantially equal.

63. The repair device of example 36-62 wherein the support has a first radial cross-section near a first end of the support, a second radial cross-section near a second end of the support, and a third radial cross-section near a central region of the support, and wherein the third radial cross-section is greater than the first and second radial cross-sections.

64. The repair device of example 36-61 wherein the support has a first radial cross-section near a first end of the support, a second radial cross-section near a second end of the support, and a third radial cross-section near a central region of the support, and wherein the first radial cross-section is greater than the second and third radial cross-sections.

65. The repair device of any one of examples 36-64 wherein the support engages an outward-facing surface of a plurality of leaflets.

66. The repair device of any one of examples 36-65 wherein the native valve is a mitral valve, and wherein the support is configured to engage an underside of a posterior leaflet of the mitral valve.

67. The repair device of example 66 wherein the support is configured to reside substantially entirely under the posterior leaflet.

68. The repair device of any one of examples 36-66 wherein the native valve is a tricuspid valve, and wherein the support is configured to engage an underside of a leaflet of the tricuspid valve.

69. The repair device of any one of examples 36-66 wherein the native valve is a mitral valve, and wherein the support is configured to—
engage the outward-facing surface of a posterior leaflet; and
extend beyond native valve commissures to support at a least a portion of an anterior leaflet.

70. The repair device of any one of examples 36-69 wherein the support includes a flexible and resilient spine.

71. The repair device of example 70 wherein the spine is one of a wire, a stent structure, a coiled spring or a braided tube.

72. The repair device of example 70 wherein the support further comprises a flexible cover extending around the spine.

73. The repair device of example 72 wherein the flexible cover is inflatable or fillable with a fluid.

74. The repair device of any one of examples 36-70 wherein the support is self-expanding.

75. The repair device of any one of examples 36-70 wherein the support includes at least one of nitinol or stainless steel.

76. The repair device of any one of examples 36-70 wherein the support expands to form a "C" shape to conform to a portion of a native mitral valve.

77. The repair device of any one of examples 36-70 wherein the support includes a subannular engaging surface, and wherein the subannular engaging surface includes one or more peaks and one or more valleys.

78. A system to treat a native valve of a patient, the system comprising:
a prosthetic valve repair device implantable in a subannular position relative to the native valve and having a support and an appendage, wherein the support is configured to engage an interior surface of a heart wall and an outward-facing surface of a leaflet of the native valve in a subannular position of the native valve, and wherein the support is configured to change an effective annulus shape and/or an effective annulus cross-sectional dimension when the device is in a deployed configuration, and further wherein the appendage is configured to extend beyond an edge of the leaflet toward an adjacent leaflet; and
a prosthetic valve having—
a radially expandable support structure with a lumen; and
a valve in the lumen and coupled to the support structure;
wherein the radially expandable support structure is configured to be deployed within the native valve when the prosthetic valve repair device is implanted in the subannular position and supported within the changed annulus shape or changed annulus cross-sectional dimension.

79. The system of example 78, further comprising a delivery catheter having a lumen configured to retain the prosthetic valve device in a delivery configuration having a lower profile than the deployed configuration.

80. The system of examples 78 or 79 wherein the native valve has a plurality of native leaflets joined at commissures, and wherein the support is configured to engage the outward-facing surface of at least one leaflet and extend beyond the commissures.

81. The system of example 80 wherein the native valve is a mitral valve, and wherein the support is configured to—
engage the outward-facing surface of a posterior leaflet; and
extend beyond the commissures to support at a least a portion of an anterior leaflet.

82. The system of any one of examples 78-81 wherein the prosthetic heart valve has a substantially circular cross-sectional dimension.

83. The system of example 82 wherein the support is configured to change the effective annulus shape from a non-circular cross-section to a substantially circular cross-section.

CONCLUSION

The above detailed descriptions of embodiments of the technology are not intended to be exhaustive or to limit the technology to the precise form disclosed above. Although specific embodiments of, and examples for, the technology are described above for illustrative purposes, various equivalent modifications are possible within the scope of the technology as those skilled in the relevant art will recognize. For example, although steps are presented in a given order, alternative embodiments may perform steps in a different order. The various embodiments described herein may also be combined to provide further embodiments. The embodiments, features, systems, devices, materials, methods and techniques described herein may, in certain embodiments, be applied to or used in connection with any one or more of the embodiments, features, systems, devices, materials, methods and techniques disclosed in U.S. Provisional Patent Application No. 61/825,491, which is incorporated herein by reference in its entirety.

From the foregoing, it will be appreciated that specific embodiments of the technology have been described herein for purposes of illustration, but well-known structures and functions have not been shown or described in detail to avoid unnecessarily obscuring the description of the embodiments of the technology. Where the context permits, singular or plural terms may also include the plural or singular term, respectively.

Moreover, unless the word "or" is expressly limited to mean only a single item exclusive from the other items in reference to a list of two or more items, then the use of "or" in such a list is to be interpreted as including (a) any single item in the list, (b) all of the items in the list, or (c) any combination of the items in the list. Additionally, the term "comprising" is used throughout to mean including at least the recited feature(s) such that any greater number of the same feature and/or additional types of other features are not precluded. It will also be appreciated that specific embodiments have been described herein for purposes of illustration, but that various modifications may be made without deviating from the technology. Further, while advantages associated with certain embodiments of the technology have been described in the context of those embodiments, other embodiments may also exhibit such advantages, and not all embodiments need necessarily exhibit such advantages to fall within the scope of the technology. Accordingly, the disclosure and associated technology can encompass other embodiments not expressly shown or described herein.

I claim:

1. A method of repairing a native mitral valve having an anterior leaflet and a posterior leaflet between a left atrium and a left ventricle, comprising:
   positioning a repair device in the left ventricle under the posterior leaflet and between a wall of the left ventricle and chordae tendineae; and
   engaging an underside of the posterior leaflet with a support of the repair device such that a portion of the posterior leaflet moves toward the anterior leaflet,
   wherein, in the engaged arrangement, the repair device further includes a flap extending beyond an edge of the posterior leaflet toward the anterior leaflet.

2. A method for repairing a native valve of a patient, the method comprising:
   positioning a heart valve repair device in a subannular position behind at least one leaflet connected to chordae tendineae, the repair device having a support in an unexpanded configuration; and
   expanding the support in the subannular position such that the support engages an interior surface of a heart wall and a downstream-facing surface of the at least one leaflet,
   wherein the repair device is configured to reposition the at least one leaflet into an at least partially closed position and brace the at least one leaflet such that the function of the native valve is improved,
   wherein, in the expanded arrangement, the repair device further includes an appendage extending beyond an edge of the at least one leaflet toward another adjacent leaflet.

3. The method of claim 2 wherein the native valve is a mitral valve, and wherein the heart wall is a left ventricular wall and the at least one leaflet is a posterior mitral valve leaflet.

4. The method of claim 2 wherein prior to positioning the heart valve repair device the patient has mitral valve regurgitation, and wherein the repair device reduces the regurgitation after expanding the support in the subannular position.

5. The method of claim 2 wherein the support comprises an extension unit configured to expand along the downstream-facing surface of the at least one leaflet.

6. The method of claim 5 wherein the extension unit is configured to expand in a direction toward the edge of the at least one leaflet.

7. The method of claim 5 wherein tissue grows into the extension unit after the repair device braces the at least one leaflet in the at least partially closed position.

8. The method of claim 5 wherein the extension unit comprises a plurality of projections configured to extend between the chordae tendineae connected to the at least one leaflet.

9. The method of claim 5, further comprising injecting a filler material into the extension unit.

10. The method of claim 9 wherein the extension unit comprises a plurality of projections configured to extend between the chordae tendineae connected to the at least one leaflet and wherein the filler material fills and expands the plurality of projections so as to extend between the chordae tendineae.

11. The method of claim 2 wherein after expanding, the support is held in place by chordae tendineae attached to the at least one leaflet.

12. The method of claim 11 wherein the support is retained between the chordae tendineae and the at least one leaflet and the heart wall.

13. The method of claim 2 wherein the repair device is held in place without penetrating the at least one leaflet or heart wall tissue.

14. A method of repairing a native mitral valve having anterior leaflet and a posterior leaflet between a left atrium and a left ventricle, comprising
   implanting a repair device having a support and an appendage under the posterior leaflet, wherein
      the support comprises an extension unit, and
      implanting the repair device under the posterior leaflet comprises implanting the extension unit under the posterior leaflet in an unexpanded state; and
   causing the support to press against a portion of an underside of the posterior leaflet and thereby push at least a portion of the posterior leaflet toward the anterior leaflet and extend the appendage beyond an edge of the posterior leaflet toward the anterior leaflet wherein causing the support to press against the underside of the posterior leaflet or engaging the underside of the posterior leaflet with the support comprises extending at least a portion of the extension unit such that the support presses against a wider portion of the posterior leaflet than in the unexpanded state.

15. The method of claim 14 wherein the extension unit comprises an inflatable bladder and extending the at least a portion of the extension unit comprises injecting an inflation medium into the inflatable bladder.

16. The method of claim 15 wherein the inflation medium comprises a biocompatible fluid.

17. The method of claim 15 wherein the inflation medium comprises a curable fluid that is injected into the inflatable bladder in a fluidic state and then cures to a hardened state.

18. The method of claim 14 wherein the extension unit comprises a self-expanding metal structure and the extending at least a portion of the extension unit comprises releasing the self-expanding metal structure from a collapsed state such that the self-expanding metal structure presses against the underside of the posterior leaflet.

19. A method of repairing a native mitral valve having an anterior leaflet and a posterior leaflet between a left atrium and a left ventricle, comprising:
  implanting a repair device having a support and an appendage under the posterior leaflet, wherein the support comprises a plurality of projections and a plurality of depressions, each depression being disposed between two of the projections, and
  causing the support to press against a portion of an underside of the posterior leaflet and thereby push at least a portion of the posterior leaflet toward the anterior leaflet and extend the appendage beyond an edge of the posterior leaflet toward the anterior leaflet, wherein causing the support to press against an underside of the posterior leaflet or engaging the underside of the posterior leaflet with the support comprises extending the projections along the underside of the posterior leaflet such that an upper side of the projections presses against the posterior leaflet and the chordae tendineae are positioned in at least some of the depressions.

* * * * *